US007371721B2

(12) United States Patent
Henriksen et al.

(10) Patent No.: US 7,371,721 B2
(45) Date of Patent: *May 13, 2008

(54) USE OF GLP-2 AND RELATED COMPOUNDS FOR THE TREATMENT, PREVENTION, DIAGNOSIS, AND PROGNOSIS OF BONE-RELATED DISORDERS AND CALCIUM HOMEOSTASIS RELATED SYNDROMES

(75) Inventors: Dennis Bang Henriksen, Allerød (DK); Jens Juul Holst, Hellérup (DK)

(73) Assignee: Sanos Bioscience A/S, Herlev (DK)

( * ) Notice: Subject to any disclaimer, the term of this patent is extended or adjusted under 35 U.S.C. 154(b) by 386 days.

This patent is subject to a terminal disclaimer.

(21) Appl. No.: 11/035,826

(22) Filed: Jan. 14, 2005

(65) Prior Publication Data

US 2005/0282749 A1    Dec. 22, 2005

Related U.S. Application Data

(63) Continuation-in-part of application No. 10/393,524, filed on Mar. 20, 2003, now Pat. No. 7,186,683, which is a continuation-in-part of application No. 09/954,304, filed on Sep. 17, 2001, now Pat. No. 6,770,620.

(60) Provisional application No. 60/371,307, filed on Apr. 10, 2002.

(30) Foreign Application Priority Data

Sep. 18, 2000  (GB) ................... 0022844.5
Dec. 7, 2000   (GB) ................... 0029920.6

(51) Int. Cl.
    *A61K 38/26*  (2006.01)
(52) U.S. Cl. .............. 514/2; 514/12; 514/21; 530/308; 530/324
(58) Field of Classification Search ............ None
    See application file for complete search history.

(56) References Cited

U.S. PATENT DOCUMENTS

| 5,317,010 | A | * | 5/1994 | Pang et al. ............ 514/12 |
| 5,556,940 | A | * | 9/1996 | Willick et al. ............ 530/317 |
| 5,789,379 | A | | 8/1998 | Drucker et al. |
| 5,834,428 | A | | 11/1998 | Drucker |
| 5,912,229 | A | | 6/1999 | Thim et al. |
| 5,952,301 | A | | 9/1999 | Drucker |
| 5,990,077 | A | | 11/1999 | Drucker |
| 5,994,500 | A | | 11/1999 | Drucker et al. |
| 6,037,143 | A | | 3/2000 | Wagner et al. |
| 6,048,524 | A | | 4/2000 | Selden et al. |
| 6,051,557 | A | | 4/2000 | Drucker |
| 6,077,949 | A | | 6/2000 | Munroe et al. |
| 6,110,949 | A | * | 8/2000 | Villhauer ............ 514/365 |
| 6,166,063 | A | | 12/2000 | Villhauer |
| 6,184,201 | B1 | | 2/2001 | Drucker et al. |
| 6,770,620 | B2 | | 8/2004 | Henriksen |
| 6,943,151 | B2 | * | 9/2005 | Henriksen et al. ............ 514/21 |
| 7,001,911 | B2 | * | 2/2006 | Salvati et al. ............ 514/292 |
| 7,186,683 | B2 | * | 3/2007 | Henriksen et al. ............ 514/2 |
| 2004/0082507 | A1 | | 4/2004 | Henriksen et al. |

FOREIGN PATENT DOCUMENTS

| EP | 0 955 314 A3 | 10/1999 |
| WO | WO-96/32414 | 10/1996 |
| WO | WO-97/31943 | 9/1997 |
| WO | WO-97/39031 | 10/1997 |
| WO | WO-98/01535 | 1/1998 |
| WO | WO-98/03547 | 1/1998 |
| WO | WO-98/08872 | 3/1998 |
| WO | WO-98/24813 | 6/1998 |
| WO | WO-98/25644 | 6/1998 |
| WO | WO-98/25955 | 6/1998 |
| WO | WO-98/52600 | 11/1998 |
| WO | WO-99/06059 | 2/1999 |
| WO | WO-99/14239 | 3/1999 |
| WO | WO-99/37793 | 7/1999 |
| WO | WO-99/38501 | 8/1999 |
| WO | WO-99/43361 | 9/1999 |
| WO | WO-99/46283 | 9/1999 |
| WO | WO-99/58144 | 11/1999 |
| WO | WO-00/10549 | 3/2000 |
| WO | WO-00/18371 | 4/2000 |

(Continued)

OTHER PUBLICATIONS

Francis, Roger M., "Bisphosphonates in the Treatment of osteoporosis in 1997: A Review"; Current Therapeutic Research, vol. 58, pp. 656-678, No. 10, Oct. 1997.

(Continued)

*Primary Examiner*—Anish Gupta
(74) *Attorney, Agent, or Firm*—Gregory B. Butler; Edwards Angell Palmer & Dodge LLP

(57) ABSTRACT

The present invention relates to methods for prevention and treatment of bone-related disorders and calcium homeostasis related syndromes using a GLP-2 molecule or GLP-2 activator either alone or in combination with another therapeutic. The present invention also encompasses methods of diagnosing or monitoring the progression of a disorder. The invention also encompasses methods of monitoring the effectiveness of treatment of the invention.

16 Claims, 3 Drawing Sheets

FOREIGN PATENT DOCUMENTS

| | | |
|---|---|---|
| WO | WO-00/20592 | 4/2000 |
| WO | WO-00/34331 | 6/2000 |
| WO | WO-00/34332 | 6/2000 |
| WO | WO-00/37053 | 6/2000 |
| WO | WO-00/42026 | 7/2000 |
| WO | WO-00/53208 | 9/2000 |
| WO | WO-01/04156 | 1/2001 |
| WO | WO-01/41779 | 6/2001 |
| WO | WO-01/87332 | 11/2001 |
| WO | WO-01/98331 | 12/2001 |
| WO | WO-02/10195 | 2/2002 |
| WO | WO-02/24214 | 3/2002 |
| WO | WO-02/066062 | 8/2002 |

OTHER PUBLICATIONS

Haderslev, K.V. et al., "Short-term Administration of Gluagon-like Peptide-2. Effects on Bone Mineral Density and Markers of Bone Turnover in Short-Bowel Patients with No Colon"; Taylor & Francis Healthsciences, pp. 392-398.

Andreasen et al., 1994, "Secretion of glucagon-like-peptide-1 and reactive hypoglycemia after partial gastrectomy", Digestion 55:221-228.

Bell et al., 1983, "Exon duplication and divergence in the human preproglucagon gene", Nature 304:368-371.

Buhl et al., 1988, "Naturally occurring products of proglucagon 111-160 in the porcine and human small intestine." J. Biol. Chem. 263:8621-8624.

Cheeseman and Tseng, 1996, "The effect of GIP and glucagon-like peptides on intestinal basolateral membrane hexose transport". Am. J. Physiol. 271:G477-G482.

Drucker et al., 1996 "Induction of intestinal epithelial proliferation by glucagon-like peptide 2" Proc. Natl. Acad. Sci. USA 93:7911-7916.

Graham and Malaty, 1999, "Alendronate gastric ulcers", Aliment Pharmacol. Ther. 13:515-519.

Hartman et al., 2000, "In vivo and in vitro degradation of glucagon-like peptide 2 in humans", J. Clin. Endocrinol. Metab. 85:2884-2888.

Irwin and Wong, 1995, "Trout and chicken proglucagon: alternative splicing generates mRNA transcripts encoding lucagon-like peptide 2", Mol. Endocrinol. 9:267-277.

Jelinek et al., 1993, "Expression cloning and signaling properties of the rat glucagon receptor", Science 259:1614-1616.

Jeppesen et al., 2000, "Elevated plasma glucagon-like peptide 1 and 2 concentrations in ileum resected shor bowel patients with a preserved colon", Gut 47:370-376.

Mojsov, 1992, "Structural requirements for biological activity of glucagon-like peptide-1", Intl. J. Pep. Prot. Res. 40:333-343.

Munroe et al., 1999, Prototypic G protein-coupled receptor for the intestinotrophic factor glucagon-like peptide 2, Proc. Natl. Acad. Sci. USA 96:1569-1573.

Nishi and Steiner, 1990, "Cloning and complementary DNAs encoding islet amyloid polypeptide, insulin, and glucagon precursors from a New World rodent, the degu, *Octodon degu*", Mol. Endocrinol. 4:1192-1198.

Persson et al., 1997, "Hormone replacement therapy and the risk of breast cancer. Nested case-control study in a cohort of Swedish women attending mammography screening", Intl. J. Can. 72:758-761.

Rosenquist et al., 1998, "Serum CrossLaps ONe Step ELISA. First application of monclonal antibodies for measurement in serum of bone-related degradation products from C-terminal telopeptides of type 1 collagen", Clin. Chem. 44:-2281-2289.

Schlemmer and Hassager, 1999, "Acute fasting diminishes the circadian rhythm of biochemical markers of bone resorption", Eur. J. Endocrinol. 140:332-337.

Schlemmer et al., 1994, Posture, age, menopause and osteopenia do not influence the circadian variation in the urinary excretion of pyridinium crosslinks:, J. Bone Mineral Res. 9:1883-1888.

Thorens, 1992 "Expression cloning of pancreatic cell receptor for the gluco-incretin hormone glucagon-like peptide 1" Proc. Natl. Acad. Sci USA 89:8641-8645.

Unger and Orci, eds., 1981, "Glucagon. Physiology, Pathophysiology and Morphology of the Pancreatic A-Cells", New York, Elsevier, pp. 140-120.

\* cited by examiner

USE OF GLP-2 AND RELATED COMPOUNDS FOR THE TREATMENT, PREVENTION, DIAGNOSIS, AND PROGNOSIS OF BONE-RELATED DISORDERS AND CALCIUM HOMEOSTASIS RELATED SYNDROMES

CROSS-REFERENCE TO RELATED APPLICATIONS

The present application is a continuation-in-part of U.S. Ser. No. 10/393,524 filed Mar. 20, 2003, now U.S. Pat. No. 7,186,683, which was itself a continuation-in-part of U.S. Ser. No. 09/954,304 filed on Sep. 17, 2001, now U.S. Pat. No. 6,770,620 which application claims priority to co-pending United Kingdom Patent Application No. GB 0022844.5, filed Sep. 18, 2000 and co-pending United Kingdom Patent Application No. GB 0029920.6, filed Dec. 7, 2000 and further priority to U.S. Ser. No. 60/371,307 as filed on Apr. 10, 2002. These priority claims are maintained in this application and the disclosures of the 10/393,524, 60/371,307; 09/954,304; GB 0022844.5; and GB 0029920.6 applications are each incorporated herein by reference.

1. FIELD OF THE INVENTION

The present invention relates to methods for prevention and treatment of bone-related disorders or calcium homeostasis related syndromes using a GLP-2 or GLP-2 activator either alone or in combination with another therapeutic. The present invention also encompasses methods of diagnosing or monitoring the progression of a disorder. The invention also encompasses methods of monitoring the effectiveness of treatment of the invention.

2. BACKGROUND OF THE INVENTION

Glucagon and Related Peptides

Glucagon is a hormone that is released in response to low glucose levels and stimulates glucose production. Thus, it plays a role in counteracting insulin in blood glucose homeostasis (Unger and Orci, 1990, Glucagon in Diabetes Mellitus, 4$^{th}$ edition, Elsevier p. 104-120). Glucagon arises from the post-translational processing of a larger precursor molecule, proglucagon.

Proglucagon is produced in both the α-cells of the pancreas as well as in the enteroendocrine L-cells of the intestine. It is subject to differential processing in the different tissues in which it is expressed. For example, glucagon is selectively excised from the precursor in the pancreas while two smaller peptides, glucagon-like peptide-1 (GLP-1) and glucagon-like peptide-2 (GLP-2), are produced in the intestine. GLP-1 and GLP-2 consist of amino acid residues 78-107 and 126-158 of proglucagon respectively (Bell et al., 1983, Nature 304: 368-371; Buhl et al., 1988, J. Biol. Chem., 263:8621; Nishi and Steiner, 1990, Mol. Endocrinol. 4:1192-1198; Irwin and Wong, 1995, Mol. Endocrinol. 9:267-277).

Glucagon and GLP-1 have competing biological activities. GLP-1 stimulates insulin secretion, glucose uptake, and cAMP formation in response to the presence and absorption of nutrients in the gut, whereas glucagon increases glucose output by the liver, skeletal muscle tissue, and adipose tissue during periods of fasting (see, e.g., Mojsov, 1992, Int. J. Pep. Prot. Res. 40:333-343; Andreasen et al., 1994, Digestion 55:221-228). Specific GLP-1 receptors have been identified (Thorens, 1992, Proc. Natl. Acad. Sci. 89:8641-8645) which are distinct from the glucagon receptor (Jelinek et al., 1993, Science 259:1614-1616).

GLP-2 is 33 amino acid fragment of proglucagon. Various vertebrate forms (including human) of GLP-2 have been reported. GLP-2 has intestinotrophic activity (U.S. Pat. No. 5,834,428).

When administered exogenously, GLP-2 can produce a marked increase in the proliferation of small intestinal epithelium in mice, with no apparent side effects (Drucker et al., 1996, Proc. Natl. Acad. Sci. 93:7911-7916). Moreover, GLP-2 increases maximal transport rate of D-glucose across the intestinal basolateral membrane (Cheeseman and Tseng, 1996, Am. J. Phys. 271: G477-G482). GLP-2 may act via a G-protein-coupled receptor (Munroe et al., 1999, Proc. Natl. Acad. Sci. 96:1569-1573).

Disorders

Osteoporosis is the most common form of metabolic bone disease. It affects more than 25 million people in the United States and causes more than 1.3 million bone fractures each year, including approximately 500,000 spine, 250,000 hip and 240,000 wrist fractures. Hip fractures are the most serious consequence of osteoporosis, with 5-20% of patients dying within one year of the fracture and over 50% of survivors being incapacitated.

Osteoporosis is commonly observed in post-menopausal women, but it also occurs in elderly and young individuals. The disease is characterized by low bone mass and a deterioration of bone tissue, with a consequent increase in bone fragility and susceptibility to fracture. Although the etiology of osteoporosis is not known, its onset is associated with several factors such as increased age, decreased hormone level, and decreased calcium levels. Osteoporosis may occur in elderly men as androgen levels fall. Androgens play an important role in bone formation/maintenance and promote the synthesis of collagen, which provides a repository for the calcium and phosphorus. Osteoporosis may also be due to increased secretion of parathyroid hormone, which reduces bone formation and enhances bone absorption. Osteoporosis can also be caused by kidney degeneration, which reduces the activity of hydroxylase-activating vitamin D, decreasing intestinal calcium absorption, and precipitating the loss of bone matrix. Mobilization of nutrient stores in bone can be achieved by stimulating osteoclastic bone resorption. Likewise, resorptive activity can be reversed by increasing dietary availability of nutrients.

Dietary intake of calcium has been shown to regulate bone metabolism. We have established that intake of oral glucose decreases bone resorption, resulting in a fully expressed decrease within two hours following glucose administration. This response to glucose intake is independent of gender and age. A comparable effect was also demonstrated following protein administration.

Bone-related disorders are characterized by bone loss resulting from an imbalance between bone resorption and bone formation. The potential for bone loss is directly related to the bone's normal rate of resorption and can amount to over 5% per year in humans immediately following menopause.

There are currently two main types of pharmaceutical treatment for osteoporosis, both aimed at reduction of bone resorption. The first involves the administration of an anti-resorptive compound. For example, estrogen has been used as an anti-resorptive agent to reduce fractures. However, estrogen fails to restore bone to levels of that in a skeleton of a young adult. Furthermore, long-term estrogen therapy has been implicated in a variety of disorders, including an increase in the risk of uterine cancer, endometrial cancer, and possibly breast cancer (Persson et al., 1997, "Hormone replacement therapy and the risk of breast cancer. Nested case-control study in a cohort of Swedish women attending mammography screening", Int. J. Can. 72:758-761). For these reasons, many women avoid treatment of osteoporosis with estrogen.

A second type of pharmaceutical therapy for treating osteoporosis uses an agent that inhibits bone resorption and as a consequence increases bone mass. These agents, such as alendronate, can in some incidences restore the amount of bone to that of an established premenopausal skeleton. However, long term therapy will lower bone formation as well and increase in bone mass is only seen in the timeframe where bone resorption suppression supersedes the decline in bone formation. Furthermore, alendronate administration can cause undesirable side effects, for example gastric ulceration (Graham et al., 1999, Aliment Pharmacol. Ther. 4:515-9).

The significant risks associated with the currently available pharmaceutical therapies (such as estrogen and alendronate) highlight the need to develop safer therapies for treating or preventing osteoporosis and other bone-related disorders. Therefore, there is a need for methods for treating or preventing a bone disorder, such as osteoporosis, that do not carry the aforementioned risks.

Conditions treatable according to the invention include but are not limited to osteoporosis, hypercalcemia of malignancy, osteopenia due to bone metastases, periodontal disease, hyperparathyroidism, periarticular erosions in rheumatoid arthritis, Paget's disease, osteodystrophy, myositis ossificans, Bechterew's disease, malignant hypercalcemia, osteolytic lesions produced by bone metastasis, bone loss due to immobilization, bone loss due to sex steroid hormone deficiency, bone abnormalities due to steroid hormone treatment, bone abnormalities caused by cancer therapeutics, osteomalacia, osteomalacia, hyperostosis, osteopetrosis, metastatic bone disease, immobilization-induced osteopenia, or glucocorticoid-induced osteoporosis.

Certain conditions not at first sight related to bone are known to give rise to excessive bone resorption and net bone loss by mechanisms that have not previously been explained. Patients who have suffered damage to the spinal cord at a high level and who are paralysed suffer bone mass loss which is not explicable on the basis of immobilisation alone. There is a need for effective treatment of this condition.

Patients who have had bowel resection or who have other bowel disorders often show symptoms of excessive bone resorption with net bone mass loss in a manner which is not explicable by say poor calcium absorption from diet. Again, there is a need for effective treatment.

Amongst the conditions listed above is hypercalcaemia, which may be produced by a number of causes. These may have significantly different underlying mechanisms. Hypercalcemia accompanying malignancy is due to local osteolysis involving stimulation of osteoclast formation and activity by the different soluble factors tumour cells can produce. These factors (eicosanoids, cytokines, growth factors and hormones) act on osteoblatic stromal cells that can produce RANK-L, which can bind to RANK on osteclastic precursor cells and in the presence of Macrophage-colony stimulating factor, enhance the differentiation and fusion of these cells to produce functioning multinucleated osteoclasts. Among the hormones released by cancer cells, one can mention parathyroid related hormone (PTH), which is often secreted by breast cancer cells. Some tumour cells can produce soluble RANKL. Additionally, they can also produce various proteases, which are also important for the invasion of the tumour into bone tissue.

As discussed further below, PTH in the form of an N-terminal fragment is a recently developed treatment for osteoporosis, but after an intitial period of increasing the rate of bone formation, PTH also increases the rate of bone resorption and can lead to hypercalcaemia. PTH induced hypercalcaemia, in contrast to that induced by malignancy, is more of a systemic phenomenon involving the whole skeletal system and kidneys. Contributing factors include stimulation of 1,25-(OH)(2)D production, stimulation of tubular calcium re-absorption in the kidney, and increased bone resorption. PTH stimulates marrow stromal cells or osteoblasts to produce soluble and membrane-associated factors that act upon osteoclastprecursors to increase their proliferation and/or differentiation and upon mature osteoclasts to increase osteoclastic resorptive activity. Among these factors are macrophage colony-stimulating factor (M-CSF), IL-6, IL-11, and the TNF family ligand, RANKL. Osteoclasts and their precursors express the M-CSF receptor c-fms and the RANKL receptor RANK and thereby respond to M-CSF and RANKL, respectively. These cytokines, delivered via direct cell-to-cell interactions with stromal cells or osteoblasts, then promote the differentiation and survival ofmature osteoclasts.

Increased resorption following the induction of increased formation may not only lead to hypercalcaemia, but it also limits the therapeutic window and thus the gain in bone mass over the maximally allowed 1.5 to 2 years treatment period. Since it is prohibited to prolong the treatment with PTH analogues in order to further increase bone mass, enhancement of efficacy would require inhibition of the parallel increases in bone resorption. Recently, this intention was implemented in a trial combining PTH with alendronate, which, however, failed to provide major benefits in this combination. It is tempting to speculate that the failure could be explained, at least in part, due to an unphysiologic inhibition of bone resorption by bisphosphonates. So far little to no attention has been given to other potential combinations, which could provide a more physiological approach to the parallel inhibition of bone resorption.

In accordance with a major aspect of this invention, GLP-2 induces a prompt effect on osteoclasts and thereby bone resorption, provides therapeutic benefits when combined by PTH additional to the control of hypercalcaemia.

Other causes of hypercalcaemia include intoxication by vitamin D or vitamin A, such as may be encountered by patients on dialysis taking vitamin D replacement. A further hypercalcaemia treatable according to the invention, is hypercalcaemia induced by lithium treatment, or the use of aminophylline or thiazide diuretics. Bone loss due to treatment with glucocorticoid steroids as used in treating rheumatoid arthritis, e.g. dexamethasone, may also be treated in this way.

By decreasing the bone resorbing activity of osteoclasts, GLP-2 serves to increase the net rate of bone formation, thus removing calcium from the circulation into the bone.

3. SUMMARY OF THE INVENTION

The present invention relates to the prevention or treatment of a bone-related disorder (which may be a calcium homeostasis related syndrome) comprising administering to a patient a composition that increases GLP-2 activity. Compositions for administration according to the invention comprise a GLP-2 molecule or a GLP-2 activator. One or more additional therapeutic agents can be administered in conjunction with the compositions of the invention.

The invention includes particularly, a therapeutic composition comprising
a) a first active component which promotes bone formation and promotes bone resorption; and
b) a second active component which is a GLP-2, a variant, analogue, or derivative, or mimic of GLP-2 having the ability to bind and activate a GLP-2 receptor (especially an osteoclast GLP-2 receptor), or is a GLP-2 receptor agonist.

In such a composition, component (a) may be a PTH receptor binding ligand, especially one activating the PTH receptor (particularly the PTH type 1 receptor) to provide a functional signal, i.e. one of the same nature or effect as that provided upon binding thereto of PTH.

The PTH receptor binding ligand may preferably be PTH, an active fragment of PTH, PTHrP, an active fragment of PTHrP, or an analogue or derivative of any one of said ligands having the ability to bind and preferably to activate a PTH receptor.

Truncated and variant forms of PTH and PTHrP that may be used are discussed in detail below.

Said component (b) may be any of the forms of GLP-2 discussed below including its variants, analogues, derivatives and mimics, including GLP-2 (1-34).

A further aspect of the invention is a method of treatment of a patient having an undesirably low bone mass or an undesirably high rate of bone resorption or an undesirably low rate of bone formation, which method comprises administering to the patient a therapeutically effective amount of each of:
(a) a first active component which promotes bone formation and promotes bone resorption; and
b) a second active component which is a GLP-2, an analogue or derivative or mimic of GLP-2 having the ability to bind and activate a GLP-2 receptor, or is a GLP-2 receptor agonist.

In a particularly preferred embodiment, said component (a) is PTH (1-34) or PTH (1-84) and said component (b) is GLP-2 (1-34). Such a method may comprise the administration of components (a) and (b) simultaneously or sequentially in either order. Such a method may also include a step of performing a measurement of the patient's bone mass, or rate of bone resorption or rate of bone formation and determining the patient's need for said treatment based on the results of said measurement and or performing a measurement of the patient's bone mass, or rate of bone resorption or rate of bone formation after such treatment.

In another aspect, the invention includes a method of treating hypercalcaemia by therapy or by prophylaxis comprising administering to a patient in need thereof a therapeutically effective amount of a GLP-2, a variant, an analogue, or derivative or mimic of GLP-2 having the ability to bind and activate a GLP-2 receptor, or a GLP-2 receptor agonist.

Such treatment may be applied where said hypercalcaemia has been caused or potentially will be caused by treatment of the patient with a medicament known to cause hypercalcaemia as a side effect. The side effect causing medicament may be PTH or a substitute therefor, vitamin D, vitamin A, lithium, aminophylline, or a thiazide diuretic, Alternatively, the hypercalcaemia may be hypercalcaemia of malignancy. Also contemplated by the invention are methods for diagnosing a bone-related disorder or a calcium homeostasis related syndrome in a patient comprising:

(a) determining the level of GLP-2 molecule expressed in a normal tissue and a test tissue;
(b) comparing said levels of GLP-2 molecule expression in said tissues, wherein a decrease in said level of GLP-2 molecule expression in said test tissue indicates a bone-related disorder or a calcium homeostasis related syndrome.

Also contemplated by the invention are methods of monitoring the progression of a bone-related disorder or a calcium homeostasis related syndrome in a patient comprising:
(a) determining the level of GLP-2 molecule expressed in a first diseased tissue;
(b) determining the level of GLP-2 molecule expressed in a second diseased tissue, wherein said second diseased tissue is taken from the same patient as said first diseased tissue but at a later date; and
(c) comparing said levels of GLP-2 molecule expression in said first and second diseased tissues, wherein a decrease said level of GLP-2 molecule expression in said second diseased tissue indicates progression of said bone-related disorder or said calcium homeostasis related syndrome.

Also contemplated by the invention are methods of determining the effectiveness of treatment with a GLP-2 molecule or GLP-2 activator in a patient comprising:
(a) determining the level of one or more markers of bone resorption from a first patient tissue samples prior to said treatment and a second patient tissue sample after said treatment;
(b) comparing said levels of one or more markers in said tissue samples, wherein a decrease in said level in said second tissue sample indicates effective treatment.

3.1 Definitions

As used herein, the term GLP-2 or 'a GLP-2' or a 'GLP-2 molecule' includes each and any of the following:

a naturally occurring human form of GLP-2, including human GLP-2 (1-33) corresponding to amino acids 126-158 of human proglucagon or a naturally occurring animal, e.g. mammalian, form of GLP-2. Where a GLP-2 can be used according to the invention there may generally also be used variant peptides having a similar amino acid sequence to a naturally occurring GLP-2 and having GLP-2 receptor binding activity and optionally also GLP-2 receptor activating activity, including fragments of a full length GLP-2 and extensions of a full length GLP-2. Also, analogues, derivatives and mimics as described below may be used.

As used herein, the term "variant" or "variants" refers to variations of the nucleic acids that encode GLP-2 molecules or variations of an amino acid sequence of GLP-2 molecules. Homologues and analogs of a GLP-2 molecule are contemplated. Encompassed within the term "variant(s)" are amino acid substitutions, additions, or deletions of GLP-2 molecules and corresponding nucleic acids encoding such variant amino acid sequences. Also encompassed within the term "variant(s)" are chemically modified natural and synthetic GLP-2 molecules.

As used herein, the term "analog(ue)" or "analog(ue)s" as used herein refers to a polypeptide that possesses similar or identical function to a GLP-2 polypeptide or a fragment of a GLP-2 polypeptide, but does not necessarily comprise a similar or identical amino acid sequence of a GLP-2 polypeptide or a fragment of a GLP-2 polypeptide, or possess a similar or identical structure to a GLP-2 polypeptide or a fragment of a GLP-2 polypeptide. A polypeptide that has a similar amino acid sequence refers to a polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a GLP-2 polypeptide or a fragment of a GLP-2 polypeptide described herein; (b) a polypeptide encoded by a nucleotide sequence that hybridizes under stringent conditions to a nucleotide sequence encoding a GLP-2 polypeptide or a fragment of a GLP-2 polypeptide described herein of at least 10 amino acid residues, at least 15 amino acid residues, at least 20 amino acid residues, at least 25 amino acid residues, or at least 30 amino acid residues; and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a GLP-2 polypeptide or a fragment of a GLP-2 polypeptide described herein. A polypeptide with similar structure to a GLP-2 polypeptide or a fragment of a GLP-2 polypeptide described herein refers to a polypeptide that has a similar secondary, tertiary or quaternary structure of a GLP-2 polypeptide or a fragment of a GLP-2 polypeptide described herein. The structure of a polypeptide can determined using methods known to those skilled in the art, including but not limited to, X-ray crystallography, nuclear magnetic resonance, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). Optionally, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (e.g., http://www.ncbi.nlm.nih.gov). Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

Among the analogues or variants of GLP-2 contemplated herein are fragments of a GLP-2. As used herein, the term "fragment" or "fragments" as used herein refers to a peptide or polypeptide having an amino acid sequence of at least 10 contiguous amino acid residues, at least 15 contiguous amino acid residues, at least 20 contiguous amino acid residues, at least 25 contiguous amino acid residues, or at least 30 contiguous amino acid residues of the amino acid sequence of a GLP-2 polypeptide.

The term 'mimic' used herein includes molecules that are not peptides but which have the ability to bind specifically to the GLP-2 binding site of a GLP-2 receptor, particularly one on an osteoclast, including compounds that produce activation of said receptor on so binding. Activation of the receptor implies the production by the receptor of a functional response akin to that produced on binding its native GLP-2, whether in nature, intensity, or both.

The term 'derivative' used herein in respect of derivatives of GLP-2, or a variant or analog thereof, refers to a molecule having a peptide structure but modified to include a non-peptide moiety.

As used herein, the phrase "GLP-2 activator" or "GLP-2 activators" refers to any molecule or compound that increases the activity of GLP-2 in a patient. The invention encompasses, e.g., GLP-2 agonists, GLP-2 receptor agonists, agonists of the GLP-2 signal transduction cascade, compounds that stimulate the synthesis or expression of endogenous GLP-2, compounds that stimulate release of endogenous GLP-2, and compounds that inhibit inhibitors of GLP-2 activity (i.e., an inhibitor of a GLP-2 antagonist).

As used herein, the term "patient" is an animal, such as, but not limited to, a cow, monkey, horse, sheep, pig, chicken, turkey, quail, cat, dog, mouse, rat, rabbit, and guinea pig, and is more preferably a mammal, and most preferably a human.

As used herein, the phrase "therapy" or "therapeutic agent" refers to any molecule, compound, or treatment that assists in the treatment of a disease, especially a bone-related disorder or calcium homeostasis related syndrome. As such, therapy includes, but is not limited to, radiation therapy, chemotherapy, dietary therapy, physical therapy, and psychological therapy.

As used herein, the phrase "bone-related disorder" refers to a disorder wherein bone formation, deposition, or resorption is abnormal, especially where this leads to a loss of bone mass over time. Bone-related disorders include, but are not limited to, osteoporosis, hypercalcemia of malignancy, osteopenia due to bone metastases, periodontal disease, hyperparathyroidism, periarticular erosions in rheumatoid arthritis, Paget's disease, osteodystrophy, myositis ossificans, Bechterew's disease, malignant hypercalcemia, osteolytic lesions produced by bone metastasis, bone loss due to immobilization, bone loss due to sex steroid hormone deficiency, bone abnormalities due to steroid hormone treatment, bone abnormalities caused by cancer therapeutics, osteomalacia, osteomalacia, hyperostosis, osteopetrosis, metastatic bone disease, immobilization-induced osteopenia, and glucocorticoid-induced osteoporosis.

As used herein, the phrase "calcium homeostasis related syndrome" refers to a condition wherein calcium homeostasis is abnormal, especially where this leads to hypercalcaemia. Calcium homeostasis related syndromes include, but are not limited to, hypercalcemia of malignancy, hyperparathyroidism, malignant hypercalcemia, PTH induced hypercalcaemia.

As used herein, the phrase "pharmaceutically acceptable" refers to an agent that does not interfere with the effectiveness of the biological activity of an active ingredient, and which may be approved by a regulatory agency of the Federal government or a state government, or is listed in the U.S. Pharmacopeia or other generally recognized pharmacopeia for use in animals, and more particularly for use in humans. Accordingly, suitable pharmaceutically acceptable carriers include agents that do not interfere with the effectiveness of a pharmaceutical composition.

As used herein, the phrase "pharmaceutically acceptable salts" refers to salts prepared from pharmaceutically acceptable, preferably nontoxic, acids and bases, including inorganic and organic acids and bases, including but not limited to, sulfuric, citric, maleic, acetic, oxalic, hydrochloride, hydro bromide, hydro iodide, nitrate, sulfate, bisulfite, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Pharmaceutically acceptable salts include those formed with free amino groups such as, but not limited to, those derived from hydrochloric, phosphoric, acetic, oxalic, and tartaric acids. Pharmaceutically acceptable salts also include those formed with free carboxyl groups such as, but not limited to, those derived from sodium, potassium, ammonium, sodium lithium, calcium, ferric hydroxides, isopropylamine, triethylamine, 2-ethylamino ethanol, histidine, and procaine.

As used herein, the term "carrier" refers to a diluent, adjuvant, excipient, or vehicle. Such carriers can be sterile liquids, such as saline solutions in water, or oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions.

As used herein, the tern "mineral" refers to a substance, preferably a natural substance, that contain calcium, magnesium or phosphorus. Illustrative nutrients and minerals include beef bone, fish bone, calcium phosphate, egg shells, sea shells, oyster shells, calcium carbonate, calcium chloride, calcium lactate, calcium gluconate and calcium citrate.

As used herein, the term "biological sample" is broadly defined to include any cell, tissue, organ or multicellular organism. A biological sample can be derived, for example, from cells or tissue cultures in vitro. Alternatively, a biological sample can be derived from a living organism or from a population of single cell organisms. Preferably, the biological sample is live tissue. More preferably, the biological sample is live bone or adipose tissue.

As used herein, the term "GIP" refers to glucose-dependent insulinotropic polypeptide. GIP is an incretin that stimulates insulin secretion directly in a glucose-dependent manner.

As used herein, the term "S-CTX" refers to a serum C-telopeptide fragment of collagen type I degradation.

As used herein, the phrase "isolated polypeptide or peptide" refers to a polypeptide or peptide that is substantially free of cellular material or other contaminating proteins from the cell or tissue source from which the protein is derived, or substantially free of chemical precursors or other chemicals when chemically synthesized. The language "substantially free of cellular material" includes preparations of peptide, polypeptide, or protein in which the peptide, polypeptide, or protein is separated from cellular components of the cells from which it is isolated or recombinantly produced. Thus, peptide, polypeptide, or protein that is substantially free of cellular material includes preparations having less than about 30%, 20%, 10%, or 5% (by dry weight) of heterologous proteinaceous material (also referred to herein as a "contaminating protein"). When the protein, peptide, polypeptide, or fragment thereof is recombinantly produced, it is also preferably substantially free of culture medium, i.e., culture medium represents less than about 20%, 10%, or 5% of the volume of the preparation. When the material is produced by chemical synthesis, it is preferably substantially free of chemical precursors or other chemicals, i.e., it is separated from chemical precursors or other chemicals which are involved in the synthesis of the protein. Accordingly such preparations have less than about 30%, 20%, 10%, 5% (by dry weight) of chemical precursors or compounds other than the peptide, polypeptide, or protein of interest. In preferred embodiments, purified or isolated preparations will lack any contaminating proteins from the same animal from which the protein is normally produced, as can be accomplished by recombinant expression of, for example, a human protein in a non-human cell.

As used herein, the phrase "isolated nucleic acid molecule" refers to a nucleic acid molecule which is separated from other nucleic acid molecules which are present in the natural source of the nucleic acid molecule. Preferably, an isolated nucleic acid molecule is free of sequences (preferably protein encoding sequences) which naturally flank the nucleic acid (i.e., sequences located at the 5' and 3' ends of the nucleic acid) in the genomic DNA of the organism from which the nucleic acid is derived. In other embodiments, the isolated nucleic acid is free of intron sequences. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an isolated nucleic acid molecule, such as a cDNA molecule, can be substantially free of other cellular material, or culture medium when produced by recombinant techniques, or substantially free of chemical precursors or other chemicals when chemically synthesized. In one embodiment, the nucleic acid molecules of the invention comprise a contiguous open reading frame encoding a polypeptide of the invention.

As used herein, the phrase "hybridizes under stringent conditions" is intended to describe conditions for hybridization and washing under which nucleotide sequences at least 60% (65%, 70%, 75%, 80%, or preferably 85% or more) identical to each other typically remain hybridized to each other. Such stringent conditions are known to those skilled in the art and can be found in *Current Protocols in*

*Molecular Biology*, John Wiley & Sons, N.Y. (1989), 6.3.1-6.3.6, which describes aqueous and non-aqueous methods, either of which can be used. Another preferred, non-limiting example of stringent hybridization conditions are hybridization in 6× sodium chloride/sodium citrate (SSC) at about 45° C., followed by one or more washes in 2.0×SSC at 50° C. (low stringency) or 0.2×SSC, 0.1% SDS at 50-65 ° C. (high stringency). Another preferred example of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions are hybridization in 6× sodium chloride/sodium citrate (SSC) at about 45° C., followed by one or more washes in 0.2×SSC, 0.1% SDS at 60° C. Preferably, stringent hybridization conditions are hybridization in 6× sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. In one embodiment, an isolated nucleic acid molecule of the invention that hybridizes under stringent conditions to the sequence of the GLP-2 nucleic acid, or a complement thereof, corresponds to a naturally-occurring nucleic acid molecule. As used herein, a "naturally occurring" nucleic acid molecule refers to an RNA or DNA molecule having a nucleotide sequence that occurs in nature (e.g., encoding a natural protein).

4. BRIEF DESCRIPTION OF THE DRAWINGS

5. DETAILED DESCRIPTION OF THE INVENTION

Figure 1A:
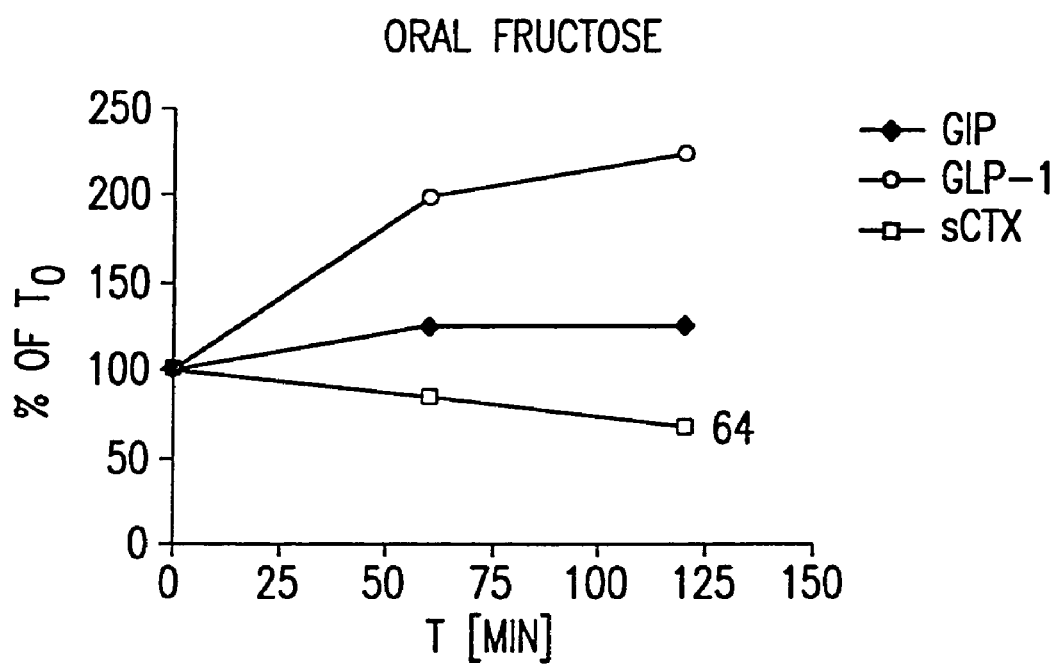
FIGS. 1A, 1B and 1C show the levels of GLP-1 (as a surrogate marker for GLP-2), GIP and S-CTX over a 2-3 hour period in response to (A) oral fructose; (B) oral long chain fatty acid; (C) oral protein.

5.1 GLP-2 and bone-related Disorders and Calcium Homeostasis Related syndromes.

The present invention is based, in part, on Applicant's discovery that GLP-2 inhibits bone resorption and promotes bone formation. Without being bound by any theory, Applicant believes that GLP-2 exerts an anti-resorptive effect, particularly by acting to activate GLP-2 receptors present on osteoclasts serving as a signal to reduce resorption of bone by the osteoclasts. Stimulation of these cells with GLP-2 can lead to an increase in intracellular calcium concentration, an increase in cellular cAMP content, a stimulation of type I collagen synthesis, and inhibition of PTH-stimulated bone resorption.

Therefore, GLP-2 molecules and GLP-2 activators disclosed herein are useful for treating or preventing a bone-related disorder, including a bone-related disorder disclosed herein.

In accordance with the invention, the present compositions and methods can be used to intercede upstream or downstream in the signal transduction cascade involved in GLP-2 action to reduce the rate of bone resorption and/or to promote the rate of bone formation. In one embodiment, the synthesis or release of endogenous GLP-2 can be stimulated. In another embodiment, the endogenous synthesis or release of another molecule active in the cascade downstream from GLP-2, (e.g., a molecule produced in response to GLP-2 binding to a receptor), can be stimulated.

Accordingly, the methods and compositions of the invention are useful for preventing, treating, diagnosing, or monitoring the progression a bone-related disorder or a calcium homeostasis related syndrome, including a bone-related disorder and a calcium homeostasis related syndrome disclosed herein.

5.2 GLP-2 Molecules

The GLP-2 molecules can be used in the present methods and compositions for treating or preventing a bone-related disorder.

In one embodiment, the GLP-2 molecule may be produced by in vivo expression of a GLP-2 nucleic acid encoding a GLP-2 polypeptide, peptide, or fragment thereof. The GLP-2 nucleic acid is, for example, a full-length cDNA, cDNA corresponding to a protein coding region, RNA, mRNA, oligonucleotide, consensus sequence, motif, restriction fragment, antisense molecule, ribozyme, or a molecule encoding a protein domain.

As described in Irwin and Wong, Molecular Endocrinology, 1995, Vol 9, No. 3, 267-276, GLP-2 peptides are known from fish, amphibians, birds and mammals and GLP-2 is thought to be universal in vertebrates. In mammals, GLP-2 is expressed in the brain stem, the pancreas and the intestine as part of the sequence of the precursor peptide proglucagon. Proglucagon is processable by proteolytic cleavage in a tissue specific manner to yield GLP-1 and GLP-2 in the brain and intestine. Glucagon is only produced in the pancreas. The sequence of GLP-2 in humans is:

```
HADGSFSDEMNTILDNLAARDFINWLIQTKITD(R)(K)
``` where (R) and (K) are additional amino acids coded for in the gene sequence which may also be present in extended forms of the peptide occurring in the body.

Other mammalian GLP-2s are highly conserved and are very close in sequence to the human form. Sequences for GLP-2 from the degu, guinea pig, hamster, rat and cow are given in Nishi and Steiner, Molecular Endocrinology, 1990, Vol 4, No. 8, 1192-1198, and are as set out below:

```
Degu:       HADGSFSDEMNTVLDHLATKDFINWLIQTKITD(R)(K)
Guinea pig: HADGSFSDEMNTILDNLATRDFINWLIQTKITD(R)(K)
Hamster:    HADGSFSDEMNTILDSLATRDFINWLIQTKITD(K)(K)
Rat:        HADGSFSDEMNTILDNLATRDFINWLIQTKITD(K)(K)
Bovine:     HADGSFSDEMNTVLDSLATRDFINWLLQTKITD(R)(K)
Human:      HADGSFSDEMNTILDNLAARDFINWLIQTKITD(R)(K)
```

Typically, the GLP-2 molecule is a GLP-2 polypeptide or peptide, or fragment thereof. The GLP-2 polypeptide or peptide is, for example, a full-length protein, receptor binding domain, catalytic domain, signal sequence, or protein motif.

Moreover, any GLP-2 variant that, compared to a natural GLP-2, contains additional amino acid residues, or has amino acids deleted from it but retains therapeutic functionality can be used in the present methods and compositions of the invention. Additionally, GLP-2 molecules of the invention may contain substituted amino acids, including both natural an unnatural amino acids. In one embodiment, the GLP-2 variant has enhanced activity compared to native human GLP-2. For example, such GLP-2 variants can exhibit enhanced serum stability, enhanced receptor binding, or enhanced signal transducing activity. Amino acid modifications, substitutions, additions, or truncations that render a GLP-2 peptide resistant to oxidation or degradation are contemplated by the present invention. In a preferred embodiment, the GLP-2 variants are derived from human or rat GLP-2 sequences.

Many molecules contemplated as GLP-2 variants, in accordance with the present invention are known in the art. For example, U.S. Pat. No. 5,990,077, discloses forms of GLP-2 and the pharmaceutically acceptable acid salts thereof, that conform to the general formula:

R1-[Y]m-His-Ala-Asp-Gly-Ser-Phe-Ser-Asp-Glu-Met-

Asn-Thr-aa1-Leu-Ala-aa2-Leu-Ala-aa3-Arg-Asp-Phe-

Ile-Asn-Trp-Leu-aa4-aa5-Thr-Lys-Ile-Thr-Asp-[X]- n-R2.

GLP-2 and suitable variants, analogues, derivatives and mimics act as agents affecting bone tissue metabolism. The degradation of bone is markedly reduced when measured by the S-CTX bone degradation markers in serum samples following administration of GLP-2 or the stimulation of endogenous GLP-2 release. It is accordingly a general object of the present invention to exploit GLP-2 variants, analogues, derivatives and mimics for the use in treatment of bone related diseases.

Thus, in another embodiment, the GLP-2 molecule is a GLP-2 variant. GLP-2 variants are known in the art. Examples of GLP-2 variants are found in U.S. Pat. Nos. 5,990,077 and 6,184,201, and include the following:

1) His-Ala-Asp-Gly-Ser-Phe-Ser-Asp-Glu-Met-Asn-

Thr-Ile-Leu-Asp-Asn-Leu-Ala-Thr-Arg-Asp-Phe-

Ile-Asn-Trp-Leu-Ile-Gln-Thr-Lys-Ile-Thr-Asp.

2) R1-[Y]m-His-Ala-Asp-Gly-Ser-Phe-Ser-Asp-Glu-

Met-Asn-Thr-aa1-Leu-Asp-aa2-Leu-Ala-aa3-Arg-

Asp-Phe-Ile-Asn-Trp-Leu-aa4-aa5-Thr-Lys-Ile-

Thr-Asp-[X]n-R2.

wherein:
  aa1 is a neutral, polar, large and nonaromatic amino acid residue;
  aa2 is a neutral and polar amino acid residue;
  aa3 is a neutral amino acid residue;
  aa4 is a neutral, polar, large and nonaromatic amino acid residue;
  aa5 is a neutral or basic amino acid residue;
X is Arg, Lys, Arg-Lys or Lys-Lys;
Y is Arg or Arg-Arg;
m is 1 or 1;
n is 0 or 1;
R1 is H or an N-terminal blocking group; and
R2 is OH or a C-terminal blocking group.

3) R1-[Y]m-His-Ala-Asp-Gly-Ser-Phe-Ser-Asp-Glu-

Met-Asn-Thr-aa1-Leu-Asp-aa2-Leu-Ala-aa3-Arg-

Asp-Phe-Ile-Asn-Trp-Leu-aa4-aa5-Thr-Lys-Ile-

Thr-Asp-[X]n-R2 wherein:
  aa1 is Ile or Val;
  aa2 is Asn or Ser;
  aa3 is Ala or Thr;
  aa4 is Ile or Leu;
  aa5 is Gln or His;
X is Arg, Lys, Arg-Lys or Lys-Lys;
Y is Arg or Arg-Arg;
m is 0 or 1;
n is 0 or 1;
R1 is H or an N-terminal blocking group; and
R2 is OH or a C-terminal blocking group.

4) R1-(Y1)m-X1-X2-X3-X4-Ser5-Phe6-Ser7-Asp8-(P1)-

Leu14-Asp15-Asn16-Leu17-Ala18-X19-X20-Asp21-

Phe22-(P2)-Trp25-Leu26-Ile27-Gln28-Thr29-Lys30-

(P3)-(Y2)n-R2, wherein
  X1 is His or Tyr
  X2 is Ala or an Ala-replacement amino acid conferring on said analog resistance to DPP-IV enzyme;
  X3 is Pro, HPro, Asp or Glu;
  X4 is Gly or Ala;
  P1 is Glu-X10-Asn-Thr-Ile or Tyr-Ser-Lys-Tyr;
  X10 is Met or an oxidatively stable Met-replacement amino acid;
  X19 is Ala or Thr;
  X20 is Arg, Lys, His or Ala;
  P2 is Ile-Asn, Ile-Ala or Val-Gln;
  P3 is a covalent bond, or is Ile, Ile-Thr or Ile-Thr-Asn;
  R1 is H or an N-terminal blocking group;
  R2 is OH or a C-terminal blocking group;
  Y1 is one or two basic amino acids selected from the group Arg, Lys, and His;
  Y2 is one or two basic amino acids selected from the group Arg, Lys, and His; and
  m and n, independently, are 0 or 1; and wherein at least one of X1, X2, X3, X4, P1, X10, X19, X20, P2 and P3 is other than a wild type, mammalian GLP-2 residue. These and other GLP-2 variants may be employed in the invention.

According to one aspect of the invention, there is provided a GLP-2 analogue in a pharmaceutically acceptable form that is suitable for formulation and subsequent administration to patients. In another of its aspects, the invention provides a pharmaceutical composition comprising GLP-2 analogues and a pharmaceutically acceptable carrier. In a further aspect, the invention provides a method for inhibition of bone degradation in a patient in need thereof, comprising the step of delivering to the patient a bone degradation inhibiting amount of GLP-2 analogues. Thus in this aspect the present invention relates to the therapeutic uses of GLP-2 analogues for treating, alleviating or preventing various medical conditions relating to the bone tissue. Particularly, the invention relates to the use of GLP-2 analogues for the inhibition of bone degradation more particularly known as osteoporosis.

Unless otherwise specified, the term GLP-2 analogues refers collectively herein to the various synthetically or recombinantly produced forms of GLP-2, particularly the mammalian forms, e.g., rat GLP2, ox GLP-2, porcine GLP-2, bovine GLP-2, guinea pig GLP-2, hamster GLP-2 and human GLP-2, the sequences of which have been reported by many authors including Buhl et al in J. Biol. Chem., 1988, 263(18):8621. Taking into account the significant sequence homology among these GLP-2 species, the present invention embraces the use as a inhibitor of bone tissue degradation of those forms of GLP-2 and the pharmaceutically acceptable acid salts thereof, that conform to the general formula represented below:

R1-(Y1)m-X1-X2-X3-X4-X5-X6-X7-X8-X9-X10-X11-X12-

X13-X14-X15-X16-X17-X18-X19-X20-X21-X22-X23-X24-

X25-X26-X27-X28-X29-X30-X31-X32-X33-(Y2)n-R2 wherein:
R1 is H or an N-terminal blocking group;
(Y1) is one or two basic amino acids selected from the group Arg, Lys, and His;
X1 is X0, His or Tyr;
X2 is X0, Ala, Leu, Cys, Glu, Arg, Trp, Tyr, DhPr, D-Pro, D-Ala, Gly, Val, Lys, Ile, Trp, $PO_3$-Tyr, Cys, or an Ala-replacement amino acid which confers on the analog or salt resistance to cleavage by human DPP-IV enzyme; (preferably X2 is X0, Ala, Leu, Cys, Glu, Arg, Trp, Tyr, or an Ala-replacement amino acid which confers on the analog or salt resistance to cleavage by human DPP-IV enzyme;)
X3 is X0, Pro, HPro, Asp or Glu;
X4 is X0, Gly or Ala;
X5 is Ser or Xd;
X6 is Phe;
X7 is Ser or Xd;
X8 is Asp;
X9 is Glu or Tyr;
X10 is Met or oxidisable stable Met analogue, Val, Ile, Asn, Glu, Gln, Tyr, Phe, Leu, Nle, Ala, Gly, or Ser; (preferably X10 is Met or oxidisable stable Met analogue, or Ser;)
X11 is Asn or Lys;
X12 is Thr or Tyr;
X13 is Ile, Val or a neutral, polar, large and nonaromatic amino acid residue;
X14 is Leu;
X15 is Asp or Xa;
X16 is Asn, Ser or a neutral and polar amino acid residue;
X17 is Leu;
X18 is Ala;
X19 is Ala, Thr or a neutral amino acid residue;
X20 is Arg, Lys, His or Ala;
X21 is Asp;
X22 is Phe or Xb;
X23 is Ile or Val;
X24 is Asn, Gln or Ala;
X25 is Trp;
X26 is Leu;
X27 is Ile, Leu or a neutral, polar, large and nonaromatic amino acid residue;
X28 is Gln, His or a neutral or basic amino acid residue;
X29 is Thr or Xc;
X30 is Lys;
X31 is Ile or Arg;
X32 is Thr, Lys or Xc;
X33 is Asp, Asn, His or Xa;
X0 is an amino acid deletion,
Xa is any amino acid other than Asp;
Xb is any amino acid other than Phe;
Xc is any aminoacid other than Thr;
Xd is any amino acid other than Ser;
Y2 is one or two basic amino acids selected from the group Arg, Lys, and His;
m and n are independently 0 or 1 and wherein at least one of X1-X2-X3-X4-X5-X6-X7-X8-X9-X10-X11-X12-X13-X14-X15-X16-X17-X18-X19-X20-X21-X22-X23-X24-X25-X26-X27-X28-X29-X30-X31-X32-X33 is other than wild type, mammalian GLP-2 residue, and
R2 is OH or a C-terminal blocking group.

In particular embodiments of the invention, the GLP-2 conforms to the sequence shown below:

R1-[Y1]-His-Ala-Asp-Gly-Ser-Phe-Ser-Asp-Glu-Met-

Asn-Thr-Ile-Leu-Asp-Asn-Leu-Ala-X19-Arg-Asp-Phe-

Ile-Asn-Trp-Leu-Ile-Gln-Thr-Lys-Ile-Thr-Asp-[Y2]n-

R2 wherein X19, Y1, Y2, n, R1 and R2 are as defined above

In a specific embodiment of the invention, GLP-2 has the sequence illustrated below:

His-Ala-Asp-Gly-Ser-Phe-Ser-Asp-Glu-Met-Asn-Thr-

Ile-Leu-Asp-Asn-Leu-Ala-Thr-Arg-Asp-Phe-Ile-Asn-

Trp-Leu-Ile-Gln-Thr-Lys-Ile-Thr-Asp,

In another embodiment, the invention relates to a method wherein said medical conditions relates to diseases characterized by bone tissue degradation.

In a preferred embodiment, the invention relates to method wherein said diseases are osteoporosis and osteolytic bone metastasis.

In another preferred embodiment, the invention relates to a pharmaceutical composition wherein the GLP-2 or variant, analogue, derivative, or mimic is present in an amount effective to promote the reduction in bone tissue degradation.

In yet another preferred embodiment, the invention relates to a method for treating, alleviating or preventing osteoporosis and osteolytic bone metastasis in a patient suffering thereof, comprising the step of administering to the patient an effective amount of a pharmaceutical composition to inhibit the degradation of bone tissue.

In a most preferred embodiment, the invention relates to a method wherein the patient is a human patient.

The "blocking groups" represented by R1 and R2 are chemical groups that are routinely used to confer biochemical stability and resistance to digestion by exopeptidase. Suitable N-terminal protecting, groups include, for example, $C_{1-5}$ alkanoyl groups such as acetyl. Also suitable as N-terminal protecting groups are amino acid analogues lacking the amino function. Suitable C-terminal protecting groups include groups which form ketones or amides at the carbon atom of the C-terminal carboxyl, or groups which form esters at the oxygen atom of the carboxyl. Ketone and ester-forming groups include alkyl groups, particularly branched or unbranched $C_{1-5}$ alkyl groups, e.g. methyl, ethyl and propyl groups, while amide-forming groups include amino functions such as primary amine, or alkylamino functions, e.g. mono-$C_{1-5}$-alkylamino and di-$C_{1-5}$ alkylamino groups such as methylamino, ethylamino, dimethylamino, diethylamino, methylethylamino and the like. Amino acid analogues are also suitable for protecting the C-terminal end of the present compounds, for example, decarboxylated amino acid analogues such as agmatine.

The particular form of GLP-2 selected for inhibiting bone tissue degradation can be prepared by a variety of techniques well known for generating peptide products. As described by Buhl et al, supra, porcine GLP-2 isolation and purification is achieved from acid-ethanol extracts of ileal mucosa by a combination of size selection and HPLC-based fractionation, with the aid of antibody raised against synthetic proglucagon 126-159, to monitor work-up. As an alternative to GLP-2 extraction, those forms of GLP-2 that incorporate only L-amino acids can be produced reproducibly and in commercial quantities by application of recombinant DNA technology. For this purpose, DNA coding for the desired form of GLP-2 is incorporated expressibly in a microbial e.g. yeast, or other cellular host, which is then cultured under conditions appropriate for GLP-2 expression. A variety of gene expression systems have been adapted for this purpose, and typically drive expression of the desired gene from expression controls used naturally by the chosen host. Because GLP-2 does not require post translational glycosylation for its activity, its production may most conveniently be achieved in bacterial hosts such as *E. coli*. For such production, DNA coding for the selected GLP-2 may usefully be placed under expression controls of the lac, trp or PL genes of *E. coli*. As an alternative to expression of DNA coding for the GLP-2 per se, the host can be adapted to express GLP-2 as a fusion protein it which the GLP-2 is linked releasably to a carrier protein that facilitates isolation and stability of the expression product.

In an approach universally applicable to the production of a selected GLP-2, and one used necessarily to produce GLP-2 forms that incorporate non-genetically encoded amino acids and N- and C-terminally derivatized forms, the-well established techniques of automated peptide synthesis are employed, general descriptions of which appear, for example, in J. M. Stewart and J. D. Young, Solid Phase Peptide Synthesis, 2nd Edition, 1984, Pierce Chemical Company, Rockford, Ill.; and in M. Bodanszky and A. Bodanszky, The Practice of Peptide Synthesis, 1984, Springer-Verlag, New York; Applied Biosystems 430A Users Manual, 1987, ABI Inc., Foster City, Calif. In these techniques, the GLP-2 is grown from its C-terminal, resin-conjugated residue by the sequential addition of appropriately protected amino acids, using either the Fmoc or tBoc protocols, as described for instance by Orskov et al, 1989, supra.

For the incorporation of N- and/or C-protecting groups protocols is conventional to solid phase peptide synthesis methods can also be applied. For incorporation of C-terminal protecting groups, for example, synthesis of the desired peptide is typically performed using, as solid phase, a supporting resin that has been chemically modified so that cleavage from the resin results in a peptide having the desired C-terminal protecting group. To provide peptides in which the C-terminus bears a primary amino protecting group, for instance, synthesis is performed using a p-methylbenzhydrylamine, (MBHA) resin so that, when peptide synthesis is completed, treatment with hydrofluoric acid releases the desired C-terminally amidated peptide. Similarly, incorporation of an N-methylamine protecting group at the C-terminus is achieved using N methylaminoethyl-derivatized DVB resin, which upon HF treatment releases peptide bearing an N-methylamidated C-terminus. Protection of the C-terminus by esterification can also be achieved using conventional procedures. This entails use of resin/blocking group combination that permits release of side-chain protected peptide from the resin, to allow for subsequent reaction with the desired alcohol, to form the ester function. FMOC protecting groups, in combination with DVB resin derivatised with methoxyalkoxybenzyl alcohol or equivalent linker, can be used for this purpose, with cleavage from the support being effected by TFA in dichloromethane. Esterification of the suitably activated carboxyl function e.g. with DCC, can then proceed by addition of the desired alcohol, followed by deprotection and isolation of the esterified peptide product.

Incorporation of N-terminal protecting groups can be achieved while the synthesized peptide is still attached to the resin, for instance by treatment with suitable anhydride and nitrile. To incorporate an acetyl protecting group at the N-terminus, for instance, the resin-coupled peptide can be treated with 20% acetic anhydride in acetonitrile. The N-protected peptide product can then be cleaved from the resin, deprotected and subsequently isolated.

Once the desired peptide sequence has been synthesized, cleaved from the resin and fully deprotected, the peptide is then purified to ensure the recovery of a single oligopeptide having the selected amino acid sequence, Purification can be achieved using any of the standard approaches, which include reversed-phase high-pressure liquid chromatography (RP-HPLC) on alkylated silica columns, e.g. $C_4$-, $C_8$-, or $C_{18}$ alkylated silica. Such column fractionation is generally accomplished by running linear gradients, e.g. 10-90%, of increasing % organic solvent, e.g. acetonitrile, in aqueous buffer, usually containing a small amount (e.g. 0.1%) of pairing agent such as TFA or TEA. Alternatively, ion-exchange HPLC can be employed to separate peptide species on the basis of their charge characteristics. Column fractions are collected, and those containing peptide of the desired/required purity are optionally pooled. In one embodiment of the invention, the peptide is then treated in the established manner to exchange the cleavage acid (e.g. TFA) with a pharmaceutically acceptable acid, such as acetic, hydrochloric, phosphoric, maleic, tartaric, succinic and the likes to provide a water soluble salt of the peptide.

For administration to patients, the GLP-2 is provided, in one aspect of the invention, in pharmaceutically acceptable form, e.g., as a preparation that is sterile-filtered e.g. through a 0.22 µm filter, and substantially pyrogen-free. Desirably, the GLP-2 to be formulated migrates as a single or individualized peak on HPLC, exhibits uniform and authentic amino acid composition and sequence upon analysis thereof, and otherwise meets standards set by the various national bodies which regulate quality of pharmaceutical products.

For therapeutic use, the chosen GLP-2 is formulated with a carrier that is pharmaceutically acceptable and is appropriate for delivering the peptide by the chosen route of administration. Suitable pharmaceutically acceptable carriers are those used conventionally with peptide-based drugs, such as diluents, excipients and the like. Reference may be made to "Remington s Pharmaceutical Sciences", 17th Ed., Mack Publishing Company, Easton, Pa., 1995, for guidance on drug formulations generally. In one embodiment of the invention the compounds are formulated for administration by infusion or by injection, either sub-cutaneously or intravenously, and are accordingly utilized as aqueous solutions in sterile and pyrogen-free form and optionally buffered to a slightly acidic or physiological pH. Thus, the compounds may be administered in distilled water or, more desirably, in saline, buffered saline or 5% dextrose solution. Water solubility of these and other the GLP-2 may be enhanced, if desired, by incorporating a solubility enhancer, such as acetic acid.

For use in inhibiting the degeneration of bone tissue in a mammal including a human, the present invention provides in one of its aspects a package, in the form of a sterile-filled vial or ampoule, that contains a bone tissue degradation inhibiting amount of the GLP-2 or analogue etc., in either unit dose or multi-dose amounts, wherein the package incorporates a label instructing use of its contents for the inhibition of bone tissue degeneration. In one embodiment of the invention, the package contains the GLP-2 and the desired carrier, as an administration-ready formulation. Alternatively, and according to another embodiment of the invention, the package provides the GLP-2 in a form, such as a lyophilized form, suitable for reconstitution in a suitable carrier, such as buffered saline.

In one embodiment, the package is a sterile-filled vial or ampoule containing an injectable solution which comprises an effective amount of GLP-2 dissolved in an aqueous vehicle.

As an alternative to injectable formulations, the GLP-2 may be formulated for administration by other routes. Oral dosage forms, such as tablets, capsules and the like, can be formulated in accordance with standard pharmaceutical practice.

In one embodiment, the GLP-2 variant is resistant to cleavage by dipeptidyl peptidase-IV (DPP-IV).

In another embodiment, the GLP-2 variant has an amino acid sequence wherein an oxidatively sensitive amino acid, is replaced with an oxidatively stable amino acid residue. In another embodiment, the oxidatively sensitive amino acid is methionine ("Met"). These variants can be more stable than a native GLP-2.

In another embodiment, the GLP-2 variant has an amino acid sequence wherein an arginine is replaced with a basic amino acid (e.g., histidine or lysine).

5.3 GLP-2 Activators

The invention also encompasses molecules that serve to increase GLP-2 activity (GLP-2 activators) for use in prevention and treatment of bone-related disorders and calcium homeostasis related syndromes. For example, GLP-2 agonists, GLP-2 receptor agonists, agonists of the GLP-2 signal transduction cascade, compounds that stimulate the synthesis or expression of endogenous GLP-2, compounds that stimulate release of endogenous GLP-2, and compounds that inhibit inhibitors of GLP-2 activity (i.e., an inhibitor of a GLP-2 antagonist) are contemplated.

In one embodiment, the GLP-2 activator is a GLP-2 agonist. GLP-2 agonists are known in the art and are listed below (See also, e.g., U.S. Pat. No. 6,051,557).

In specific embodiments of the invention, the GLP-2 agonist comprises an amino acid having the sequence:

His-Ala-Asp-Gly-Ser-Phe-Ser-Asp-Glu-Met-Asn-Thr-
Ile-Leu-Asp-Asn-Leu-Ala-Thr-Arg-Asp-Phe-Ile-Asn-
Trp-Leu-Ile-Gln-Thr-Lys-Ile-Thr-Asp;
or

His-Ala-Asp-Gly-Ser-Phe-Ser-Asp-Glu-Met-Asn-Thr-
Ile-Leu-Asp-Asn-Leu-Ala-Ala-Arg-Asp-Phe-Ile-Asn-
Trp-Leu-Ile-Gln-Thr-Lys-Ile-Thr-Asp;
or

His-Gly-Asp-Gly-Ser-Phe-Ser-Asp-Glu-Met-Asn-Thr-
Ile-Leu-Asp-Asn-Leu-Ala-Ala-Arg-Asp-Phe-Ile-Asn-
Trp-Leu-Ile-Gln-Thr-Lys-Ile-Thr-Asp.

In a particular embodiment, GLP-2 agonists have a(n):
N-terminal blocking group; and/or
N-terminal extension such as Arg or Arg-Arg; and/or
C-terminal blocking group; and/or
C-terminal extension such as Arg or Arg-Arg.

In another embodiment, the GLP-2 molecule useful for the invention is an inhibitor of a GLP-2 antagonist. In a particular embodiment, the GLP-2 antagonist is a protease. In a specific embodiment, the protease is DPP-IV.

Useful inhibitors of the GLP-2 antagonist, DPP-IV, include, but are not limited to, N-(substituted glycyl)-2-cyanopyrrolidines, valine-pyrrolidide, N-Ala-Pro-O-(nitrobenzyl-)hydroxylamine, and ε-(4-nitro) benzoxycarbonyl-Lys-Pro. Other useful inhibitors of DPP-IV are known in the art (See, e.g., U.S. Pat. No. 5,462,928 (columns 2-4), U.S. Pat. No. 5,543,396 (column 2) and U.S. Pat. No. 6,124,305 (columns 1-2). Some examples are: X-Pro-Y-boroPro, where X and Y are chosen from any amino acid residue, and where boroPro is used to designate an α-amino boronic acid analog of proline which has the carboxyl group of proline replaced with a B(OH)$_2$ group; peptidyl derivatives of aromatic diesters of α-aminoalkylphosphonic acids; and N-(substituted glycyl)-2-cyanopyrrolidines.

In yet another embodiment, the inhibitor of a GLP-2 antagonist is an antibody directed against a GLP-2 antagonist. In a further embodiment, the inhibitor is an antibody directed against DPP-IV (See, e.g., U.S. Pat. No. 6,265,551). For example, U.S. Pat. No. 6,265,551 discloses antibodies that bind specifically to the 175 kDa form of DPPIV/CD26 but not to the 105 kDa form.

Also encompassed by the invention are nucleic acid molecules encoding GLP-2 activators that are polypeptides. The nucleic acid is preferably found in a mammalian expression vector comprising a tumor-specific, tissue-specific, and/or inducible transcriptional regulatory sequence.

5.3.1 Screening Assays to Identify GLP-2 Activators

The invention provides a method (also referred to herein as a "screening assay") for identifying GLP-2 activators from candidate or test compounds or agents (e.g., peptides, peptidomimetics, small molecules or other drugs) which have a modulatory (i.e., stimulatory or inhibitory) effect on, for example, expression or activity of a GLP-2 molecule the invention.

The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al., 1993, *Proc. Natl. Acad. Sci. USA* 90:6909; Erb et al., 1994, *Proc. Natl. Acad. Sci. USA* 91:11422; Zuckermann et al., 1994,. *J Med. Chem.* 37:2678; Cho et al., 1993, *Science* 261:1303; Carrell et al., 1994, *Angew. Chem. Int. Ed. Engl.* 33:2059; Carell et al., 1994, *Angew. Chem. Int. Ed. Engl.* 33:2061; and Gallop et al., 1994, *J Med. Chem.* 37:1233.

Libraries of compounds may be presented in solution (e.g., Houghten, 1992, *Bio/Techniques* 13:412-421), or on beads (Lam, 1991, *Nature* 354:82-84), chips (Fodor, 1993, *Nature* 364:555-556), bacteria (U.S. Pat. No. 5,223,409), spores (U.S. Pat. Nos. 5,571,698; 5,403,484; and 5,223, 409), plasmids (Cull et al., 1992, *Proc. Natl. Acad. Sci. USA* 89:1865-1869) or phage (Scott and Smith, 1990, *Science* 249:386-390; Devlin, 1990, *Science* 249:404-406; Cwirla et al., 1990, *Proc. Natl. Acad. Sci. USA* 87:6378-6382; and Felici, 1991, *J Mol. Biol.* 222:301-310).

In one embodiment, an assay is a cell-based assay in which a cell that expresses a GLP-2 molecule, or a biologically active portion thereof, is contacted with a test compound and the ability of the test compound to bind to the GLP-2 molecule is determined. The cell, for example, can be a yeast cell or a cell of mammalian origin. Determining the ability of the test compound to bind to the GLP-2 molecule can be accomplished, for example, by coupling the test compound with a radioisotope or enzymatic label such that binding of the test compound to the GLP-2 molecule or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a GLP-2 molecule, or a biologically active portion thereof, with a known compound which binds the polypeptide to form an assay mixture, contacting the assay mixture with a test compound, and determining the ability of the test compound to interact with the GLP-2 molecule, wherein determining the ability of the test compound to interact with the GLP-2 molecule comprises determining the ability of the test compound to preferentially bind to the GLP-2 molecule or a biologically active portion thereof as compared to the known compound.

An example of this is as follows. Human osteoclasts can be cultured. A CD 14+ isolation is performed as previously described (Karsdal M A, Hjorth P, Henriksen K, Kirkegaard T, Nielsen K L, Lou H, Delaisse J M, Foged N T Transforming growth factor-beta controls human osteoclastogenesis through the p38 MAPK and regulation of RANK expression. J Biol Chem 2003; 278:44975-44987. ). Briefly, the monocytes are isolated from peripheral blood by centrifugation on a Ficoll-Paque gradient (Amersham Pharmacia), and the magnetically cell sorted using a CD 14+ magnetic bead isolation kit (Dynabeads M450, Dynal Biotech). The cells are then seeded in 75 cm2 flasks, and cultured in ÎMEM containing 10% serum, 100 units/mL Penicillin, 100 Âμg/mL Streptomycin and 25 ng/ml of M-CSF (R&D Systems) for three days, whereafter they are lifted and reseeded on bovine bone slices and cultured until day 14 in the presence of 25 ng/ml M-CSF and 25 ng/ml RANKL (R&D Systems) at which time large multinuclear resorbing osteoclasts are present.

At day 14, conditioned medium is harvested and fresh conditioned media containing a GLP-2 agonist can be added. After 24 hours the cell culture medium is removed and fresh conditioned medium without a GLP-2 agonist is added and cells are cultured for a further 24 hours. After the culture period, measurement of C-terminal type I collagen fragments (CTX) released from the bone slices is performed by the CrossLaps for culture ELISA kit (Nordic Bioscience Diagnostics), which is used according to the manufactures instructions. The level of CTX release during the incubation period with a GLP-2 agonist from each individual well is correlated to the basal level measured at day 14.

In another embodiment, the assay involves assessment of an activity characteristic of the GLP-2 molecule, wherein binding of the test compound with the GLP-2 molecule or a biologically active portion thereof alters (e.g., increases or decreases) the activity of the GLP-2 molecule.

In another embodiment, an assay is a cell-based assay comprising contacting a cell expressing a GLP-2 molecule, or a biologically active portion thereof, with a test compound and determining the ability of the test compound to modulate (e.g., stimulate or inhibit) the activity of the GLP-2 molecule or biologically active portion thereof. Determining the ability of the test compound to modulate the activity of the GLP-2 molecule or a biologically active portion thereof can be accomplished, for example, by determining the ability of the GLP-2 molecule to bind to or interact with a target molecule.

Determining the ability of a GLP-2 molecule to bind to or interact with a target molecule can be accomplished by one of the methods described above for determining direct binding. As used herein, a "target molecule" is a molecule with which a selected GLP-2 molecule binds or interacts with in nature. For example, a target molecule can be a component of a signal transduction pathway which facilitates transduction of an extracellular signal through the cell membrane and into the cell or a second intercellular protein which has catalytic activity or a protein which facilitates the association of downstream signaling molecules with a GLP-2 molecule. Determining the ability of a GLP-2 molecule to bind to or interact with a target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a regulatory element that is responsive to a polypeptide of the invention operably linked to a nucleic acid encoding a detectable marker, e.g. luciferase), or detecting a cellular response, for example, cellular differentiation, or cell proliferation.

In yet another embodiment, an assay of the present invention is a cell-free assay comprising contacting a GLP-2 molecule or biologically active portion thereof with a test compound and determining the ability of the test compound to bind to the GLP-2 molecule or biologically active portion thereof. Binding of the test compound to the GLP-2 molecule can be determined either directly or indirectly as described above. In a preferred embodiment, the assay includes contacting the GLP-2 molecule or biologically active portion thereof with a known compound which binds the GLP-2 molecule to form an assay mixture, contacting the assay mixture with a test compound, and determining the ability of the test compound to interact with the GLP-2 molecule, wherein determining the ability of the test compound to interact with the GLP-2 molecule comprises determining the ability of the test compound to bind preferentially to the GLP-2 molecule or biologically active portion thereof as compared to the known compound.

In another embodiment, an assay is a cell-free assay comprising contacting a GLP-2 molecule or biologically active portion thereof with a test compound and determining the ability of the test compound to modulate (e.g., stimulate or inhibit) the activity of the GLP-2 molecule or biologically active portion thereof. Determining the ability of the test compound to modulate the activity of the GLP-2 molecule can be accomplished, for example, by determining the ability of the polypeptide to bind to a target molecule by one of the methods described above for determining direct binding. In an alternative embodiment, determining the ability of the test compound to modulate the activity of the GLP-2 molecule can be accomplished by determining the ability of the polypeptide of the invention to further modulate the target molecule. For example, the catalytic/enzymatic activity of the target molecule on an appropriate substrate can be determined as previously described.

In yet another embodiment, the cell-free assay comprises contacting a GLP-2 molecule or biologically active portion thereof with a known compound which binds the GLP-2 molecule to form an assay mixture, contacting the assay mixture with a test compound, and determining the ability of the test compound to interact with the GLP-2 molecule, wherein determining the ability of the test compound to interact with the GLP-2 molecule comprises determining the ability of the polypeptide to bind preferentially to or modulate the activity of a target molecule.

In more than one embodiment of the above assay methods of the present invention, it may be desirable to immobilize either the GLP-2 molecule or its target molecule to facilitate separation of complexed from uncomplexed forms of one or both of the molecules, as well as to accommodate automation of the assay. Binding of a test compound to the GLP-2 molecule, or interaction of the GLP-2 molecule with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase fusion proteins or glutathione-S-transferase fusion peptides can be adsorbed onto glutathione sepharose beads or glutathione derivatized microtiter plates, which are then combined with the test compound or the test compound and either the non-adsorbed target molecule or a GLP-2 molecule, and the mixture incubated under conditions conducive to complex formation (e.g., at physiological conditions for salt and pH). Following incubation, the beads or microtiter plate wells are washed to remove any unbound components and complex formation is measured either directly or indirectly, for example, as described above. Alternatively, the complexes can be dissociated from the matrix, and the level of binding or activity of the polypeptide of the invention can be determined using standard techniques.

Other techniques for immobilizing proteins on matrices can also be used in the screening assays of the invention. For example, either the GLP-2 molecule or its target molecule can be immobilized utilizing conjugation of biotin and streptavidin. Biotinylated polypeptide of the invention or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the GLP-2 molecule or target molecules but which do not interfere with binding of the polypeptide of the invention to its target molecule can be derivatized to the wells of the plate, and unbound target or polypeptide of the invention trapped in the wells by antibody conjugation. Methods for detecting such complexes, in addition to those described above for the GST-immobilized complexes, include immunodetection of complexes using antibodies reactive with the polypeptide of the invention or target molecule, as well as enzyme-linked assays which rely on detecting an enzymatic activity associated with the polypeptide of the invention or target molecule.

In another embodiment, modulators of expression of a GLP-2 molecule of the invention are identified in a method in which a cell is contacted with a candidate compound and the expression of the selected mRNA or protein (i.e., the mRNA or protein corresponding to a GLP-2 molecule) in the cell is determined. The level of expression of the selected mRNA or protein in the presence of the candidate compound is compared to the level of expression of the selected mRNA or protein in the absence of the candidate compound. The candidate compound can then be identified as a modulator of expression of the GLP-2 molecule based on this comparison. For example, when expression of the selected mRNA or protein is greater (statistically significantly greater) in the presence of the candidate compound than in its absence, the candidate compound is identified as a stimulator of the selected mRNA or protein expression. Alternatively, when expression of the selected mRNA or protein is less (statistically significantly less) in the presence of the candidate compound than in its absence, the candidate compound is identified as an inhibitor of the selected mRNA or protein expression. The level of the selected mRNA or protein expression in the cells can be determined by methods described herein.

In yet another aspect of the invention, a GLP-2 molecule can be used as "bait protein" in a two-hybrid assay or three hybrid assay (see, e.g., U.S. Pat. No. 5,283,317; Zervos et al., 1993, *Cell* 72:223-232; Madura et al., 1993, *J Biol. Chem.* 268:12046-12054; Bartel et al., 1993, *Bio/Techniques* 14:920-924; Iwabuchi et al., 1993, *Oncogene* 8:1693-1696; and PCT Publication No. WO 94/10300), to identify other proteins, which bind to or interact with a GLP-2 molecule and modulate activity of the GLP-2 molecule. Such binding proteins are also likely to be involved in the propagation of signals by the polypeptide of the inventions as, for example, upstream or downstream elements of a signaling pathway involving a GLP-2 molecule.

This invention further pertains to novel agents identified by the above-described screening assays and uses thereof for treatments as described herein.

5.4 Methods of Using GLP-2 Molecules and GLP-2 Activators

GLP-2 molecules or GLP-2 activators are administered to a patient, preferably a mammal, more preferably a human, for the treatment or prevention of a bone-related disorder or a calcium homeostasis related syndrome. GLP-2 molecules or GLP-2 activators of the invention can be used to treat acute or chronic forms of these conditions.

Also contemplated are methods of prevention or treatment involving combination therapies comprising administering an effective amount of a GLP-2 molecule or GLP-2 activator in combination with another therapeutic agent or agents. The other therapeutic agent or agent can be, for example, an anti-osteoporosis agent, a steroid hormone, a non-steroid hormone, growth factor, a selective estrogen receptor modulator, an insulin-releasing agent, an inhibitor of glucagon secretion, a glucagon antagonists, a circadian rhythm regulator, a growth hormone secretagogue, an agent that increases IGF-1 levels, an immunotherapeutic agent, a cytokine, a protease inhibitor, a vitronectin receptor antagonist, a bisphosphonate compound, a kinase inhibitor, an integrin receptor or antagonist thereof, an anti-obesity agent, a lipid-metabolism improving agent, a neuropeptide Y blocker, a kainate/AMPA receptor antagonist, a β-adrenergic receptor agonist, a compound that reduces caloric intake, an anti-diabetes agent, or a dietary nutrient. Examples of therapeutic agents include, but are not limited to, those in Table 1.

TABLE 1

Other Therapeutics to be Administered with GLP-2 Molecules or Activators anti-osteoporosis agent
    alendronate sodium
    calcium L-threonate (e.g., $C_8H_{14}O_{10}Ca$)
    clodronate
    etidronate
    gallium nitrate
    mithramycin
    norethindrone acetate (e.g., that which is commercially available as ACTIVELLA)
    osteoprotegerin
    pamidronate
    risedronate sodium
    parathyroid hormone
steroid hormones
    androgen (e.g., androstenedione, testosterone, dehydroepiandrosterone, dihydrotestosterone, 7-alpha-methyl-19-nortestosterone, 7-alpha-methyl-19-nortestosterone acetate, methandroil, oxymetholone, methanedione, oxymesterone, nordrolone phenylpropionate, norethandrolone)
    glucocorticoid
    estrogenic hormones (e.g., that which is commercially available as PREMARIN)
    progestin
non-steroid hormone
    calcitonin
    calcitriol
    growth hormone (e.g., osteoclast-activating factor)
    melatonin
    parathyroid hormone
    prostaglandin
    thyroid hormone
growth factor
    epidermal growth factor
    fibroblast growth factor
    insulin-like growth factor 1
    insulin-like growth factor 2
    platelet-derived growth factor
    vascular endothelial growth factor
selective estrogen receptor modulator
    BE-25327
    CP-336156
    clometherone
    delmadinone
    droloxifene
    idoxifene
    nafoxidine
    nitromifene
    ormeloxifene TABLE 1-continued Other Therapeutics to be Administered with GLP-2 Molecules or Activators raloxifene (e.g., that which is commercially available as EVISTA)
    tamoxifen
    toremifene
    trioxifene
    [2-(4-hydroxyphenyl)-6-hydroxynaphthalen-1-yl][4-[2-(1-piperidinyl)-ethoxy]phenyl]-methane
insulin-releasing agent
    GLP-1
    nateglinide
    repaglinide (e.g., that which is commercially available as PRANDIN)
    sulfonylurea (e.g., glyburide, glipizide, glimepiride)
    vasopressin
inhibitor of glucagon secretion
    somatostatin
glucagon antagonists
    substituted glucagons having an alanine residue at position 1, 2, 3-5, 9-11, 21, or 29
    des-His$^1$-Ala$^2$ glucagons
    des-His$^1$-[Ala$^{2,11}$-Glu$^{21}$] glucagon
circadian rhythm regulator
    alkylene dioxybenzene agonist
    melatonin
    neuropeptide Y
    tachykinin agonist
    visible light therapy
growth hormone secretagogue
    cycloalkano[b]thien-4-ylurea
    GHRP-1
    GHRP-6
    growth hormone releasing factor
    hexarelin
    thiourea
    B-HT920
    benzo-fused lactams (e.g., N-biphenyl-3-amido substituted benzolactams)
    benzo-fused macrocycles (e.g., 2-substituted piperidines, 2-substituted pyrrolidines, 2-substituted hexahydro-1H-azepines, di-substituted piperidines, di-substituted pyrrolidines, di-substituted hexahydro-1H-azepines, tri-substituted piperidines, tri-substituted pyrrolidines, tri-substituted hexahydro-1H-azepines, L-pyroglutamyl-pyridylalanyl-L-prolinamides)
agents that increase IGF-1 levels
    L-acetylcarnitine
    L-isovalerylcarnitine
    L-propionylcarnitine
immunotherapeutic agent
    antibody
    immunomodulator
cytokine
    endothelial monocyte activating protein
    granulocyte colony stimulating factor
    interferon (e.g., IFN-γ)
    interleukin (e.g., IL-6)
    lymphokine
    lymphotoxin-α
    lymphotoxin-β
    tumor necrosis factor
    tumor necrosis-factor-like cytokine
    macrophage inflammatory protein
    monocyte colony stimulating factor
    4-1BBL
    CD27 ligand
    CD30 ligand
    CD40 ligand
    CD137 ligand
    Fas ligand
    OX40 ligand
protease inhibitor
    cysteine protease inhibitor (e.g., vinyl sulfone, peptidylfluoromethyl ketone, cystatin C, cystatin D, E-64)
    DPP IV antagonist
    DPP IV inhibitor (e.g., N-(substituted glycyl)-2-cyanopyrrolidines, N-Ala-Pro-O-nitrobenzyl-hydroxylamine, and ε-(4-nitro)benzoxy-carbonyl-Lys-Pro)

TABLE 1-continued

Other Therapeutics to be Administered
with GLP-2 Molecules or Activators serine-protease inhibitor (e.g., azapeptide, BMS232632, antipain,
leupeptin)
vitronectin receptor antagonist
    anti-vitronectin receptor antibody (e.g., 23C6)
    cyclo-S,S—N α-acetyl-cysteinyl-N alpha-methyl-argininyl-glycyl-
    aspartyl-penicillamine
    RGD-containing peptide (e.g., echistatin)
bisphosphonate compound
    alendronate (e.g., that which is commercially available as
    FOSAMAX)
    aminoalkyl bisphosphonate (e.g., alendronate, pamidronate(3-amino-
    1-hydroxypropylidene)bisphosphonic acid disodium salt, pamidronic
    acid, risedronate(1-hydroxy-2-(3-pyridinyl)ethylidene)bisphos-
    phonate, YM 175 [(cycloheptylamino)methylene-bisphosphonic acid],
    piridronate, aminohexanebisphosphonate, tiludronate, BM-210955,
    CGP-42446, EB-1053)
    risedronate (e.g., that which is commercially available as ACTONEL)
kinase inhibitor
    Rho-kinase inhibitor (e.g., (+)-trans-4-(1-aminoethyl)-1-(4-
    pyridylcarbamoyl)-cyclohexane, trans-N-(1H-pyrrolo[2,3-b]pyridin-4-
    yl)-4-guanidinomethylcyclohexanecarbox amide, 1-(5-isoquinoline-
    sulfonyl)-homopiperazine, 1-(5-isoquinolinesulfonyl)-2-
    methylpiperazine)
integrin receptor
    α subunit (e.g., subtype 1-9, D, M, L, X, V, IIb, IELb)
    β subunit (e.g., subtype 1-8)
integrin receptor antagonists
    ethyl 3(S)-(2,3-dihydro-benzofuran-6-yl)-3-{2-oxo-3-[3-(5,6,7,8-
    tetrahydro-[1,8]naphthyridin-2-yl)-propyl]-tetrahydro-pyrimidin-1-
    yl}-propionate;
    ethyl 3(S)-(3-fluorophenyl)-3-(2-oxo-3(S or R)-[3-(5,6,7,8-tetrahydro-
    [1,8]naphthyridin-2-yl)-propyl]-piperidin-1-yl)-propionate;
    ethyl 3(S)-(3-fluorophenyl)-3-(2-oxo-3 ® or S)-[3-(5,6,7,8-
    tetrahydro-[1,8]naphthyridin-2-yl)-propyl]-piperidin-1-yl)-propionate;
    3(S)-(2,3-dihydro-benzofuran-6-yl)-3-{2-oxo-3-[3-(5,6,7,8-
    tetrahydro-[1,8]naphthyridin-2-yl)-propyl]-tetrahydro-pyrimidin-1-
    yl}-propionic acid;
    3(S)-(3-fluorophenyl)-3-(2-oxo-3(S or R)-[3-(5,6,7,8-tetrahydro-[1,8]-
    naphthyridin-2-yl)-propyl]-piperidin-1-yl)-propionic acid;
    3(S)-(3-fluorophenyl)-3-(2-oxo-3 ® or S)-[3-(5,6,7,8-tetrahydro-
    [1,8]naphthyridin-2-yl)-propyl]-piperidin-1-yl)-propionic acid
anti-obesity agent
    benzphetamine (e.g. that which is commercially available as
    DIDREX)
    benzylisopropylamine (e.g. that which is commercially available as
    IONAMIN)
    bupropion
    dexfenfluramine (e.g. that which is commercially available as
    REDUX)
    dextroamphetamine (e.g. that which is commercially available as
    DEXEDRINE)
    diethylpropion (e.g. that which is commercially available as
    TENUATE)
    dimethylphenethylamine (e.g. that which is commercially available as
    ADIPEX or DESOXYN)
    evodamine
    fenfluramine (e.g. that which is commercially available as
    PONDIMIN)
    fluoxetine
    mazindol (e.g. that which is commercially available as SANOREX or
    MAZANOR)
    methamphetamine
    naltrexone
    orlistat (e.g. that which is commercially available as XENICAL)
    phendimetrazine (e.g. that which is commercially available as
    BONTRIL or PLEGINE)
    phentermine (e.g. that which is commercially available as FASTIN)
    sibutramine (e.g. that which is commercially available as MERIDIA)
a lipid-metabolism improving agent
    capsaicin
an neuropeptide Y blocker
    NGD-95-1
kainate/AMPA receptor antagonist
β-adrenergic receptor agonist
compound that reduces caloric intake TABLE 1-continued Other Therapeutics to be Administered
with GLP-2 Molecules or Activators fat substitute (e.g., that which is commercially available as
    OLESTRA)
    sugar substitute (e.g., that which is commercially available as
    ASPARTAME)
anti-diabetes agent
    insulin glargine (e.g. that which is commercially available as
    LANTUS)
    pioglitazone (e.g. that which is commercially available as ACTOS)
    rosiglitazone maleate (e.g. that which is commercially available as
    AVANDIA)
dietary nutrient
    sugar
    dietary fatty acid
    triglyceride
    oligosaccharides (e.g., fructo-oligosaccharides, raffinose, galacto-
    oligosaccharides, xylo-oligosaccharides, beet sugar and soybean
    oligosaccharides)
    protein
    vitamin (e.g., vitamin D)
    mineral (e.g., calcium, magnesium, phosphorus and iron)

Agents that Promote Bone Turnover

Until recently, anti-resorptive medications such as bisphosphonates and raloxifene represented the main pharmacological treatment options for patients with osteoporosis. With the introduction of teriparatide (rhPTH (1-34)), a recombinant formulation of parathyroid hormone (PTH) consisting of the first 34 amino acids of the N-terminal region, bone-forming therapy has now become possible (Neer et al. Effect of parathyroid hormone (1-34) on fractures and bone mineral density in postmenopausal women with osteoporosis. N Engl J Med. 2001 May 10;344(19): 1434-41). Native PTH (1-84) and other PTH N-terminal fragments and analogues with similar anabolic potentials are also in development (Hodsman et al. Efficacy and safety of human parathyroid hormone-(1-84) in increasing bone mineral density in postmenopausal osteoporosis. J Clin Endocrinol Metab. 2003 November;88(11):5212-20. Horwitz et al. Short-term, high-dose parathyroid hormone-related protein as a skeletal anabolic agent for the treatment of postmenopausal osteoporosis.J Clin Endocrinol Metab. 2003 February;88(2):569-75).

Preclinical, as well as human studies, have shown increases in trabecular as well as cortical bone mass with subsequent improvements in bone microstructure and cortical thickness. The subcutaneous daily dose of teriparatide 20 μg has been shown to decrease the occurrence of new vertebral fractures in Caucasian women (70 years of age) by 65%, in a large randomised, double-blind placebo-controlled trial. Moderate-to-severe fractures or multiple vertebral fractures could be reduced by 90 and 77%, respectively. There was also a significant beneficial effect on new non-vertebral fractures (−35%) by the end of the 21-month treatment period. The reduction in non-vertebral fractures became evident after approximately 8-12 months of treatment. Smaller studies in men with low bone mass showed similar effects on bone mineral density and changes in bone turnover markers when compared to the results obtained in postmenopausal women. Recent data suggest that teriparatide is best given as monotherapy and not in combination with a bisphosphonate. Previous bisphosphonate treatment is also likely to diminish the bone anabolic potential ofteriparatide. Bisphosphonate treatment induces a reduction in both resorption and formation processes and it is speculated that this causes a reduction in remodelling space necessary for bone formation. Furthermore, bisphosphonate treatment is un-physiologic and not mediated through the interaction with any receptor. Thus, in order to preserve bone mass gained during the recommended 18- to 24-month treatment period with PTH, anti-resorptive medication should be prescribed following teriparatide treatment. As teriparatide is expensive, its use at the moment should be limited to patients with more severe forms of osteoporosis, usually with the presence or history of one or more fractures because of those patients' high risk for subsequent fractures (Dobnig H. A review of teriparatide and its clinical efficacy in the treatment of osteoporosis. Expert Opin Pharmacother. 2004 May;5(5):1153-62).

Studies so far have not shown serious PTH-related side effects. Nevertheless, hypercalcemia and related symptoms may occur (about 11% of treated individuals) and hamper patient compliance to long-term and thereby the efficacy of the treatment.

Teriparatide and related compounds therefore display a pattern of activity characterised by both a desired increase in the rate of bone formation and a delayed undesired increase in the rate of bone resorption. The present invention through the use of a GLP-2 or an analogue, variant, derivative or mimic thereof in combination with an active agent such as teriparatide, which has the effect when used alone of promoting both bone formation and bone resorption, overcomes or mitigates the undesired bone resorption activity of such an active agent.

The agent which promotes bone turnover (i.e. both resorption and formation) may be a PTH receptor binding ligand. This may be a naturally occurring PTH, an active fragment of PTH, PTHrP, an active fragment of PTHrP, TIP39, an active fragment of TIP39, or is an analogue or derivative of any one of said ligands having the ability to bind and activate a PTH receptor.

Parathyroid hormone (PTH) is an endocrine hormone which in man is an 84 residue peptide derived from a 115 amino acid precursor. Its activity seems to be due to its N-terminal region. As with GLP-2, PTH molecules corresponding to the sequence of PTH in non-human animals may be employed in this invention, as well as variants, analogues, derivatives and mimics of PTH (these terms being used in the same way as in relation to GLP-2, so that the explanatory passages above in relation to these terms as they apply to GLP-2 should be understood as applying mutatis mutandis in the context of PTH and the other bone formation stimulating agents discussed below also).

The sequence of the 84 amino acid mature human PTH is as follows:

SVSEIQLMHNLGKHLNSMERVEWLRKKLQDVHNFVALGAPLAPRDAGSQR

PRKKEDNVLVESHEKSLGEADKADVNVLTKAKSQ

Active N-terminal fragments of this sequence may be used according to the present invention including particularly fragments 1-37, 1-36, 1-34, 1-32 and 1-31.

Whilst PTH (1-31) is the shortest fragment of the natural sequence that has been shown to have the full PTH1 receptor activating capability of native PTH. However, it has been found that modified shorter PTH sequences are active, see for example U.S. Pat No. 6,417,333, where N-terminal PTH derivatives of 28 amino acids or less in which Ala or Gly is substituted for Ser at position 1 and/or Arg is substituted for Glu at position 19 are disclosed. Fragments containing the first 24, 25, 26, or 27 amino acids of such a sequence are found to be active.

Moreover, it has been found that amino acids 1-9 of PTH are sufficient for receptor activation, but that residues 15-34 are responsible for receptor binding (see Tsomaia et al, Biochemistry 2004, 43, 690-699). Accordingly, a conjugate containing an effective N terminal sequence as short as 1-9 may be used if said conjugate further contains an effective PTH receptor binding moiety.

An example of a sub-34 amino acid peptide that has been found to be effective is [Leu(27)]-cyclo(Glu(22)-Lys(26))-hPTH-(1-31)NH2. Also, hPTH (1-31) has been found to exert anabolic effect on the skeleton, but without activation of the protein kinase C second messenger pathway, which is a further activity of full length PTH and fragments of 34 amino acids or longer.

PTH activates a G-coupled receptor. There are two known such receptors (known as the PTH1 and PTH2 receptors) and the receptor of significance in the present invention is the PTH1 receptor, as this is present in bone. This receptor is activated not only by PTH but also by parathyroid hormone related protein (PTHrP).

The sequence of one human form of PTHrP is as follows:

MQRRLVQQWS VAVFLLSYAV PSCGRSVEGL SRRLKRAVSE

HQLLHDKGKS IQDLRRRFFL HHLIAEIHTA EIRATSEVSP

NSKPSPNTKN HPVRFGSDDE GRYLTQETNK VETYKEQPLK

TPGKKKKGKP GKRKEQEKKK RRTRSAWLDS GVTGSGLEGD

HLSDTSTTSL ELDSRRH

PTHrP is a second example of a compound stimulating bone turnover to which this aspect of the present invention applies. Variants, analogues, derivatives and mimics of PTHrP may be employed. As with PTH, N-terminal fragments of this sequence are active. Indeed, it may be that the secreted mature active form of PTHrP corresponds to amino acids 1-36 of the above sequence.

Numerous active variants of PTH and its fragments and of PTHrP and its fragments are known in the literature and may be used herein. These include those described in WO-A-94/02510, U.S. Pat. No. 6,472,505, WO-A-97/02834, WO-A-96/40193, WO-A-9603437 and U.S. Pat. No. 6,472,505, all of which are hereby incorporated by reference. Many of the disclosed variants and analogues in these documents are cyclic in structure.

As disclosed in WO94/02510, derivatives of naturally occurring forms of PTH may be prepared which differ from their natural counterparts by comprising at least one modification, such as at least one radical selected from a L- or D-α-amino acid, C2-6 alkoxycarbonyl, optionally substituted C1-8 alkyl, C2-8 alkenyl, C2-8 alkynyl, aralkyl, aralkenyl or C3-6 cycloalkyl-C1-4 alkyl attached to the terminal amino group of the PTH compound, and/or at least one radical selected from C2-6 alkoxycarbonyl, optionally substituted C1-8 alkyl, C2-8 alkenyl, C2-8 alkynyl, aralkyl, aralkenyl or C3-6 cycloalkyl-C1-4 alkyl and attached to one or more side chain amino groups of the PTH compound.

Alternatively, at least one a amino acid unit in the positions 1 to 38 of a naturally occurring PTH sequence may be replaced by a natural or unnatural amino acid unit optionally in protected form, whereby the α-amino acid units present in positions 1 and 2 at the amino terminus of the PTH sequence together or separately may be replaced by a pseudo-peptide. Particular sites for substitution of amino acids are residues 8 and 18 of PTH (1-34). Specific disclosed variants include:

[Leu8, Gln18, Thr33, Ala34]-hPTH(1-34)OH

[Leu8, Ala16, Gln18, Ala19, Thr33, Ala34]hPTH (1-34)OH

[Leu8, Ala16, Gln18, Thr33, Ala34]hLPTH(1-34)OH

[Leu8, Asp10, Lys11, Gln18]hPTH(1-36)OH

[Leu8, Asp10, Lys11, Gln18, Thr33, Ala34]hPTH (1-34)OH

[Leu8, Asp10, Lys11, Ala16, Gln18, Ala19]hPTH (1-36)OH

[Leu8, Asp10, Lys11, Ala16, Gln18, Thr33, Ala34] hPTH(1-34)OH

[LeuS, A5p10, Lys11, Ala16, GlnlS]hPTH (1-36)OH, and

[Leu8, Ala16, Gln18, Ala19]hPTH(1-36)OH in free form or in salt or complex form.

The PTH variants may be of a sequence obtained by replacing amino acids of PTH by corresponding amino acids of PTHrP, especially at positions 8 to 11, 16 to 19, or 33 and 34.

Analogues of PTH (1-34) may be prepared which differ from human PTH (1-34) in that i. the α-amino acid in position 1 is Gly, D-Ser, D-Ala or Tyr; or
ii. the α-amino acid in position 2 is Ala, D-Val, Lys, Arg or Cit and the α-amino acid in position 34 is Tyr; or the α-amino acid in position 2 is D-Val and the α-amino acid in position 34 is D-Tyr and optionally the α-amino acids in positions 8 and 18 are each Nle; or
iii. the α-amino acid in positions 3 and/or 6 and/or 9 are replaced by a natural or unnatural amino acid; or
iv. the α-amino acid in position 23 is replaced by Ala, Arg, Asn, Asp, Cys, Gln, Glu, Gly, His, Ile, Lys, Met, Pro, Ser or Thr; or
v. the α-amino acid in position 25 and/or 26 and/or 27 is replaced by Ala, Asn, Asp, Cys, Gln, Glu, Gly, His, Ile, Leu, Met, Phe, Pro, Ser, Thr, Trp, Tyr or Val; or
vi. the α-amino acids in positions 8 and 18 are each Nle or each Met(O) and optionally the α-amino acid in position 34 is Tyr; or the α-amino acids in positions 8 and 18 are each Nle and the α-amino acid in position 34 is Tyr and either the α-amino acid in position 12 is L- or D-Pro, L- or D-Ala, Aib or NMeGly or the α-amino acid in position 23 is Phe, Leu, Nle, Val, Tyr, α-Nal or β-Nal; or
vii. the α-amino acid in position 28 is Lys and the α-amino acid in position 30 is Leu; or
viii. the α-amino acid in position 1 is Aib; and/or the α-amino acid in position 8 and/or 18 is Leu, Ile, Val, Phe or Trp; and/or the α-amino acid in position 11 is Ser, Lys, Phe,B-Nal, Trp or Tyr; and/or the α-amino acid in position 12 is D-Leu, D-Ile, D-Nle, D-Val, D-Ser, D-Ser(Butyl), D-Abu, D-Thr, D-Nva, D-Met,D-β-Nal, D-Trp, D-Lys, D-Tyr, D-Phe or D-Asn; and/or the α-amino acid in position 13 is Leu; and/or the α-amino acid in position 19 and/or in position 21 is Arg, Lys, Asn or His; and/or the α-amino acid in position 23 is 2-(1,3-dithiolane 2-yl)Trp; and/or the α-amino acid in position 25 and/or in position 26 is His; and/or the α-amino acid in position 27 is Gln or Leu; or
ix. the α-amino acid in position 8 and/or 18 is Ala or Ser; or the α-amino acid in position 8 and/or 18 is Ala, Val, Leu, Ile, Ser or Trp and the α-amino acid in position 34 is Tyr.

As disclosed in WO 97/02834, analogues of PTH may be prepared based on human PTH (1-34) in which at least one amino acid at positions 7, 11, 23, 24, 27, 28 or 31 is Cha (cyclohexyl aniline) or at least one amino acid at positions 3, 16, 17, 18, 19, or 34 is Aib (αaminoisobutryic acid). The amino acid at position 1 may be α,β diaminoproprionic acid, the amino acid at position 27 may be homoarginine, and the amino acid at position 31 may be norleucine. The following analogues are examples:

[Cha7]hPTH(1-34)NH2; [Cha11]hPTH(1-34)NH2; [Cha15] hPTH(1-34)NH2; [Cha7, 11]hPTH(1-34)NH2; [Cha7, 11, Nle8, 18, Tyr34]hPTH(1-34)NH2; [Cha23]hPTH(1-34) NH2; [Cha24)hPTH(1-34)NH2; [Nle8t 18, Cha27]hPTH (1-34)NH2; [NH2; [Cha28]hPTH(1-34)NH2; [Cha31] hPTH(1-34)NH2; [Cha27]hPTH(1-34)NH2; [Cha27, 29]hPTH)1-34)NH2; [Cha28]bPTH(1-34)NH2; [Cha28] rPTH(1-34)NH2; [Cha24, 28, 31]hPTH(1-34)NH2; [Aib16]hPTH(1-34)NH2; [Aib19]hPTH(1-34)NH2; [Aib34]hPTH(1-34)NH2;[Aib16, 19]hPTH(1-34)NH2; [Aib16, 19, 34]bPTH(1-34)NH2; [Aib16, 34]hPTH(1-34) NH2; [Aib19, 34]hPTH(1-34)NH2[Cha7, 11, Nle8, 18 Aib16, 19 Tyr34]hPTH(1-34)NH2; [Cha7 11, Nle8, 18, 31 Aib16, 19 Tyr34]hPTH(1-34)NH2; [Cha7, Aib16] hPTH(1-34)NH2; [Cha11, Aib16]hPTH(1-34)NH2; [Cha71 Aib34]hPTH(1-34)NH2; [Cha11, Aib34]hPTH(1-34)NH2; [Cha27, Aib16]hPTH(1-34)NH2; [Cha27, Aib34]hPTH(1-34)NH2; [Cha28, Aib16]hPTH(1-34) NH2; [Cha28, Aib34]hPTH(1-34)NH2; [Nle31]hPTH(1-34)NH2; [hArg27]hPTH(1-34)NH2; [Dap1, Nle8, 18, Tyr34]hPTH(1-34)NH2; [Nle31]bPTH(1-34)NH2; [Nle31]rPTH(1-34)NH2; [hArg27]bPTH(1-34)NH2; [hArg27]rPTH(1-34)NH2; [Cha7, 11, Aib19, Lys30] hPTH(1-34)NH2; [Aib12]hPTH(1-34)NH2; [Cha24, 28, 31, Lys30]hPTH(1-34)NH2; [Cha28, 31]hPTH(1-34) NH2; [Cha7, 11, Nle8, 18, Aib34]hPTH(1-34)NH2; [Aib3]hPTH(1-34)NH2; [Cha8]hPTH(1-34)NH2; [Cha15]hPTH(1-34)NH2; [Cha7, 11, Aib19]hPTH(1-34) NH2; [Cha7, 11, Aib16]hPTH(1-34)NH2; [Aib17]hPTH (1-34)NH2; [Cha5]hPTH(1-34)NH2; [Cha7, 11, 15]hPTH(1-34)NH2; [Cha7, 11, Nle8, 18, Aib19, Tyr34] hPTH(1-34)NH2; [Cha7, 11, Nle8, 18, Aib19, Lys30, Tyr34]hPTH(1-34NH2; [Cha7,11, 15 15]hPTH(1-34) NH2; [Aib17]hPTH(1-34)NH2; [Cha7, 11, Leu27]hPTH (1-34) NH2; [Cha7, 11, 15, Leu27]hPTH(1-34)NH2; [Cha7, 11, 27]hPTH(1-34)NH2; [Cha7, 11, 15, 27]hPTH (1-34)NH2; [Trp15]hPTH(134)NH2; [Nal15]hPTH(1-34) NH2; [Trp15, Cha23]hPTH(1-34)NH2; [Cha15, 23]hPTH (1-34)NH2; [Phe7, 11]hPTH(1-34)NH2; [Nal7, 11]hPTH (1-34)NH2; [Trp7, 11]hPTH (1-34)NH2; [Phe7, 11, 15]hPTH(1-34)NH2; [Nal7, 11, 15]hPTH(1-34)NH2; [Trp7, 11, 15]hPTH(1-34)NH2; and [Tyr7, 11, 15]hPTH (1-34)NH2.

Similarly, analogues of PTHrP are disclosed to include:
[Cha7]hPTHrP(1-34)NH2; [Cha11]hPTHrP(1-34)NH2; [Cha7t 11]hPTHrP(1-34)NH2; [Aib16, Tyr34hPTHrP(1-34)NH2; [Aib19]hPTHrP(1-34)NH2; [Aib16, 19]hPTHrP(1-34)NH2; [Cha7, 11, Aib16hPTHrP(1-34) NH2; [Cha7, 11, Aib19]hPTHrP(1-34)NH2; [Cha22, Leu23 28, 31, Glu25, 29, Lys26,30]hPTHrP(1-34)NH2; [Glu22, 25, 29, Leu23, 28, 31, Lys26, 30]hPTHrP(1-34)NH2; [Cha221 23 Glu25, 29, Leu28, 31, Lys26, 30]hPTHrP(1-34)NH2; [Glu22, 25, Leu23, 28, 31, Aib29, Lys26, 30]hPTHrP(1-34)NH2; [Glu22, 25, 29, Lys23, 26, 30, Leu28, 31]hPTHrP(1-34)NH2; [Glu22, 25, 29 Leu23, 28, 31, Lys261 Cha30]hPTHrP(1-34)NH2; [Glu22, 25, 29 Leu23, 28, 31, Lys26, Aib30]hPTHrP(1-34)NH2; [Glu22, 25, 29 Leu23, 31, Lys26, 28, 30]hPTHrp(1-34) NH2; [Cha22, 23, 24, 27, 28, 31, Glu25, 29, Lys26, 30]hPTHrP (1-34)NH2; [Glu22, 25, 29, Cha23, 24, 28, 31, Lys26, 27, 30]hPTHrP(1-34)NH2; [Glu22, 25, 29, Cha23, 24, 27, 31, Lys26, 28, 30]hPTHrP(1-34)NH2; [Glu22, 25, 29 Lys23, 26, 30 Cha24, 27, 28, 31]hPTHrP(1-34)NH2; [Cha22, Leu23, 28, 31, Glu25, 29, Lys26, 27, 30]hPTHrP(1-34) NH2; [Cha22, Leu23, 31, Glu25, 29, Lys26, 28, 30]hPTHrP(1-34)NH2; [Cha22, Lys23, 26, 30, Glu25, 29, Leu28, 31]hPTHrP(1-34)NH2; [Cha22, Leu23, 28, 31Glu25, Lys26, 30, Aib29]hPTHrP(1-34)NH2; [Cha22, Leu23, 28, 31, Glu25, 29, Lys26, Aib30]hPTHrP(1-34) NH2; [Glu22, 25, Leu23, 28, 31, Lys26, 27, 30, Aib29] hPTHrP(1-34)NH2; [Glu22, 25, Lys23, 26,30 Leu 28, 31, Aib29]hPTHrP(1-34)NH2[Glu22, 25, Leu23, 31, Lys 26, 28, 30, Aib29]hPTHrP(1-34)NH2; [Cha7, 11, Glu22, 25, 29, Leu23, 28, 31, Lys26, 30]hPTHrP(1-34)NH2; [Cha7, 11, 22, Leu23, 28, 31, Glu25, 29, Lys26, 30]hPTHrP(134) NH2; [Cha7, 11, Glu22, 25, 29, Leu23, 28, 31, Lys26, 27, 30]hPTHrP(1-34)NH2; [Cha7, 11, 22, 23, Glu25, 29 Leu28, 31, Lys26, 30]hPTHrP(1-34)NH2; [Cha7, 11, Glu22, 25, 29, Lys23, 26, 30, Leu28, 31]hPTHrP(1-34) NH2; [Cha7t 11, Glu22, 25, 29, Leu23, 31, Lys26, 28, 30]hPTHrP(1-34)NH2; [Cha7, 11, Glu22, 25, Leu23, 28, 31, Aib29, Lys26, 30]hPTHrP(1-34)NH2; [Cha7, 11, Glu22, 25, 29, Leu23, 28, 31, Lys26, Aib30]hPTHrP(1-34)NH2; [Cha15, Glu22, 25, 29, Leu23, 28, 31 Lys26, 30]hPTHrP(1-34) NH2; [Cha15, 22, Leu23, 28, 31, Glu25, 29, Lys26, 30]hPTHrP(1-34)NH2; [Cha15, Glu22, 25, 29, Leu23, 28, 31, Lys26, 27, 30]hPTHrP(1-34)NH2; [Cha15t 22, 23, Glu25, 29, Leu28, 31, Lys26, 30]hPTHrP(1-34) NH2; [Cha15, Glu22,25, Leu23, 28, 31, Aib29, Lys26, 30]hPTHrP(1-34)NH2; [Cha15, Glu22, 25, 29, Lys23, 26, 30, Leu28, 31]hPTHrP(1-34) NH2; [Cha15, Glu22, 25, 29, Ley23, 28, 31, Lys26, Aib30]hPTHrP(1-34)NH2; [Cha15, Glu22, 28, 29, Leu23,31, Lys26, 28, 30]hPTHrP(1-34)NH2; [Cha15, 30, Glu22, 25, 29, Leu23, 28, 31, Lys26]hPTHrP(1-34)NH2; [Cha7, 8, 22, Leu23, 28, 31, Glu25, 29, Lys26, 30]hPTHrP(1-34)NH2; [Cha7, 8, Glu22, 25, 29, Glu23, 28, 31, Lys26, 27, 30]hPTHrP(1-34)NH2; [Cha7, 8, 22, 23, Glu25, 29, Leu28, 31, Lys26, 30]hPTHrP (1-34)NH2; [Cha7, 8, Glu22, 25, 29, Leu23, 28, 31, Lys26, 30]hPTHrP(1-34) NH2; [Cha7, 8, Glu22, 25, 29, Leu23, 28, 31, Aib29, Lys26, 30]hPTHrP(1-34) NH2; [Cha7, 8, Glu22, 25, 29, Lys23, 26, 30, Leu28, 31]hPTHrP(1-34)NH2; [Cha7, 8, Glu22, 25, 29, Leu23, 28, 31, Lys26, Aib30]hPTHrP(1-34)NH2; [Cha7, 8, Glu22, 25, 29, Leu23, 31, Lys26, 28, 30]hPTHrP(1-34)NH2; [Cha7, 8 30, Glu22, 25, 29, Leu23, 28, 31, Lys26]hPTHrP(1-34)NH2; [Ser1, Ile5, Cha7, 11, 22, Met8, Asn10, His14, Leu23, 28, 31, Glu25, 29, Lys26, 30]hPTHrP(1-34) NH2; [Ser1, Ile5, Cha7, 11, Met8, Asn10, His14, Glu22, 25, 29 Leu23, 28, 31 Lys26, 27, 30]hPTHrP(1-34)NH2; [Ser1, Ile5, Cha7, 11, Met8, Asn10, His14, Glu22, 25, 29, Leu23, 31, Lys26, 28, 30]hPTHrP(1-34)NH2; Ser1, Ile5, Cha7, 11, Met8, Asn10, His14, Glu22, 25, 29 Lys23, 26, 30 Leu28, 31[hPTHrP(1-34)NH2; [Ser1, Ile5, Cha7, 11, Met8, Asn10, His14, Glu22, 25, Leu23, 28, 31, Aib29, Lys26, 30]hPTHrP(1-34) NH2; [Ser1, Ile5, Cha7, 11, Met8, Asn10, His14, Glu22, 25, 29, Lys26, Aib30]PTHrP(1-34)NH2; [Ser1, Ile5, Cha7, 11, 22, 23, Met8, Asn10, His14, Glu25, 29 Leu28, 31, Lys26, 30]hPTHrP(1-34)NH2; [Ser1, Ile5, Cha7, 11, 15, Met8, Asn10, His14]hPTHrP(1-34)NH2; [Ser1, Ile5, Met8, Asn10, Leu11, His14, Aib16]hPTHrP (1-34)NH2; [Ser1, Ile5, Met8, Asn10, Leu11, 28, 31, His14, Cha22, 23, Glu25, 29, Lys26, 30]hPTHrP (1-34)NH2; [Ser1, Ile5, Cha7, 11, Met8, Asn10, His14, Glu22, 25, 29, Leu23, 28, 31, Lys26, 30]hPTHrP (1-34)NH2; [Ser1, Ile5, Met8, Asn10, His14, Cha15, Glu22, 25, 29 Leu23, 28, 31Lys26, 30]hPTHrP (1-34)NH2; [Ser1, Ile5, Cha7, 8, Asn10, His14, Glu22, 25, 29, Leu23, 28, 31 Lys26, 30]hPTHrP (1-34)NH2; [Glu22, 25, 29, Leu23, 28, 31, Lys24, 26, 30]hPTHrP(1-34)NH2; [Aib22, Leu23, 28, 31Glu25, 29, Lys26, 30]hPTHrP(1-34)NH2; [Glu22, 29, Leu23, 28, 31, Aib25, Lys26, 30]hPTHrP(1-34)NH2; [Glu22, 25, 29, Leu23, 28, 31, Aib26, Lys30]hPTHrP (1-34)NH2; [Glu22, 25, 29, Leu23, 28, Lys 26, 30, 31]hPTHrP(1-34) NH2; [Ser1, Ile5, Met8, Asn10, Leu11, 23, 28, 31, His14, Cha22, Glu25, 29, Lys26, 30]hPTHrP(1-34)NH2; [Ser1, Ile5, Met8, Asn10, Leu11, 28, 31, His14, Glu22, 25, 29, Lys23, 26, 30]PTHrP(1-34)NH2; [Ser1, Ile5, Met8, Asn10, Leu11, 23, 28, 31, His14, Glu22, 25, 29, Lys26, 27, 30]hPTHrP(1-34)NH2; [Ser1, Ile5, Met8, Asn10, Leu11 , 23, 31, His141Glu22, 25, 29, Lys26, 28, 30]hPTHrP(1-34)NH2; [Ser1, Ile5, Met8, Asn10, Leu11, 23, 28, 31 His14, Glu22, 25, Aib29, Lys26, 30]hPTHrP (1-34)NH2; [Ser1, Ile5, Met8, Asn10, Leu11, 23, 28, 31, His14, Glu22, 25, 29, Lys26, Aib30]hPTHrP(1-34)NH2; or [Ser1, Ile5, Met8]hPTHrP(1-34)NH2.

β-Nal, Nle, Dap, Cha, Nva, Amp, Pal, and Aib are the abbreviations of the following α-amino acids: p-(2-naphthyl)alanine, norleucine,a,p-diaminopropionic acid, cyclohexylalanine, norvaline, 4amino-phenylalanine, 3-pyridinylalanine, and aaminoisobutyric acid, respectively Cyclic analogues of PTH and PTHrP are described in WO96/40193 where a disulphide bond or amide bond links the side chains of amino acid residues 13 and 17, 26 and 30, or of both pairs. These cyclic analogues include c(Lys13, Asp17)hPTH(1-34)NH2; c(Lys13, Asp17)bPTH(1-34)NH2; c[Lys13, Asp17)rPTh(1-34)NH2; c[Lys13, Asp17][Nle8,18, Tyr34]hPTH(1-34)NH2; c[Lys13, Asp17][Nle8,18, Tyr 34]rPTH(1-34)NH2; or c[Lys13, Asp17][Nle8,18, Tyr34) bPTH(1-34)NH2; c[Lys26, Asp30)hPTH(1-34)NH2; c[Lys26, Asp30]bPTH(1-34)NH2; c[Lys26, Asp30]rPTH(1-34)NH2; c[Lys26, Asp30]hpT(1-34)NH2; H Tyr34]hPTH (1-34)NH2; c[Lys26, Asp30][Nle8,18, Tyr34]bPTH(1-34) NH2; Asp30][Nle8,18, Tyr34)rPTH(1-34)NH2; c[Lys13, Asp17]c[Lys26, Asp30][Nle8,18, c[Lys13, Asp17]c[Lys26, Asp30]bPTH(1-34)NH2; c[Lys13, Asp17]c[Lys26, Asp30] rPTH(1-34)NH2; c[Lys13, Asp17]c[Lys26, Asp30][Nle8, 18, Tyr34]hPTH(1-34)NH2; c[Lys13, Asp17]c[Lys26, Asp30][Nle8, 18, Tyr34]rPTH (1-34)NH2; or c[Lys13, Asp17]c[Lys26, Asp30][Nle8,18, Tyr34)bPTH(1-34)NH2; where h, b, and r stand for human, bovine and rat respectively.

In WO96/03437, PTH or PTHrP variants are disclosed in which at least one of the amino acid residues naturally occurring at positions 2 or 10 is replaced by tryptophan or another amino acid bearing a side chain having an aromatic or heteroaromatic group such as an optionally ring substituted 3- or 4- pyridyl-methyl, 3-indolyl-methyl, or 3-indazolyl-methyl group.

U.S. Pat. No. 6,472,505 discloses cyclic variants of PTH which include:
Cyclo(K<18>-D<22>)[A<1>,Nle<8>,K<18>,D<22>, L<27>]hPTH(1-31)NH2;

Cyclo(K<18>-D<22>)[A<1,2>,Nle<8>,K<18>,D<22>,L<27>]hPTH(1-31)NH2;
Cyclo(K<18>-D<22>)[A<1,3>,Nle<8>,K<18>,D<22>,L<27>]hPTH(1-31)NH2;
Cyclo(K<18>-D<22>)[A<1,4>,Nle<8>,K<18>,D<22>,L<27>]hPTH(1-31)NH2;
Cyclo(K<18>-D<22>)[A<1,5>,Nle<8>,K<18>,D<22>,L<27>]hPTH(1-31)NH2;
Cyclo(K<18>-D<22>)[A<1,6>,Nle<8>,K<18>,D<22>,L<27>]hPTH(1-31)NH2;
Cyclo(K<18>-D<22>)[A<1,7>,Nle<8>,K<18>,D<22>,L<27>]hPTH(1-31)NH2;
Cyclo(K<18>-D<22>)[A<1,9>,Nle<8>,K<18>,D<22>,L<27>]hPTH(1-31)NH2;
Cyclo(K<18>-D<22>)[A<1,10>,Nle<8>,K<18>,D<22>,L<27>]hPTH(1-31)NH2;
Cyclo(K<18>-D<22>)[A<1,11>,Nle<8>,K<18>,D<22>,L<27>]hPTH(1-31)NH2;
Cyclo(K<18>-D<22>)[A<1,12>,Nle<8>,K<18>,D<22>,L<27>]hPTH(1-31)NH2;
Cyclo(K<18>-D<22>)[A<1,13>,Nle<8>,K<18>,D<22>,L<27>]hPTH(1-31)NH2;
Cyclo(K<18>-D<22>)[A<1,14>,Nle<8>,K<18>,D<22>,L<27>]hPTH(1-31)NH2;
Cyclo(K<18>-D<22>)[A<1,15>,Nle<8>,K<18>,D<22>,L<27>]hPTH(1-31)NH2;
Cyclo(K<18>-D<22>)[A<1,16>,Nle<8>,K<18>,D<22>,L<27>]hPTH(1-31)NH2;
Cyclo(K<18>-D<22>)[A<1,17>,Nle<8>,K<18>,D<22>,L<27>]hPTH(1-31)NH2;
Cyclo(K<18>-D<22>)[G<1>,Nle<8>,K<18>,D<22>,L<27>]hPTH(1-31)NH2;
Cyclo(K<18>-D<22>)[A<1>,G<2>,Nle<8>,K<18>,D<22>,L<27>]hPTH(1-31)NH2;
Cyclo(K<18>-D<22>)[A<1>,G<3>,Nle<8>,K<18>,D<22>,L<27>]hPTH(1-31)NH2;
Cyclo(K<18>-D<22>)[A<1>,G<4>,Nle<8>,K<18>,D<22>,L<27>]hPTH(1-31)NH2;
Cyclo(K<18>-D<22>)[A<1>,G<5>,Nle<8>,K<18>,D<22>,L<27>]hPTH(1-31)NH2;
Cyclo(K<18>-D<22>)[A<1>,G<6>,Nle<8>,K<18>,D<22>,L<27>]hPTH(1-31)NH2;
Cyclo(K<18>-D<22>)[A<1>,G<7>,Nle<8>,K<18>,D<22>,L<27>]hPTH(1-31)NH2;
Cyclo(K<18>-D<22>)[A<1>,G<8>,K<18>,D<22>,L<27>]hPTH(1-31)NH2;
Cyclo(K<18>-D<22>)[A<1>,G<9>,Nle<8>,K<18>,D<22>,L<27>]hPTH(1-31)NH2;
Cyclo(K<18>-D<22>)[A<1>,G<10>,Nle<8>,K<18>,D<22>,L<27>]hPTH(1-31)NH2;
Cyclo(K<18>-D<22>)[A<1>,G<11>,Nle<8>,K<18>,D<22>,L<27>]hPTH(1-31)NH2;
Cyclo(K<18>-D<22>)[A<1>,G<13>,Nle<8>,K<18>,D<22>,L<27>]hPTH(1-31)NH2;
Cyclo(K<18>-D<22>)[A<1>,G<14>,Nle<8>,K<18>,D<22>,L<
Cyclo(K<18>-D<22>)[A<1>,G<15>,Nle<8>,K<18>,D<22>,L<27>]hPTH(1-31)NH2;
Cyclo(K<18>-D<22>)[A<1>,G<16>,Nle<8>,K<18>,D<22>,L<27>]hPTH(1-31)NH2;
Cyclo(K<18>-D<22>)[A<1>,G<17>,Nle<8>,K<18>,D<22>,L<27>]hPTH(1-31)NH2;
Cyclo(K<18>-D<22>)[D-P<1>,Nle<8>,K<18>,D<22>,L<27>]hPTH(1-31)NH2;
Cyclo(K<18>-D<22>)[A<1>,D-P<3>,Nle<8>,K<18>,D<22>,L<27>]hPTH(1-31)NH2;
Cyclo(K<18>-D<22>)[A<1>,D-P<6>,Nle<8>,K<18>,D<22>,L<27>]hPTH(1-31)NH2;
[0339]Cyclo(K<18>-D<22>)[A<1>,D-P<7>,Nle<8>,K<18>,D<22>,L<27>]hPTH(1-31)NH2;
Cyclo(K<18>-D<22>)[A<1>,D-P<9>,Nle<8>,K<18>,D<22>,L<27>]hPTH(1-31)NH2; (SEQ ID NO: 40);
Cyclo(K<18>-D<22>)[A<1>,D-P<10>,Nle<8>,K<18>,D<22>,L<27>]hPTH(1-31)NH2;
Cyclo(K<18>-D<22>)[A<1>,D-P<14>,Nle<8>,K<18>,D<22>,L<27>]hPTH(1-31)NH2;
[Cyclo(K<18>-D<22>)[A<1>,D-P<15>,Nle<8>,K<18>,D<22>,L<27>]hPTH(1-31)NH2;
Cyclo(K<18>-D<22>)[A<1>,D-P<16>,Nle<8>,K<18>,D<22>,L<27>]hPTH(1-31)NH2;
Cyclo(K<18>-D<22>)[A<1>,D-P<17>,Nle<8>,K<18>,D<22>,L<27>]hPTH(1-31)NH2;
Cyclo(K<18>-D<22>)[A<1>,Nle<8>,K<18>,D<22>,L<27>]hPTH(1-31)NH2;
Cyclo(K<18>-D<22>)[A<1>,Nle<8>,D<18>,K<22>,L<27>]hPTH(1-31)NH2;
Cyclo(O<18>-D<22>)[A<1>,Nle<8>,O<18>,O<22>,L<27>]hPTH(1-31)NH2;
Cyclo(D<18>-O<22>)[A<1>,Nle<8>,D<18>,O<22>,L<27>]hPTH(1-31)NH2;
Cyclo(K<18>-E<22>)[A<1>,Nle<8>,K<18>,E<22>,L<27>]hPTH(1-31)NH2;
Cyclo(O<18>-E<22>)[A<1>,Nle<8>,O<18>,E<22>,L<27>]hpTH (1-30)NH2;
Cyclo(K<18>-D<22>)[A<1>,Nle<8>,K<18>,D<22>,L<27>]hPTH(1-29)NH2;
[Cyclo(K<18>-D<22>)[A<1>,Nle<8>,K<18>,D<22>,L<27>]hPTH(1-28)NH2;
Cyclo(K<18>-D<22>)[A<1>,Nle<8>,K<18>,D<22>,L<27>]hPTH(1-31)NH2;
Cyclo(K<18>-D<22>)[A<1>,Nle<8>,K<18>,D<22>,L<27>]hpTH(1-27)NH2;
Cyclo(K<18>-D<22>)[Nle<8>,K<18>,D<22>,L<27>]hPTH(3-31)NH2;
Cyclo(K<18>-D<22>)[Nle<8>,K<18>,D<22>,L<27>]hPTH(2-31)NH2;
Cyclo(K<10>-D<14>)[A<1>,Nle<8,18>,K<10>,D<14>,L<27>]hPTH(1-31)NH2;
Cyclo(K<14>-D<18>)[A<1>,Nle<8>,K<14>,D<18>,L<27>]hPTH(1-31)NH2;
Cyclo(K<17>-D<21>)[A<1>,Nle<8,18>,K<17>,D<21>,L<27>]hPTH(1-31)NH2;
Cyclo(K<21>-D<25>)[A<1>,Nle<8,18>,K<21>,D<25>,L<27>]hPTH(1-31)NH2;
Cyclo(K<25>-D<29>)[A<1>,Nle<8,18>,K<25>,D<29>,L<27>]hPTH(1-31)NH2;
Cyclo(K<18>-D<22>)[K<18>,D<22>]hPTH(1-34)NH2;
Cyclo(K<18>-D<22>)[K<18,26,30>,D<22>,L<23,28,31>,E<25, 29>]hPTH(1-31)NH2;
Bicyclo(K<13>-D<17>,K<18>-D<22>)[A<1>,Nle<8>,D<17,22>,K<18>,L<27>]hPTH(1-31)NH2;
Bicyclo(K<18>-D<22>,K<26>-D<30>)[A<1>,Nle<8>,K<18>,D<22>,L<27>]hPTH(1-31)NH2; and
Tricyclo(K<13>-D<17,22>,K<18>-D<22>,K<26>-D<30>)[A<1>,Nle<8>,K<18>,D<17>,L<27>]hPTH(1-31)NH2;

PTH and PTHrP from other vertebrate species, especially mammalian species are highly homologous to the human forms of these peptides and may be used. These include porcine, rat, bovine, chicken PTH and PTHrP and their respective variants, analogues, derivatives and mimics.

Accordingly, the invention includes the use with said first active component which promotes bone formation and promotes bone resorption of PTH receptor binding and activating ligands which may be selected from a PTH, an active fragment of PTH, PTHrP, an active fragment of PTHrP, or is an analogue or derivative of any one of said ligands having the ability to bind and activate a PTH receptor.

It is preferred that the PTH receptor ligand is a PTH-1 receptor binding ligand, which may be selective for PTH-1 receptor binding or which may also bind and activate the PTH-2 receptor.

The PTH receptor ligand may be a full length PTH or is a C-terminal truncated PTH, optionally modified from a natural sequence by substitution of one or more amino acids, for instance a full length PTH or an N-terminal fragment containing at least the first 31 amino acid residues of PTH, optionally modified from a natural sequence by substitution of one or more amino acids. In particular, it may be hPTH (1-84), hPTH (1-37), hPTH (1-36), HPTH (1-34), hPTH (1-31), or a variant thereof, or a cyclic derivative of any of the foregoing, e.g. [Leu(27)]-cyclo(Glu(22)-Lys(26))-hPTH-(1-31)NH(2).

Equally, it may be a full length PTHrP or a C-terminal truncated PTHrP, such as PTHrP (1-40) optionally modified from a natural sequence by substitution of one or more amino acids.

When used in combination with PTH or a fragment thereof, one preferred dosage regime will be a dose of 5-50 e.g. about 20 µg/kg PTH 1-34 or 10-1,000 e.g. about 100 µg/kg PTH 1-84 in combination with 200-15,000 e.g. about 1600 µg/kg GLP-2 or an equivalently active amount of a GLP-2 variant, analog, derivative or mimic. These actives may be administered simultaneously or consecutively, e.g. by subcutaneous injection.

The other therapeutic agents can be made and used at doses as disclosed previously. For example, an anti-osteoporosis agent (see e.g., U.S. Pat. Nos. 2,565,115 and 2,720,483), a non-steroid hormone (see, e.g., U.S. Pat. Nos. 6,121,253; 3,927,197; 6,124,314), a glucagon antagonists (see, e.g., U.S. Pat. No. 5,510,459), a growth hormone secretagogue (see, e.g., U.S. Pat. Nos. 3,239,345; 4,036,979; 4,411,890; 5,206,235; 5,283,241; 5,284,841; 5,310,737; 5,317,017; 5,374,721; 5,430,144; 5,434,261; 5,438,136; 5,494,919; 5,494,920; and 5,492,916; European Patent Nos. 144,230 and 513,974; International Patent Publication Nos. WO 89/07110; WO 89/07111; WO 93/04081; WO 94/07486; WO 94/08583; WO 94/11012; WO 94/13696; WO 94/19367; WO 95/03289; WO 95/03290; WO 95/09633; WO 95/11029; WO 95/12598; WO 95/13069; WO 95/14666; WO 95/16675; WO 95/16692; WO 95/17422; WO 95/17423; WO 95/34311; and WO 96/02530), an agent that increase IGF-1 levels (see, e.g., U.S. Pat. No. 6,166,077), a cytokine (see, e.g., U.S. Pat. No. 4,921,697), a vitronectin receptor antagonist (see e.g., U.S. Pat. No. 6,239,138 and Horton et al., 1991, Exp. Cell Res. 195:368), a bisphosphonate compound (see e.g., U.S. Pat. No. 5,409,911), a kinase inhibitor (U.S. Pat. No. 6,218,410), and an integrin receptor or antagonist thereof (see, e.g., U.S. Pat. No. 6,211,191).

Alternatively, the other therapeutic agents can be made and used at doses as determined empirically.

5.5 Therapeutic/prophylactic Administration and Compositions of the Invention.

Due to their activity, the GLP-2 molecules and GLP-2 activators are advantageously useful in human and veterinary medicine. As described above, the compounds of the invention are useful for treating or preventing a bone-related disorder or a calcium homeostasis related syndrome in a patient.

When administered to a patient, a GLP-2 molecule or GLP-2 activator is preferably administered as a component of a composition that optionally comprises a pharmaceutically acceptable carrier or vehicle. In a preferred embodiment, these compositions are administered orally.

Compositions for oral administration might require an enteric coating to protect the composition(s) from degradation within the gastrointestinal tract. In another example, the composition(s) can be administered in a liposomal formulation to shield the GLP-2 molecules and GLP-2 activators disclosed herein from degradative enzymes, facilitate the molecule's transport in the circulatory system, and effect delivery of the molecule across cell membranes to intracellular sites.

GLP-2 molecules and GLP-2 activators intended for oral administration can be coated with or admixed with a material (e.g., glyceryl monostearate or glyceryl distearate) that delays disintegration or affects absorption of the GLP-2 molecule in the gastrointestinal tract. Thus, for example, the sustained release of a GLP-2 molecule can be achieved over many hours and, if necessary, the GLP-2 molecule can be protected from being degraded within the gastrointestinal tract. Taking advantage of the various pH and enzymatic conditions along the gastrointestinal tract, pharmaceutical compositions for oral administration can be formulated to facilitate release of a GLP-2 molecule at a particular gastrointestinal location.

Selectively permeable membranes surrounding an osmotically active driving compound are also suitable for orally administered compositions. Fluid from the environment surrounding the capsule is imbibed by the driving compound, which swells to displace the GLP-2 molecule through an aperture, can provide an essentially zero order delivery profile instead of the spiked profiles of immediate release formulations. A time delay material such as, but not limited to, glycerol monostearate or glycerol stearate can also be used.

Suitable pharmaceutical carriers also include starch, glucose, lactose, sucrose, gelatin, saline, gum acacia, talc, keratin, urea, malt, rice, flour, chalk, silica gel, sodium stearate, glycerol monostearate, talc, sodium chloride, dried skim milk, glycerol, propylene, glycol, water, and ethanol. If desired, the carrier, can also contain minor amounts of wetting or emulsifying agents, or pH buffering agents. In addition, auxiliary, stabilizing, thickening, lubricating, and coloring agents may be used. The composition can be formulated as a suppository, with traditional binders and carriers such as triglycerides.

A pharmaceutical composition comprising a GLP-2 molecule or GLP-2 activator can be administered via one or more routes such as, but not limited to, oral, intravenous infusion, subcutaneous injection, intramuscular, topical, depo injection, implantation, time-release mode, and intracavitary. The pharmaceutical composition is formulated to be compatible with its intended route of administration. Examples of routes of administration include parenteral, e.g., intravenous, intramuscular, intraperitoneal, intracapsular, intraspinal, intrastemal, intratumor, intranasal, epidural, intra-arterial, intraocular, intraorbital, intradermal, subcutaneous, oral (e.g., inhalation), transdermal (topical—particularly to the ears, nose, eyes, or skin), transmucosal (e.g., oral) nasal, rectal, intracerebral, intravaginal, sublingual, submucosal, and transdermal administration.

Administration can be via any route known to be effective by a physician of ordinary skill. Parenteral administration, i.e., not through the alimentary canal, can be performed by subcutaneous, intramuscular, intra-peritoneal, intratumoral, intradermal, intracapsular, intra-adipose, or intravenous injection of a dosage form into the body by means of a sterile syringe, optionally a pen-like syringe, or some other mechanical device such as an infusion pump. A further option is a composition that can be a powder or a liquid for the administration in the form of a nasal or pulmonary spray. As a still further option, the administration can be transdermally, e.g., from a patch. Compositions suitable for oral, buccal, rectal, or vaginal administration can also be provided.

In one embodiment, a pharmaceutical composition of the invention is delivered by a controlled-release system. For example, the pharmaceutical composition can be administered using intravenous infusion, an implantable osmotic pump, a transdermal patch, liposomes, or other modes of administration. In one embodiment, a pump can be used (See e.g., Langer, 1990, Science 249:1527-33; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, the compound can be delivered in a vesicle, in particular a liposome (See e.g., Langer, 1990, Science 249:1527-33; Treat et al., 1989, in *Liposomes in the Therapy of Infectious Disease and Cancer*, Lopez-Berestein and Fidler (eds.), Liss, New York, pp. 353-65; Lopez-Berestein, ibid., pp. 317-27; International Patent Publication No. WO 91/04014; U.S. Pat. No. 4,704, 355). In another embodiment, polymeric materials can be used (See e.g., *Medical Applications of Controlled Release*, Langer and Wise (eds.), CRC Press: Boca Raton, Fla., 1974; *Controlled Drug Bioavailability, Drug Product Design and Performance*, Smolen and Ball (eds.), Wiley: New York (1984); Ranger and Peppas, 1953, J. Macromol. Sci. Rev. Macromol. Chem. 23:61; Levy et al., 1985, Science 228: 190; During et al., 1989, Ann. Neurol. 25:351; Howard et al., 1989, J. Neurosurg. 71:105).

In yet another embodiment, a controlled release system can be placed in proximity of the target. For example, a micropump can deliver controlled doses directly into bone or adipose tissue, thereby requiring only a fraction of the systemic dose (See e.g., Goodson, 1984, in *Medical Applications of Controlled Release*, vol. 2, pp. 115-138). In another example, a pharmaceutical composition of the invention can be formulated with a hydrogel (See, e.g., U.S. Pat. Nos. 5,702,717; 6,117,949; 6,201,072).

In one embodiment, it may be desirable to administer the pharmaceutical composition of the invention locally, i.e., to the area in need of treatment. Local administration can be achieved, for example, by local infusion during surgery, topical application (e.g., in conjunction with a wound dressing after surgery), injection, catheter, suppository, or implant. An implant can be of a porous, non-porous, or gelatinous material, including membranes, such as sialastic membranes, or fibers.

In certain embodiments, it may be desirable to introduce the GLP-2 molecules and GLP-2 activators into the central nervous system by any suitable route, including intraventricular, intrathecal, and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant.

In one embodiment, the invention provides for the treatment of a patient using implanted cells that have been regenerated or stimulated to proliferate in vitro or in vivo prior to reimplantation or transplantation into a recipient. Conditioning of the cells ex vivo can be achieved simply by growing the cells or tissue to be transplanted in a medium that has been supplemented with a growth-promoting amount of the combinations and is otherwise appropriate for culturing of those cells. The cells can, after an appropriate conditioning period, then be implanted either directly into the patient or can be encapsulated using established cell encapsulation technology, and then implanted.

The skilled artisan can appreciate the specific advantages and disadvantages to be considered in choosing a mode of administration. Multiple modes of administration are encompassed by the invention. For example, a GLP-2 molecule of the invention can be administered by subcutaneous injection, whereas another therapeutic agent can be administered by intravenous infusion. Moreover, administration of one or more species of GLP-2, with or without other therapeutic agents, can occur simultaneously (i.e., co-administration) or sequentially. In another embodiment, the periods of administration of a GLP-2 molecule or GLP-2 activator, with or without other therapeutic agents can overlap. For example a GLP-2 molecule or GLP-2 activator can be administered for 7 days and another therapeutic agent can be introduced beginning on the fifth day of GLP-2 treatment. Treatment with the other therapeutic agent can continue beyond the 7-day GLP-2 treatment.

A pharmaceutical composition of a GLP-2 molecule or GLP-2 activator can be administered before, during, and/or after the administration of one or more therapeutic agents. In one embodiment, a GLP-2 molecule or GLP-2 activator can first be administered to stimulate the expression of insulin, which increases sensitivity to subsequent challenge with a therapeutic agent. In another embodiment, a GLP-2 molecule or GLP-2 activator can be administered after administration of a therapeutic agent. In yet another embodiment, there can be a period of overlap between the administration of the GLP-2 molecule or GLP-2 activator and the administration of one or more therapeutic agents.

A pharmaceutical composition of the invention can be administered in the morning, afternoon, evening, or diurnally. In one embodiment, the pharmaceutical composition is administered at particular phases of the circadian rhythm. In a specific embodiment, the pharmaceutical composition is administered in the morning. In another specific embodiment, the pharmaceutical composition is administered at an artificially induced circadian state.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (See e.g., U.S. Pat. No. 5,698,155). Other examples of suitable pharmaceutical carriers are described in *Remington 's Pharmaceutical Sciences*, Alfonso R. Gennaro ed., Mack Publishing Co. Easton, Pa., 19$^{th}$ ed., 1995, pp. 1447 to 1676, incorporated herein by reference.

Accordingly, the pharmaceutical compositions herein described can be in the form of oral tablets, capsules, elixirs, syrups and the like.

For instance, for oral administration in the form of a tablet or capsule, the active drug component can be combined with an oral, non-toxic, pharmaceutically acceptable, inert carrier such as, but not limited to, lactose, starch, sucrose, glucose, methyl cellulose, magnesium stearate, dicalcium phosphate, calcium sulfate, mannitol, and sorbitol. For oral administration in liquid form, the oral drug components can be combined with any oral, non-toxic, pharmaceutically acceptable carrier such as, but not limited to, ethanol, glycerol, and water. Moreover, suitable binders, lubricants, disintegrating agents and coloring agents can also be incorporated into the mixture. Suitable binders include, but are not limited to, starch, gelatin, natural sugars (e.g., glucose, beta-lactose), corn sweeteners, natural and synthetic gums (e.g., acacia, tragacanth, sodium alginate), carboxymethylcellulose, polyethylene glycol, and waxes. Lubricants useful for an orally administered drug, include, but are not limited to, sodium oleate, sodium stearate, magnesium stearate, sodium benzoate, sodium acetate, and sodium chloride. Disintegrators include, but are not limited to, starch, methyl cellulose, agar, bentonite, and xanthan gum.

Pharmaceutical compositions adapted for oral administration can be provided, for example, as capsules or tablets; as powders or granules; as solutions, syrups or suspensions (in aqueous or non-aqueous liquids); as edible foams or whips; or as emulsions. For oral administration in the form of a tablet or capsule, the active drug component can be combined with an oral, non-toxic, pharmaceutically acceptable, inert carrier such as, but not limited to, lactose, starch, sucrose, glucose, methyl cellulose, magnesium stearate, dicalcium phosphate, magnesium carbonate, stearic acid or salts thereof, calcium sulfate, mannitol, and sorbitol. For oral administration in the form of a soft gelatine capsule, the active drug component can be combined with an oral, non-toxic, pharmaceutically acceptable, inert carrier such as, but not limited to, vegetable oils, waxes, fats, semi-solid, and liquid polyols. For oral administration in liquid form, the oral drug components can be combined with any oral, non-toxic, pharmaceutically acceptable carrier such as, but not limited to, ethanol, glycerol, polyols, and water. Moreover, suitable binders, lubricants, disintegrating agents and coloring agents can also be incorporated into the mixture. Suitable binders include, but are not limited to, starch, gelatin, natural sugars (e.g., glucose, beta-lactose), corn sweeteners, natural and synthetic gums (e.g., acacia, tragacanth, sodium alginate), carboxymethylcellulose, polyethylene glycol, and waxes. Lubricants useful for an orally administered drug, include, but are not limited to, sodium oleate, sodium stearate, magnesium stearate, sodium benzoate, sodium acetate, and sodium chloride. Disintegrators include, but are not limited to, starch, methyl cellulose, agar, bentonite, and xanthan gum.

Orally administered compositions may contain one or more agents, for example, sweetening agents such as, but not limited to, fructose, ASPARTAME and saccharin. Orally administered compositions may also contain flavoring agents such as, but not limited to, peppermint, oil of wintergreen, and cherry. Orally administered compositions may also contain coloring agents and/or preserving agents.

The GLP-2 molecules and GLP-2 activators can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. A variety of cationic lipids can be used in accordance with the invention including, but not limited to, N-(1(2,3-dioleyloxy)propyl)-N,N,N-trimethylammonium chloride ("DOTMA") and diolesylphosphotidylethanolamine ("DOPE"). Such compositions suit the mode of administration.

GLP-2 molecules and GLP-2 activators can also be delivered by the use of monoclonal antibodies as individual carriers to which the GLP-2 molecules and GLP-2 activators can be coupled. The GLP-2 molecules and GLP-2 activators can also be coupled with soluble polymers as targetable drug carriers. Such polymers can include polyvinylpyrrolidone, pyran copolymer, polyhydroxypropylmethacrylamide-phenol, polyhydroxyethylaspartamide-phenol, or polyethyleneoxide-polylysine substituted with palmitoyl residues. Furthermore, the GLP-2 molecules and GLP-2 activators can be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

Pharmaceutical compositions adapted for parenteral administration include, but are not limited to, aqueous and non-aqueous sterile injectable solutions or.suspensions, which can contain antioxidants, buffers, bacteriostats and solutes that render the pharmaceutical compositions substantially isotonic with the blood of an intended recipient. Other components that can be present in such pharmaceutical compositions include water, alcohols, polyols, glycerine and vegetable oils, for example. Compositions adapted for parenteral administration can be presented in unit-dose or multi-dose containers (e.g., sealed ampules and vials), and can be stored in a freeze-dried (i.e., lyophilized) condition requiring the addition of a sterile liquid carrier (e.g., sterile saline solution for injections) immediately prior to use. Extemporaneous injection solutions and suspensions can be prepared from sterile powders, granules and tablets.

Pharmaceutical compositions adapted for transdermal administration can be provided as discrete patches intended to remain in intimate contact with the epidermis for a prolonged period of time. Pharmaceutical compositions adapted for topical administration can be provided as, for example, ointments, creams, suspensions, lotions, powders, solutions, pastes, gels, sprays, aerosols or oils. A topical ointment or cream is preferably used for topical administration to the skin, mouth, eye or other external tissues. When formulated in an ointment, the active ingredient can be employed with either a paraffinic or a water-miscible ointment base. Alternatively, the active ingredient can be formulated in a cream with an oil-in-water base or a water-in-oil base.

Pharmaceutical compositions adapted for topical administration to the eye include, for example, eye drops or injectable pharmaceutical compositions. In these pharmaceutical compositions, the active ingredient can be dissolved or suspended in a suitable carrier, which includes, for example, an aqueous solvent with or without carboxymethylcellulose. Pharmaceutical compositions adapted for topical administration in the mouth include, for example, lozenges, pastilles and mouthwashes.

Pharmaceutical compositions adapted for nasal administration can comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, pharmaceutical compositions adopted for nasal administration can comprise liquid carriers such as, for example, nasal sprays or nasal drops. These pharmaceutical compositions can comprise aqueous or oil solutions of a GLP-2 molecule. Compositions for administration by inhalation can be supplied in specially adapted devices including, but not limited to, pressurized aerosols, nebulizers or insufflators, which can be constructed so as to provide predetermined dosages of the GLP-2 molecule or GLP-2 activator.

Pharmaceutical compositions adapted for rectal administration can be provided as suppositories or enemas. Pharmaceutical compositions adapted for vaginal administration can be provided, for example, as pessaries, tampons, creams, gels, pastes, foams or spray formulations.

Suppositories generally contain active ingredients in the range of 0.5% to 10% by weight. Oral formulations preferably contain 10% to 95% active ingredient by weight. In a preferred embodiment, the composition is formulated in accordance with routine procedures as a pharmaceutical composition adapted for intratumoral injection, implantation, subcutaneous injection, or intravenous administration to humans.

Typically, pharmaceutical compositions for injection or intravenous administration are solutions in sterile isotonic aqueous buffer. Where necessary, the composition can also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent.

Where the composition is to be administered by infusion, it can be dispensed with an infusion bottle, bag, or other acceptable container, containing sterile pharmaceutical grade water, saline, or other acceptable diluents. Where the composition is administered by injection, an ampule of sterile water for injection or saline can be provided so that the ingredients may be mixed prior to administration.

Methods and compositions for administration disclosed in relation to GLP-2 above are applicable equally to combination therapies disclosed herein.

The GLP-2 molecules and GLP-2 activators and optionally another therapeutic agent are administered at an effective dose. The dosing and regimen most appropriate for patient treatment will vary with the disease or condition to be treated, and in accordance with the patient's weight and with other parameters.

An effective dosage and treatment protocol can be determined by conventional means, comprising the steps of starting with a low dose in laboratory animals, increasing the dosage while monitoring the effects (e.g., histology, disease activity scores), and systematically varying the dosage regimen. Several factors may be taken into consideration by a clinician when determining an optimal dosage for a given patient. Primary among these is the amount of GLP-2 molecule normally circulating in the plasma, which, in the case of a GLP-2 peptide, is approximately 150 pmol/ml in the resting state, and rising to approximately 225 pmol/ml after nutrient ingestion for healthy adult humans (Orskov and Holst, 1987, Scand J. Clin. Lab. Invest. 47:165). Additional factors include, but are not limited to, the size of the patient, the age of the patient, the general condition of the patient, the particular disease being treated, the severity of the disease, the presence of other drugs in the patient, and the in vivo activity of the GLP-2 molecule.

Trial dosages would be chosen after consideration of the results of animal studies and the clinical literature. A person of ordinary skill in the art can appreciate that information such as binding constants and Ki derived from in vitro GLP-2 binding competition assays may also be used in calculating dosages.

A typical effective human dose of a GLP-2 molecule or GLP-2 activator would be from about 10 μg/kg body weight/day to about 10 mg/kg/day, preferably from about 50 μg/kg/day to about 5 mg/kg/day, and most preferably about 100 μg/kg/day to 1 mg/kg/day. As analogs of the GLP-2 molecules and GLP-2 activators disclosed herein can be 2 to 100 times more potent than naturally occurring counterparts, a typical effective dose of such a GLP-2 analog can be lower, for example, from about 100 ng/kg body weight/day to 1 mg/kg/day, preferably 1 ttg/kg/day to 500 μg/kg/day, and even more preferably 1 μg/kg/day to 100 μg/kg/day.

In another embodiment, the effective dose of a GLP-2 molecule or a GLP-2 activator is less than 10 μg/kg/day. In yet another embodiment the effective dose of a GLP-2 molecule or GLP-2 activator is greater than 10 mg/kg/day.

The specific dosage for a particular patient, of course, has to be adjusted to the degree of response, the route of administration, the patients weight, and the patient's general condition, and is finally dependent upon the judgment of the treating physician.

5.6 Gene Therapy.

Gene therapy approaches can also be used in accordance with the present invention to modulate the expression of a GLP-2 molecule or GLP-2 activator and accordingly, to treat or prevent a bone-related disorder or a calcium homeostasis related syndrome.

Any of the methods for gene therapy available in the art can be used in accordance with the present invention (See, e.g., Goldspiel et al., 1993, Clin. Pharm. 12:488-505; Grossman and Wilson, 1993, Curr. Opin. Genet. Devel. 3:110-114; Salmons and Gunzberg, 1993, Hum. Gene Ther. 4:129-141; Morgan and Anderson, 1993, Ann. Rev. Biochem. 62:191-217; Mulligan, 1993, Science 260:926-932; Tolstoshev, 1993, Ann. Rev. Pharmacol. Toxicol. 32:573-596; and Clowes et al., 1994, J. Clin. Invest. 93:644-651; Kiem et al., 1994, Blood 83:1467-1473, each of which is incorporated herein by reference).

Long-term effective use of a gene therapy vector to ameliorate disease in large mammals has been demonstrated. For example, administration of an AAV containing a wild-type gene to dogs suffering from Leber congenital amaurosis, a condition that results in blindness due to a mutation of a gene (RPE65) in the retinal pigrnent epithelium, has successfully corrected the genetic defect (Ackland et al., 2001, Nat. Genet. 28:92). Expression of the wild-type RPE65 gene was confirmed by RT PCR and restoration of function was demonstrated by electrophysiological studies of the retina, as well as by unbiased observational studies of the treated dogs. The treatment was shown to be effective for at least four months. Intramuscular administration of an AAV encoding for factor IX to treat dogs suffering from hemophilia has also been reported (Herzog et al., 1999, Nat. Med. 5:56). Administration of AAV encoding factor IX was shown to significantly reduce clotting time in treated dogs for 17 months. Thus, such examples demonstrate that gene therapy can be used to restore lost genetic function in a large animal model using treatment methods known in the art.

Gene therapy refers to therapy performed by administering to a patient an expressed or expressible nucleic acid. Gene therapy involves introducing a gene construct to cells in tissue culture or in vivo.

The recipient's cells or heterologous cells can be engineered to express one or more of the GLP-2 molecules and GLP-2 activators or a combination of a GLP-2 molecule or GLP-2 activator and another therapeutic agent. Methods for introduction of nucleic acid sequences encoding GLP-2 molecules or GLP-2 activators (See, e.g., Bell et al., 1983, Nature 304: 5924) to cells in vitro include, but are not limited to, electroporation, lipofection, DEAE-Dextran transfection, calcium phosphate-mediated transfection, liposome-mediated transfer, and viral infection.

Such ex vivo treatment protocols can be used to transfer DNA into a variety of different cell types including, but not limited to, epithelial cells (U.S. Pat. No. 4,868,116; Morgan and Mulligan WO87/00201; Morgan et al., 1987, Science 237:1476-1479; Morgan and Mulligan, U.S. Pat. No.4,980, 286), endothelial cells (WO89/05345), fibroblasts (Palmer et al., 1987, Proc. Natl. Acad. Sci. 84:1055-1059; Anson et al., 1987, Mol. Biol. Med. 4:11-20; Rosenberg et al., 1988, Science 242:1575-1578; U.S. Pat. No. 4,963,489), lymphocytes (U.S. Pat. No. 5,399,346; Blaese et al., 1995, Science 270:475-480), and hematopoietic stem cells (Lim et al., 1989, Proc. Natl. Acad. Sci. 86:8892-8896; U.S. Pat. No. 5,399,346).

Accordingly, one can use gene therapy to create a cell line that produces any GLP-2 molecule or GLP-2 activator. Additionally, cells can be engineered to produce a GLP-2 molecule or GLP-2 activator alone or in combination with another agent such as, but not limited to, a peptide hormone (e.g., IGF-1, IGF-2 or growth hormone). The cells can be grown as an implant in an experimental animal or in tissue culture using techniques known in the art. Various expression vectors, including viral vectors, suitable for introduction of genetic information into human cells, can be used to incorporate the constructs encoding the GLP-2 molecule or GLP-2 activator and/or the other therapeutic agent. Once altered genetically, the engineered cells can then be administered to a subject using procedures known in the art.

Alternatively, one can use gene therapy to transfect the recipient's cells in vivo. Methods of administering vectors that transfect cells in vivo are known in the art. Formulations of nucleic acid for such in vivo methods can be, but are not limited to, naked DNA; nucleic acid encapsulated into liposomes or liposomes combined with viral envelope receptor proteins (Nicolau et al., 1983, Proc. Natl. Acad. Sci. 80:1068), DNA coupled to a polylysine-glycoprotein carrier complex, and nucleic acid precipitants.

Nucleic acid preparations can be introduced in vivo using any one of the techniques known in the art such as direct injection, electroporation, and particle bombardment. In addition, "gene guns" have been used for gene delivery into cells (Australian Patent No. 9068389).

Synthetic genes which result in the production of a GLP-2 molecule of GLP-2 activator following either in vitro or in vivo transcription and translation can be constructed using techniques well known in the art (See, e.g., Ausubel et al., 1990, Current Protocols in Molecular Biology p. 8.2.8 to 8.2.13.; Ausubel et al., 1995, Short Protocols in Molecular Biology p. 8.8-8.9, John Wiley & Sons Inc.).

A GLP-2 antagonist can be inhibited with a GLP-2 activator (i.e., an inhibitor of a GLP-2 antagonist) with the use of gene therapy (e.g., antisense, ribozyme, triple helix molecules, and/or recombinant antibodies). In this embodiment, introduction of the GLP-2 activator into a patient results in a decrease in the respective GLP-2-antagonist-gene expression and/or GLP-2 antagonist protein levels. Techniques for the production and use of antisense, ribozyme, and/or triple helix molecules are well known to those of skill in the art, and in accordance with the present invention.

The present invention encompasses vectors comprising a nucleic acid encoding a polypeptide or peptide GLP-2 molecule or GLP-2 activator of the invention. In one embodiment, a nucleic acid encoding a GLP-2 molecule or GLP-2 activator to be introduced for purposes of gene therapy comprises an inducible promoter operably linked to the coding region, such that expression of the nucleic acid can be controlled using an appropriate inducer or inhibitor of transcription. In another embodiment, the vector contains a promoter, which expresses the cloned construct constitutively. In a further embodiment, the promoter can be down-regulated using a suppressor molecule. Alternatively, the vector contains a promoter, such that an inducing molecule initiates or increases expression of the cloned nucleic acid. In a preferred embodiment, the vector contains a cell-specific promoter. In another preferred embodiment, the vector contains a disease-specific promoter, such that expression is largely limited to diseased tissues or tissues surrounding diseased tissues.

Usually, the method of cellular introduction also comprises the transfer of a selectable marker to the cells, after which the cells are placed under selection to isolate the cells that have taken up and that express the transferred gene. These transfected cells can be administered to a patient.

Several methods have been developed for delivering the nucleic acid molecules to target cells or target tissues. Accordingly, the nucleic acid molecules can be delivered in vivo or ex vivo to target cells. In one embodiment, an expression construct can be delivered directly into a patient. In a particular embodiment, the nucleic acid molecules of the GLP-2 molecule or GLP-2 activator can be injected directly into the target tissue or cell derivation site. Alternatively, a patient's cells are first transfected with an expression construct in vitro, after which the transfected cells are administered back into the subject (i.e., ex vivo gene therapy).

In one embodiment, a vector is introduced in vivo such that it is taken up by a cell and directs the transcription of a nucleic acid of the invention. Such a vector can remain episomal or can become chromosomally integrated. Expression vectors can be plasmid, viral, or others known in the art, that can be used to replicate and/or express the cloned nucleotide sequence encoding a GLP-2 nucleic acid in a target mammalian cell. A variety of expression vectors useful for introducing into cells the nucleic acid molecules are well known in the art (e.g., pCI, pVPack, pCMV, pSG5). Expression constructs can be introduced into target cells and/or tissues of a subject using vectors which including but not limited to, adenovirus, adeno-associated virus, retrovirus and herpes virus vectors, in addition to other particles that introduce DNA into cells, such as liposomes.

In a particular embodiment, the nucleic acid molecules can be introduced into the target tissue as an implant, for example, in a polymer formulation (See, e.g., U.S. Pat. No. 5,702,717). In another embodiment, the nucleic acid molecules can be targeted to the desired cells or tissues.

A nucleic acid sequence can be expressed using any promoter known in the art capable of expression in mammalian, preferably human cells. Such promoters can be inducible or constitutive. These promoters include, but are not limited to, the SV40 early promoter region (Bemoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. 78:1441-1445), and the regulatory sequences of the metallothionein gene (Brinster et al., 1982, Nature 296:39-42). Tissue-specific promoters include the promoter region of osteocalcin.

In one embodiment, in which recombinant cells are used in gene therapy, nucleic acid sequences encoding polypeptides of the invention are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention, such as, but not limited to, hematopoietic cells, neuronal progenitor cells, hepatic progenitor cells, osteoblasts, and fetal stem cells (See, e.g., PCT Publication WO 94/08598; Stemple and Anderson, 1992, Cell 71:973-985; Pittelkow and Scott, 1986, Mayo Clinic Proc. 61:771; Rheinwald, 1980, Meth Cell Bio. 21A:229).

In other embodiments, the nucleic acid of the invention can include other appended groups such as peptides (e.g., for targeting host cell receptors in vivo), or agents facilitating transport across the cell membrane (see, e.g., Letsinger et al., 1989, Proc. Natl. Acad. Sci. 86:6553-6556; Lemaitre et al., 1987, Proc. Natl. Acad. Sci. 84:648-652; PCT Publication No. WO 88/09810) or the blood-brain barrier (See, e.g., PCT Publication No. WO 89/10134). For example, PCT Publication No. WO 88/09810 discloses nucleic acid conjugates comprising a relatively short oligonucleotide sequence, a linking group, and group which modifies the hydrophilic lipophilic balance to provide an amphiphillic product that aids in the transport of the conjugate across the cellular membrane. Another example, PCT Publication No. WO 89/10134, discloses chimeric peptides which are adapted to deliver a neuropharmaceutical agent, conjugated with a transportable peptide, into the brain by transcytosis across the blood-brain barrier. In addition, oligonucleotides can be modified with hybridization-triggered cleavage agents (See, e.g., Krol et al., 1988, BioTech. 6:958-976) or intercalating agents (See, e.g., Zon, 1988, Pharm. Res. 5:539-549). To this end, the oligonucleotide can be conjugated to another molecule, e.g., a peptide, hybridization triggered cross-linking agent, transport agent, or hybridization-triggered cleavage agent.

The nucleic acid molecules can be inserted into vectors and used as gene therapy vectors. Gene therapy vectors can be delivered to a subject by, for example, intravenous injection, local administration (U.S. Pat. No. 5,328,470) or by stereotactic injection (See, e.g., Chen et al., 1994, Proc. Natl. Acad. Sci. 91:3054-3057). The pharmaceutical preparation of the gene therapy vector can include the gene therapy vector in an acceptable diluent, or can comprise a slow release matrix in which the vector is s imbedded. Alternatively, where the vector can be produced intact from recombinant cells, e.g., retroviral vectors, the pharmaceutical preparation can include one or more cells producing the vector.

Any type of plasmid, cosmid, YAC or viral vector can be used to prepare the recombinant construct. Alternatively, vectors can be used which selectively target a tissue or cell type, e.g., viruses that infect bone cells. Further specificity can be realized by using a tissue-specific or cell-specific promoter in the expression vector.

In a specific embodiment, an expression vector is administered directly in vivo, where the vector is expressed to produce the encoded product. This can be accomplished by any of numerous methods known in the art, e.g., by placing a nucleic acid of the invention in an appropriate expression vector such that, upon administration, the vector becomes intracellular and expresses a nucleic acid of the invention. Such vectors can be internalized by using, for example, a defective or attenuated retroviral vector or other viral vectors that can infect mammalian cells (See e.g., U.S. Pat. No. 4,980,286).

Alternatively, an expression construct containing a nucleic acid of the invention can be injected directly into a target tissue as naked DNA. In another embodiment, an expression construct containing a nucleic acid of the invention can be introduced into a cell using microparticle bombardment, for example, by using a Biolistic gene gun (DuPont, Wilmington, Del.). In another embodiment, an expression construct containing a nucleic acid of the invention can be coated with lipids, or cell-surface receptors, or transfecting agents, such that encapsulation in liposomes, microparticles, or microcapsules facilitates access to target tissues and/or entry into target cells.

In yet another embodiment, an expression construct containing a nucleic acid of the invention is linked to a polypeptide that is internalized in a subset of cells or is targeted to a particular cellular compartment. In a further embodiment, the linked polypeptide is a nuclear targeting sequence that targets the vector to the cell nucleus. In another further embodiment, the linked polypeptide is a ligand that is internalized by receptor-mediated endocytosis in cells expressing the respective receptor for the ligand (See e.g., Wu and Wu, 1987, J. Biol. Chem. 262:4429-4432).

In another embodiment, nucleic acid-ligand complexes can be formed such that the ligand comprises a fusogenic viral peptide, which disrupts endosomes, thereby allowing the nucleic acid to avoid lysosomal degradation. In another embodiment, a nucleic acid of the invention can be targeted in vivo via a cell-specific receptor resulting in cell-specific uptake and expression (See e.g., International Patent Publications WO 92/06180, WO 92/22635, WO 92/20316, and WO 93/14188). For example, WO 92/06180 discloses that a virus or cell can be targeted to a target cell for internalization in vivo by introducing a receptor-specific molecule onto the surface of the virus or cell to produce a modified virus or cell which specifically binds to a receptor on the surface of the target cell, resulting in internalization by the target cell. Another example, WO 93/14188, discloses the use of a genetically engineered retroviral packaging cell line that has altered the viral envelope such that it contains a peptide that will bind to a molecule on the membrane of the target cell for the transfer of genetic information. Still other examples, WO 92/22635 and WO 92/20316, disclose a molecular complex for targeting a gene to a specific cell in vivo comprising an expressible gene complexed to a carrier that is a conjugate of a gene binding agent and a cell-specific binding agent, which is specific for a receptor that mediates internalization of bound ligands by endocytosis.

In yet another embodiment, a nucleic acid of the invention is introduced intracellularly and, by homologous recombination, can transiently or stably be incorporated within the host cell DNA, which then allows for its expression, (Koller and Smithies, 1989, Proc. Natl. Acad. Sci. 86:8932-8935; Zijlstra et al., 1989, Nature 342:435438).

In one embodiment, viral vectors are used that contain nucleic acids encoding compounds that activate cytokine receptors (i.e., cytokines or antibodies), or compounds that activate molecules expressed on activated immune cells (See, e.g., Miller et al., 1993, Meth. Enzymol. 217:581-599). In a specific embodiment, a viral vector that contains nucleic acid sequences encoding 4-1BB ligand, or anti-4-1 BB immunoglobulin, and/or IL-12 are used. For example, a retroviral vector can be used in which sequences not necessary for packaging of the viral genome and integration into host cell DNA have been deleted, and nucleic acid sequences encoding 4-1BB ligand, or anti-4-1BB immunoglobulin, or IL-12 are cloned into the vector, thereby facilitating delivery of the transgene into a subject. Greater detail about retroviral vectors is available in Boesen et al., 1994, Biotherapy 6:291-302, which describes the use of a retroviral vector to deliver the mdrl gene to hematopoietic stem cells.

Other viral vectors can be used for gene therapy approaches in accordance with the invention. For example, adenoviruses are useful for delivering gene constructs to respiratory epithelia. Other targets for adenovirus-based delivery systems are the liver, the central nervous system, endothelial cells, and muscle cells. Moreover, adenoviruses are able to infect non-dividing cells (See, e.g., Rosenfeld et al., 1991, Science 252:431-434; Rosenfeld et al., 1992, Cell 68:143-155; Mastrangeli et al., 1993, J. Clin. Invest. 91:225-234; Kozarsky and Wilson, 1993, Curr. Opin. Genet. Develop. 3:499-503; Bout et al., 1994, Hum. Gene Ther. 5:3-10; PCT Publication No. WO 94/12649; and Wang et al., 1995, Gene Ther. 2:775-783).

Accordingly, adeno-associated virus can also be used in the gene therapy approaches of the present invention (See, e.g., Walsh et al., 1993, Proc. Soc. Exp. Biol. Med. 204:289-300; U.S. Pat. No. 5,436,146).

In this embodiment, the nucleic acid is introduced into a cell prior to administration in vivo of the resulting recombinant cell. Such introduction can be carried out by any method known in the art, including, but not limited to, transfection, electroporation, microinjection, infection with a viral or bacteriophage vector containing the nucleic acid sequences, cell fusion, chromosome-mediated gene transfer, microcell-mediated gene transfer, and spheroplast fusion. Numerous techniques are known in the art for the introduction of foreign genes into cells (See, e.g., Maniatis et al., 1989; Current Protocols, 2000; Loeffler and Behr, 1993, Meth. Enzymol. 217:599-618; Cohen et al., 1993, Meth. Enzymol. 217:618-644; Cline, 1985, Pharmacol. Ther. 29:69-92) and can be used in accordance with the present invention. In a preferred embodiment, the technique stably transfers a nucleic acid of the invention to a target cell, such that the nucleic acid is inherited by the cell's progeny.

The resulting recombinant cells can be delivered to a subject by various methods known in the art, and the skilled artisan would appreciate appropriate modes of administration. For example, intravenous administration may be the preferred mode of administration for recombinant hematopoietic stem cells. The number of recombinant cells to be administered to a subject can be determined by one skilled in the art, and would include a consideration of factors such as the desired effect, the disease state, and the mode of administration.

Cells into which a nucleic acid of the invention can be introduced for purposes of gene therapy include, but are not limited to, epithelial cells, endothelial cells, keratinocytes, fibroblasts, muscle cells, hepatocytes, blood cells (e.g., B lymphocytes, T lymphocytes, eosinophils, granulocytes, macrophages, megakaryocytes, monocytes, neutrophils), stem cells or progenitor cells (e.g., undifferentiated cells obtained from adipose, bone marrow, blood, fetal liver, and umbilical cord (See, e.g., Rheinwald, 1980, Meth. Cell Bio. 21A:229; International Publication No. WO 94/08598; Pittelkow and Scott, 1986, Mayo Clinic Proc. 61:771; and Stemple and Anderson, 1992, Cell 71:973-985). The cells used for introduction of a nucleic acid of the invention can be autologous or non-autologous. In a preferred embodiment, the cells used for gene therapy are autologous to the subject.

One skilled in the art will appreciate that many different promoters can be used to drive expression of a nucleic acid of the invention. In one embodiment, the promoter comprises hormone-sensitive elements. For example, a promoter containing an androgen-sensitive enhancer would be activated to a greater degree in androgen-producing cells or adjacent tissues. Such an expression construct may be beneficial for targeting tissues secreting abnormally high levels of androgen. In another embodiment, the promoter comprises elements of a fibroblast-specific promoter. In a further embodiment, the fibroblast-specific promoter comprises promoter elements from synovial fibroblasts. Alternatively, the promoter comprises elements of promoters that are activated in aggressive rheumatoid arthritis synovial fibroblasts. In a particular embodiment, the promoter comprises a portion of a proglucagon promoter. In a non-limiting example, a viral vector is used in which the viral promoter is replaced fully, or in part, with at least parts of a proglucagon promoter. Such an expression construct would more specifically be expressed in proglucagon-expressing cells.

Gene therapy approaches can also be used in accordance with the present invention to inhibit antagonists of GLP-2, particularly DPP-IV. For example, ribozyme and triple helix molecules can be used to target gene products of a GLP-2 inhibitor, or of an aberrant GLP-2 gene, resulting in a decrease in GLP-2 inhibitor protein or aberrant GLP-2 protein. Techniques for the production and use of antisense ribozyme and/or triple helix molecules are well known to those of skill in the art and can be designed with respect to the nucleotide sequence encoding the amino acid sequence of the target gene, also known in the art.

In another embodiment, mutations can be introduced into the gene encoding the GLP-2 receptor resulting in an altered sequence that activates the receptor thus simulating increased GLP-2 receptor binding (U.S. Pat. No. 6,077,949). The application of automated gene synthesis techniques provides an opportunity for generating sequence variants of the naturally occurring GLP-2 receptor gene. The skilled artisan can appreciate that polynucleotides coding for variants of the GLP-2 receptor can be generated by substitution of codons for those represented in the naturally occurring polynucleotide sequences provided herein. In addition, polynucleotides coding for synthetic variants of the GLP-2 receptor herein provided can be generated which incorporate from 1 to 20, e.g., from 1 to 5, amino acid substitutions, or deletions or additions. The modified GLP-2 receptor can be placed in an expression vector and administered to a subject in need of treatment to increase receptor activity in a desired tissue.

5.6.1 Antisense Therapy.

In one embodiment, an antisense approach to gene therapy can be used to treat a bone-related disorder or a calcium homeostasis related syndrome. Antisense approaches to gene therapy involve.the use of riboprobes that can hybridize to a portion of the target mRNA. Additionally, non-ribose antisense constructs are contemplated in the present invention including, but not limited to, peptide nucleic acids (PNA), LNA, phosphine analogues, phosphotionates, and PEGA modified antisense constructs. Preventing transcription of a GLP-2 antagonist will enhance GLP-2 activity. The skilled artisan will recognize that absolute complementarity is not required, such that some degree of mismatch can result in, at least, transitory duplex formation. In one non-limiting example, the antisense riboprobe binds to the target mRNA transcript and prevents its translation. In one embodiment, the target mRNA encodes a GLP-2 antagonist. In another embodiment, the target mRNA is an aberrant GLP-2 mRNA.

Riboprobes that are complementary to the 5' untranslated sequences, up to and including the AUG initiation codon, can be used effectively to inhibit translation of a GLP-2 mRNA. Riboprobes complementary to the 3' untranslated sequences of mRNAs also can be effective at inhibiting GLP-2 mRNA translation (See, e.g., Wagner, 1994, Nature 372:333-335). Moreover, antisense riboprobes complementary to mRNA coding regions can be used in accordance with the invention.

Preferably, in vitro studies are performed to assess the ability of an antisense riboprobe to inhibit gene expression. These studies typically use controls which distinguish between antisense-mediated inhibition of gene expression and nonspecific biological effects of riboprobes. Preferably, these studies compare antisense-mediated changes in the levels of the target RNA or target protein with levels of an internal control RNA or protein.

In one embodiment, a recombinant DNA construct comprising an antisense riboprobe under the control of a pol III or pol II promoter is used to generate antisense riboprobes in a cell. The use of such a construct to transfect target cells in the subject can result in the transcription of sufficient amounts of a riboprobe to reduce or inhibit mRNA and/or protein expression. In one embodiment, the mRNA is a GLP-2 inhibitor mRNA. In another embodiment, the mRNA is an aberrant GLP-2 mRNA. Low transfection rates or low transcription activity of the DNA construct can nevertheless generate sufficient antisense molecules to demonstrate clinical effectiveness.

In another embodiment, a GLP-2 inhibitor antisense nucleic acid sequence, or an aberrant GLP-2 antisense nucleic acid sequence, is cloned into an expression vector, preferably a mammalian expression vector.

In another embodiment, aberrant GLP-2 or GLP-2 inhibitor antisense nucleic acid molecules of the invention are cloned into a vector, which is designed to target the vector (and thereby target expression of the antisense riboprobe) to specific tissues or cell-types. For example, an antisense riboprobe can be linked to peptides or antibodies that specifically bind receptors or antigens expressed on the target cell surface, thereby targeting the vector to the cells.

In another embodiment, the vector comprises a promoter that is more highly activated in diseased cells or tissues, as compared to normal cells or tissues.

5.6.2 Ribozyme Therapy.

Ribozyme therapy can be used to treat a bone-related disorder or a calcium homeostasis related syndrome.

Ribozymes are enzymatic RNA molecules capable of catalyzing the specific cleavage of a single-stranded nucleic acid, such as an mRNA (See, e.g., Rossi, 1994, Curr. Biol. 4:469-471). The mechanism of ribozyme action involves sequence-specific hybridization of the ribozyme molecule to complementary target RNA, followed by an endonucleolytic cleavage. The composition of ribozyme molecules include one or more sequences complementary to the target gene mRNA, and catalytic sequences responsible for mRNA cleavage (see e.g., U.S. Pat. No. 5,093,246 which is incorporated by reference in its entirety). Thus, ribozymes (e.g., hammerhead ribozymes) can be used to catalytically cleave mRNA transcripts thereby inhibiting the expression of a protein encoded by a particular mRNA (See, e.g., Haselhoff and Gerlach, 1988, Nature 334:585-591). A ribozyme having specificity for a nucleic acid molecule encoding a polypeptide of the invention can be designed based upon the nucleotide sequence of the nucleic acid molecules of the invention. Accordingly, in one embodiment, an engineered hammerhead motif ribozyme molecule specifically and efficiently catalyzes endonucleolytic cleavage of RNA sequences encoding a GLP-2 antagonist of the invention.

In another embodiment, an mRNA encoding a polypeptide of the invention is used to select a catalytic RNA having a specific ribonuclease activity from a pool of RNA molecules (See, e.g., Bartel and Szostak, 1993, Science 261: 1411-1418).

Specific ribozyme cleavage sites within a potential RNA target are identified by scanning the molecule of interest for ribozyme cleavage sites, which include the sequences GUA, GUU and GUC. Once identified, short RNA sequences of approximately 15 to 20 ribonucleotides corresponding to a cleavage site of a target gene are evaluated for predicted structural features, such as secondary structure, that may make the oligo-nucleotide suitable. The suitability of candidate sequences also can be evaluated by testing their ability to hybridize with complementary oligonucleotides, using for example, ribonuclease protection assays.

5.6.3 Triple-Helix Therapy.

In one embodiment, nucleic acid molecules that form triple helical structures are used to treat a bone-related disorder or a calcium homeostasis related syndrome. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells (See, e.g., Helene, 1991, Antican. Drug Des. 6:569-584; Helene, 1992, Ann. N.Y. Acad. Sci. 660:27-36; Maher, 1992, Bioassays 14:807-815).

Nucleic acid molecules to be used to inhibit transcription by triple helix formation can be single stranded oligonucleotides. The base composition of these oligonucleotides can be designed to promote triple helix formation via Hoogsteen base pairing rules, preferably with long stretches of purines or pyrimidines on one strand of the duplex. Nucleotide sequences can be pyrimidine-based thereby resulting in TAT and CGC+triplet across the three associated strands of the resulting triple helix. The pyrimidine-rich molecules provide base complementarity to a purine-rich region of a single strand of the duplex in a parallel orientation to that strand. Purine-rich nucleic acid molecules also can be chosen, for example, containing a stretch of guanine residues. These molecules can form a triple helix with a DNA duplex that is rich in GC pairs, in which most of the purine residues are located on a single strand of the targeted duplex, resulting in GGC triplets across the three strands in the triplex.

Additionally, the number of potential sequences that can be targeted for triple helix formation can be increased by creating a "switchback" nucleic acid molecule. Switchback molecules are synthesized in an alternating 5'-3', 3'-5' manner, such that the molecule first hybridizes with one strand of a duplex, followed by hybridization with another strand, thus eliminating the requirement for a stretch of purines or pyrimidines on one strand of a duplex.

Ribozyme and triple helix molecules of the invention can be prepared by any method known in the art for the synthesis of DNA or RNA molecules (e.g., oligodeoxyribonucleotides or oligoribonucleotides). Such methods include, for example, solid phase phosphoramidite chemical synthesis.

These oligonucleotides can be administered directly, for example, via injection. Alternatively, RNA molecules can be generated in vitro or in vivo by transcription of DNA sequences. Such DNA sequences can be incorporated into a wide variety of vectors known in the art that feature a suitable RNA polymerase promoter such as, for example, a T7 or SP6 polymerase promoter. In a preferred embodiment, a bone-cell specific promoter is used to produce an expression vector comprising a nucleic acid sequence of the invention. In another preferred embodiment, a bone-specific promoter is used to produce an expression vector comprising a nucleic acid sequence of the invention.

5.6.4 Antibody Therapy.

The invention also encompasses the use of antibody therapy to treat a bone-related disorder or a calcium homeostasis related syndrome. In one embodiment, nucleic acid molecules comprising sequences encoding antibodies that bind to a GLP-2 antagonist are administered via gene therapy. In a particular embodiment, recombinant cells are used that contain nucleic acid sequences encoding antibodies to GLP-2 antagonist polypeptides of the invention. The gene construct is expressed such that the recombinant antibody is secreted or expressed on the cell surface. The recombinant cells are then administered in vivo for therapeutic effect.

GLP-2 antibodies of the invention, including antibodies conjugated to therapeutic moieties, can be administered to an individual alone or in combination with an s anti-osteoporosis agent, anti-obesity agent, growth factor or hormone. In one embodiment, an antibody directed to a GLP-2 inhibitor polypeptide is administered first, followed by an anti-osteoporosis agent, anti-obesity agent, growth factor, or hormone within 24 hours. The treatment cycle can be repeated if warranted by the clinical response of the patient. Furthermore, the antibody, anti-osteoporosis agent, growth factor, or hormone can be administered via separate routes, such as for example, by intravenous and intramuscular administration.

Still another aspect of the invention is a pharmaceutical composition comprising an antibody of the invention and a pharmaceutically acceptable carrier. In preferred embodiments, the pharmaceutical composition contains an antibody of the invention, a. GLP-2 molecule, and a pharmaceutically acceptable carrier.

5.6.5 Vaccine Therapy.

Vaccine therapy can be used to treat a bone-related disorder or a calcium homeostasis related syndrome. Vaccine therapy can be administered to a subject in need of such treatment, e.g., a subject expressing an aberrant GLP-2 variant or an aberrant intermediate in the GLP-2 cascade. The nucleotides of the invention, including variants and derivatives, can be used as vaccines, e.g., by genetic immunization. Genetic immunization is particularly advantageous as it stimulates a cytotoxic T-cell response but does not utilize live attenuated vaccines, which can revert to a virulent form and infect the host causing the very infection sought to be prevented. As used herein, genetic immunization comprises inserting the nucleotides of the invention into a host, such that the nucleotides are taken up by cells of the host and the proteins encoded by the nucleotides are translated. These translated proteins are then either secreted or processed by the host cell for presentation to immune cells and an immune reaction is stimulated. Preferably, the immune reaction is a cytotoxic T cell response; however, a humeral response or macrophage stimulation is also useful in preventing future infections. The skilled artisan will appreciate that there are various methods for introducing foreign nucleotides into a host animal and subsequently into cells for genetic immunization, for example, by intramuscular injection of about 50 mg of plasmid DNA encoding the proteins of the invention solubilized in 50 ml of sterile saline solution, with a suitable adjuvant (See, e.g., Weiner and Kennedy, 1999, Sci. Am. 7:50-57; Lowrie et al., 1999, Nature 400:269-271).

5.7 Kits.

The invention also encompasses kits for detecting the presence of a polypeptide or nucleic acid of the invention in a biological sample (a test sample). Such kits can be used to determine if a subject is suffering from or is at increased risk of developing a disorder associated with aberrant expression of a polypeptide of the invention as discussed, for example, in sections above relating to uses of the pharmaceutical compositions of the invention.

For example, kits can be used to determine if a subject is suffering from or is at increased risk of developing a bone-related disorder or a calcium homeostasis related syndrome.

In another example, kits can be used to determine if a subject is suffering from or is at risk for disorders that are associated with aberrant expression of a polypeptide of the invention.

The kit, for example, can comprise a labeled compound or agent capable of detecting the polypeptide or mRNA encoding the polypeptide in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for observing that the tested subject is suffering from or is at risk of developing a disorder associated with aberrant expression of the polypeptide if the amount of the polypeptide or mRNA encoding the polypeptide is above or below a normal level.

For antibody-based kits, the kit can comprise, for example: (1) a first antibody (e.g., attached to a solid support) which binds to a GLP-2 polypeptide; and, optionally, (2) a second, different antibody which binds to either the polypeptide or the first antibody and is conjugated to a detectable agent.

For oligonucleotide-based kits, the kit can comprise, for example: (1) an oligonucleotide, e.g., a detectably labeled oligonucleotide, which hybridizes to a nucleic acid sequence encoding a polypeptide of the invention or (2) a pair of primers useful for amplifying a nucleic acid molecule encoding a polypeptide of the invention. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the polypeptide.

The invention provides a kit containing an antibody of the invention conjugated to a detectable substance, and instructions for use.

The pharmaceutical compositions of the invention can be included in a container, pack, or dispenser together with instructions for administration.

5.8 Diagnostic and Monitoring Assays

The methods described herein can furthermore be utilized as diagnostic assay or an assay to monitor disorder progression or treatment effectiveness. For example, the assays described herein can be utilized to identify a subject having or at risk of developing a disorder associated with aberrant expression or activity of a GLP-2 molecule. Alternatively, the assays can be utilized to identify a subject having or at risk for developing such a disease or disorder. Thus, the present invention provides a method in which a test tissue sample is obtained from a subject and a GLP-2 molecule is detected, wherein the presence of the GLP-2 molecule is diagnostic for a subject having or at risk of developing a disease or disorder associated with aberrant expression or activity of the GLP-2 molecule. As used herein, a "test tissue sample" refers to a biological sample obtained from a subject of interest. For example, a test sample can be a biological fluid (e.g., serum), cell sample, or tissue (e.g., bone or adipose).

Furthermore, the assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant expression or activity of a GLP-2 molecule. For example, such methods can be used to determine whether a subject can be effectively treated with a specific agent or class of agents (e.g., agents of a type which increase activity of the GLP-2 molecule). Thus, the present invention provides methods for determining whether a subject can be effectively treated with an agent for a disorder associated with aberrant expression or activity of a GLP-2 molecule in which a test tissue sample is obtained and the GLP-2 molecule is detected (e.g., wherein the presence of the polypeptide or nucleic acid is diagnostic for a subject that can be administered the agent to treat a disorder associated with aberrant expression or activity of the GLP-2 molecule).

The methods of the invention can also be used to detect genetic lesions or mutations in a gene encoding a GLP-2 molecule, thereby determining if a subject with the lesioned gene is at risk for a disorder characterized aberrant expression or activity of a GLP-2 molecule. In preferred embodiments, the methods include detecting, in a sample of cells from the subject, the presence or absence of a genetic lesion or mutation characterized by at least one of an alteration affecting the integrity of a gene encoding the GLP-2 molecule, or the mis-expression of the gene encoding the GLP-2 molecule. For example, such genetic lesions or mutations can be detected by ascertaining the existence of at least one of: 1) a deletion of one or more nucleotides from the gene; 2) an addition of one or more nucleotides to the gene; 3) a substitution of one or more nucleotides of the gene; 4) a chromosomal rearrangement of the gene; 5) an alteration in the level of a messenger RNA transcript of the gene; 6) an aberrant modification of the gene, such as of the methylation pattern of the genomic DNA; 7) the presence of a non-wild type splicing pattern of a messenger RNA transcript of the gene; 8) a non-wild type level of a the protein encoded by the gene; 9) an allelic loss of the gene; and 10) an inappropriate post-translational modification of the protein encoded by the gene. As described herein, there are a large number of assay techniques known in the art which can be used for detecting lesions in a gene.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al., 1988, Science 241:1077-1080; and Nakazawa et al., 1994, Proc. Natl. Acad. Sci. USA 91:360-364), the latter of which can be particularly useful for detecting point mutations in a gene (see, e.g., Abravaya et al., 1995, Nucleic Acids Res. 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to the selected gene under conditions such that hybridization and amplification of the gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al., 1990, Proc. Natl. Acad. Sci. USA 87:1874-1878), transcriptional amplification system (Kwoh, et al.,1989, Proc. Natl. Acad. Sci. USA 86:1173-1177), Q-Beta Replicase (Lizardi et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a selected gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

The effectiveness of the methods of treatment of the invention on a patient can be evaluated by, for example, determining the level of one or more markers of bone resorption as indicative of GLP-2 activity. Thus, changes in the level of the markers of bone resorption after GLP-2 molecule or activator administration can monitor treatment effectiveness. In one embodiment, the marker of bone resorption is a C-terminal telopeptide of type I collagen (S-CTX) and/or degradation products thereof (Rosenquist et al., 1998, Clin. Chem. 44:2281-2289; Christgau et al., 1998, Clin. Chem. 44:2290-2300). The level of a marker of bone resorption can be determined using methods known in the art (e.g., ELISA; Serum CrossLaps™). In a particular embodiment, a decrease in the level of circulating S-CTX indicates that the GLP-2 treatment of a patient is effective. In accordance with the methods of the invention, measurement of a marker of bone resorption can be used to determine the optimal dosage of a therapeutic agent for treating a bone-related disorder.

The present invention may be better understood by reference to the following non-limiting Examples, which are provided only as exemplary of the invention. The following examples are presented to more fullly illustrate the preferred embodiments of the invention. They should in no way be construed, however, as limiting the broader scope of the invention.

1. EXAMPLES

In these Examples, hematology and serum chemistry including glucose were measured using an auto analyzer (Vitros). Serum FSI-I was measured by IRMA (Coat-A-Count®, DPC, Los Angeles, Calif.). Serum C-telopeptide fragments of collagen type I degradation (S-CTX) were measured by ELISA, Serum CrossLaps™ assay (Osteometer BioTech A/S—Denmark). Serum osteocalcin was determined by ELISA, an assay which determines the N-terminal mid segment of the molecule. Serum insulin and c-peptide were both assessed by RIA (Coat-A-Count® for insulin and Double Antibody C-peptide for c-peptide both DPC, Los Angeles, Calif.). Total GIP was measured using the C-terminally directed antiserum R65, which reacts with the intact GIP (1-42) and the N-terminally truncated metabolite, GIP (3-42) (Krarup T, Holst J J 1984 The heterogeneity of gastric inhibitory polypeptide in porcine and human gastrointestinal mucosa evaluated with five different antisera. Regul Pept 9:35-46. ). GLP-2 was measured with a N-terminal specific antiserum code no. 92160, measuring only GLP-2 with an intact N-terminus. GLP-1 in plasma samples was measured using a RIA assay specific for the C-terminus of the GLP-1 molecule, using standards of synthetic GLP-1 (7-36) amide and antiserum no. 89390 (Orskov C, Rabenhoj L, Wettergren A, Kofod H, Holst JJ 1994 Tissue and plasma concentrations of amidated and glycine-extended glucagon-like peptide I in humans. Diabetes 43:535-539. ).

Since GLP-1 and GLP-2 are secreted in parallel and increase in a similar way in plasma after a meal ingestion, GLP-1 concentrations can be assumed to increase similarly to GLP-2 and "vice versa" (Hartmann B, Johnsen A H, Orskov C, Adelhorst K, Thim L, Holst J J 2000 Structure, measurement, and secretion of human glucagon-like peptide-2. Peptides 21:73-80. ). GLP-1 is measured in Example 1 as a marker for the effect of the tested materials on GLP-2 levels.

5.3 Example 1

Effect of Oral Fructose on GLP-2 (measured as GLP-1), GIP, and Rate of Bone Resorption Twelve healthy women (ages 30-45) and men (ages 30-60) were included in a randomized, controlled cross-over study comparing the effects of oral fructose on GLP-2, on GIP and on bone turnover. Bone turnover was assayed by measuring the amount of S-CTX in a subject's serum. Briefly, an immunoassay was performed using monoclonal antibodies specific to S-CTX fragments generated exclusively from collagen type I degradation during resorption of mature bone tissue (Rosenquist et al., 1998, Clin. Chem. 44:2281-2289). The individuals had no medical history of diseases related to bone turnover such as cancer, rheumatoid arthritis or diseases compromising absorption from the gut or excretion/re-absorption from the kidney, or any other serious disease that might influence the conduct of the study. A general laboratory screening including hematology and serum chemistry gave no indication of specific organ dysfunction. The individuals had not taken any medication that would affect bone metabolism, such as, calcium, vitamin D, estrogen or progestin in any administration form for more than 3 months prior to the beginning of the study. Subjects had never been treated with bisphosphonates or fluoride.

Sampling

Subjects fasted from 10 p.m. the evening prior to the experiment and initial blood samples were collected between 7:30 a.m. and 8:30 a.m. Immediately thereafter, oral fructose was initiated. Blood samples were collected at precisely 1, 2, 3, 6 and 9 hours after the first blood sample was drawn. A washout period of 2 weeks was instituted between each experiment.

Interventions

Oral fructose consisted of 75 g fructose dissolved in 300 ml water with the juice of a half lemon added. Oral fructose induced a reduction of 36% in S-CTX after 2 hours (FIG. 1A) whereas the level of GLP-2 (measured as GLP-1) was doubled to 220% after 2 hours, compared to the baseline of 100% at $T_0$. Accordingly, the occurrence of the other fragments of proglucagon also doubled. The level of GIP was almost maintained at baseline. Following oral fructose administration, the concentration of GLP-2 rises, as S-CTX, a marker of bone resorption, decreases. GLP-2 can be useful for decreasing bone resorption and for treating or preventing osteoporosis.

5.4 Example 2

Effect of Oral Long Chained Fatty Acids on GLP-2, GIP, and Bone Resorption Rate

Twelve healthy women (ages 30-45) and men (ages 30-60) with the same in- and exclusion-criteria as in Example 1 were included in a randomized, controlled cross-over study comparing the effects of oral long-chained fatty acids (LCFA) on GLP-2, on GIP and on bone turnover. Bone turnover was assayed by measuring the amount of S-CTX in a subject's serum. Briefly, an imunoassay was performed using monoclonal antibodies specific to S-CTX fragments generated exclusively from collagen type I degradation during resorption of mature bone tissue (Rosenquist et al., 1998, Clin. Chem. 44:2281-2289).

Sampling

Subjects fasted from 10 p.m. the evening prior to the experiment and initial blood samples were collected between 7:30 a.m. and 8:30 a.m. Immediately thereafter oral LCFA were administered. Blood samples were collected at precisely 1, 2, 3, 6 and 9 hours after the first blood sample was drawn. A washout period of 2 weeks was instituted between each experiment.

Interventions

Figure 1B:
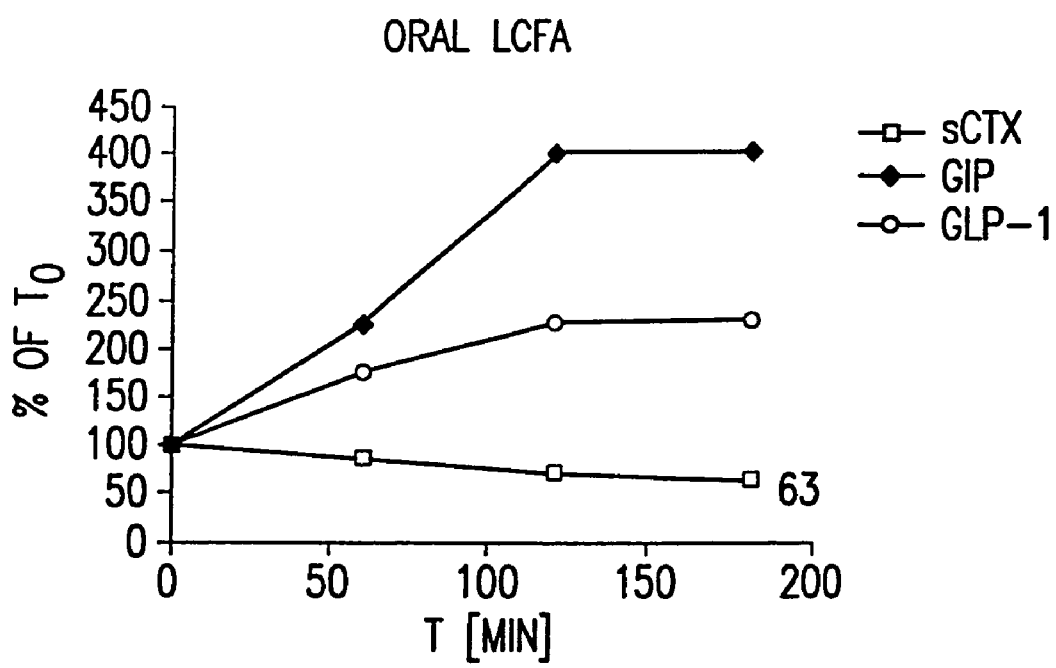

Oral LCFA consisted of 70 ml emulsion of long chained fatty acids (Calogen). Oral LCFA induced a reduction of 37% in S-CTX after 3 hours (FIG. 1B) and the occurrence of GLP-1 was doubled to the level of 230% after 3 hours compared to the baseline of 100% at $T_0$. These results are very similar to the equivalent data of Example 1. However, the occurrence of GIP was increased significantly to the level of 400%. Comparison with the level of GIP in Example 1, indicates that GIP has little or no influence on bone resorption. Following oral LCFA administration, the concentration of GLP-2 rises as S-CTX, a marker for bone resorption decreases. GLP-2 can be useful for decreasing bone resorption and for treating or preventing osteoporosis.

5.5 Example 3

Effect of Oral Protein on GLP-2, GIP, and Bone Resorption Rate

Twelve healthy women (ages 30-45) and men (ages 30-60) with the same in- and exclusion-criteria as in Example 1 were included in a randomized, controlled cross-over study comparing the effects of oral protein on GLP-2, on GIP, and on bone turnover. Bone turnover was assayed by measuring the amount of S-CTX in a subject's serum. Briefly, an imunoassay was performed using monoclonal antibodies specific to S-CTX fragments generated exclusively from collagen type I degradation during resorption of mature bone tissue (Rosenquist et al., 1998, Clin. Chem. 44:2281-2289).

Sampling

Subjects fasted from 10 p.m. the evening prior to the experiment and initial blood samples were collected between 7:30 a.m. and 8:30 a.m. Immediately thereafter, protein was administered. Blood samples were collected at precisely 1, 2, 3, 6 and 9 hours after the first blood sample was drawn. A washout period of 2 weeks was instituted between each experiment.

Interventions

Figure 1C:
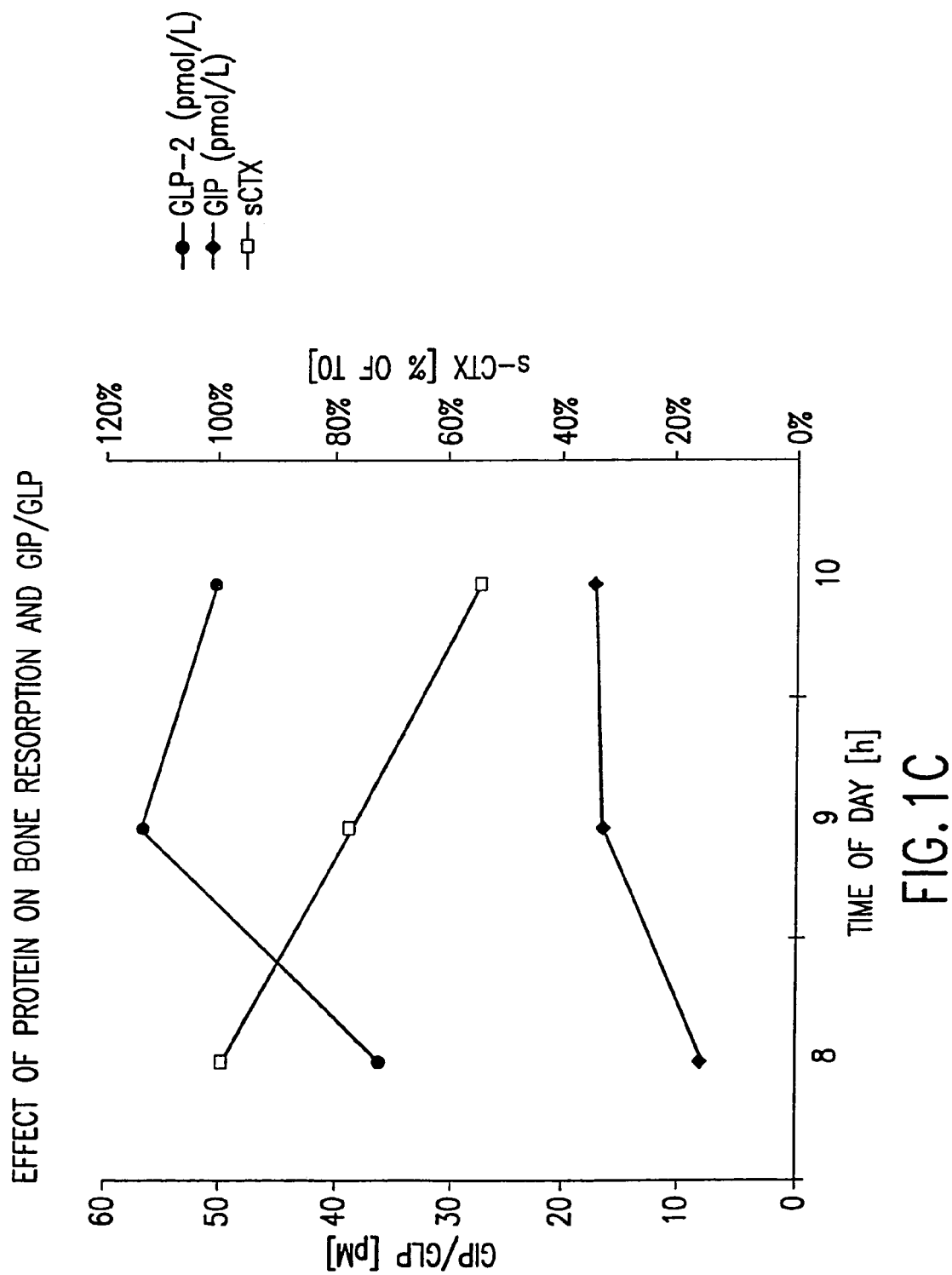

Oral protein consisted of 40 g protein powder (Casilan) dissolved in 600 ml water. Oral protein induced a reduction of 45% in S-CTX after 2 hours (FIG. 1C) whereas the occurrence of GLP-2 and GIP were both increased. The level of GIP increased from 8 pM to 17 pM and the level of GLP-2 increased from 36 pM to 57 pM after 1 hour decreasing slightly after 2 hours to the level of 51 pM. These results indicate that increasing concentration of GLP-2 can reduce bone resorption as measured by S-CTX.

5.6 Example 4

Effect of a Normal Mixed Meal on GLP-1, GLP-2, and Bone Resorption Rate

Seven short-bowel patients (<140 cm remnant small bowel) were recruited. Four females and three males were studied comparing the effects of a normal mixed meal on GLP-1, on GLP-2 and on bone turnover. Bone turnover was assayed by measuring the amount of S-CTX in a subject's serum. Briefly, an imunoassay was performed using monoclonal antibodies specific to S-CTX fragments generated exclusively from collagen type I degradation during resorption of mature bone tissue (Rosenquist et al., 1998, Clin. Chem. 44:2281-2289). The methodology of the measurement of GLP-1 and GLP-2 and the description of the test subjects were as described in detail in Jeppesen et al. (2000, "Elevated plasma glucagon-like peptide 1 and 2 concentrations in ileum resected short bowel patients with a preserved colon", Gut 47: 370-376).

Sampling

Subjects fasted overnight and initial peripheral venous blood was collected 15 minutes prior to the test meal. The test meal was completed in 15 minutes. Venous blood was collected at 10, 20, 30, 45, 60, 120 and 180 minutes after the start of the test meal.

Interventions

The normal mixed meal consisted of rye bread, toast, butter, cheese, jam, yogurt, banana, and orange juice (total weight 755 g), with an energy content of 3.92 MJ and a protein:carbohydrate:fat energy ratio of 10%:52%:37% evaluated from food tables.

Figure 2:
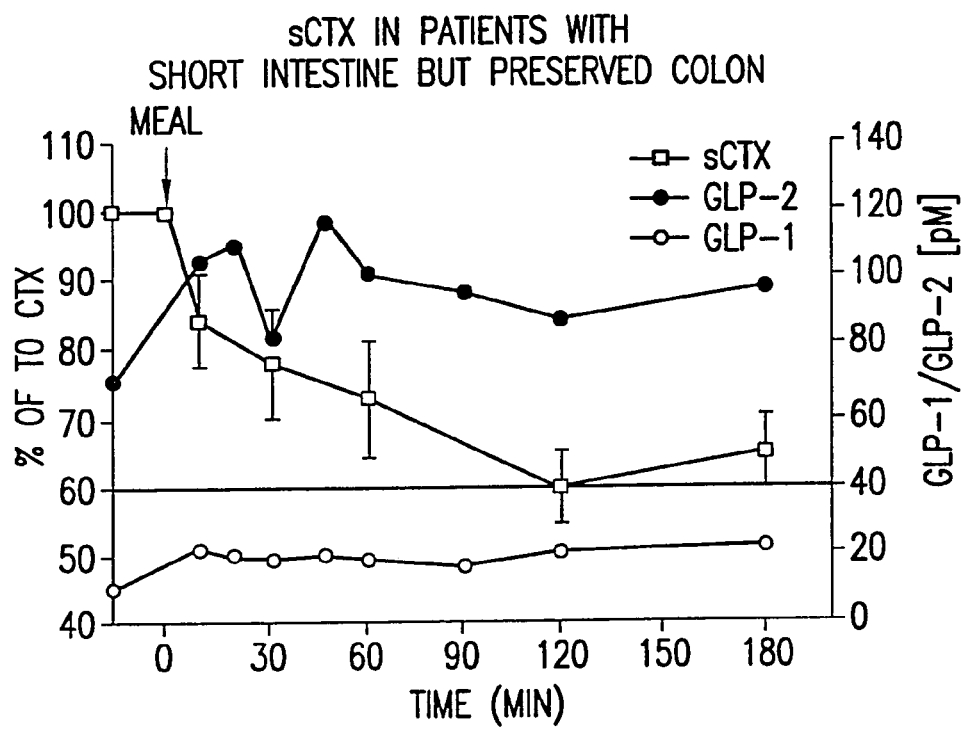
FIG. 2 shows the levels of GLP-1, GLP-2, and S-CTX over a 3 hour period following a normal meal. Subjects had a short intestine with a preserved colon.

A normal mixed meal induced a reduction of 40% in S-CTX after 2 hours (FIG. 2) whereas GLP-1 and GLP-2 levels were both increased. The level of GLP-1 was increased from 70 pM to 98 pM after 3 hours and the level of GLP-2 was increased from 10 pM to 22 pM after 3 hours. These results indicate that increasing levels of GLP-1 and/or GLP-2 can reduce bone resorption as measured by S-CTX.

5.7 Example 5

Effect of a GLP-2 injection on GLP-2 and bone resorption rate

Six healthy women and 3 healthy men between-the ages of 24-53 were included in a study comparing the effect of a GLP-2 injection on GLP-2 expression levels and on bone turnover. Bone turnover was assayed by measuring the amount of S-CTX in a subject's serum. Briefly, an imunoassay was performed using monoclonal antibodies specific to S-CTX fragments generated exclusively from collagen type I degradation during resorption of mature bone tissue (Rosenquist et al., 1998, Clin. Chem. 44:2281-2289). The description of the methodology of measurement of full length GLP-2 and total GLP-2 (including degradation products by, e.g., DPP IV protease) and the description of the test persons was as described in detail in Hartmann et al. (2000, "In vivo and in vitro degradation of glucagon-like peptide-2 in humans", J. Clin. Endocrinol. Metab. 85:2884-2888).

Sampling

Blood samples were drawn at regular intervals before, during, and after the injection.

Interventions

Figure 3:
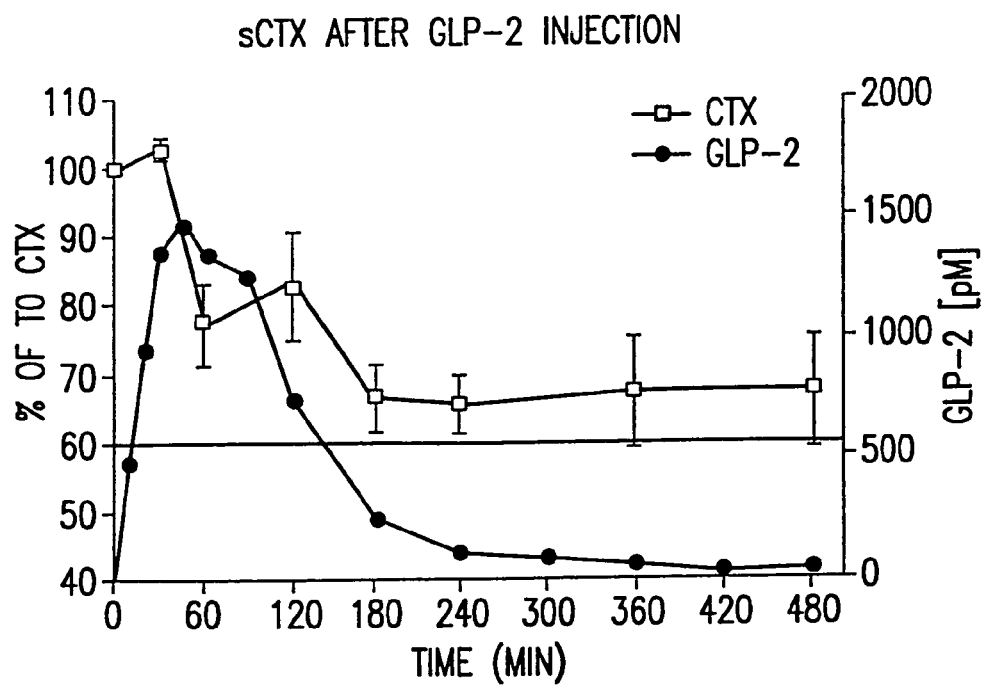
FIG. 3 shows the levels of S-CTX and GLP-2 over a 7 hour period following a subcutaneous bolus injection of 400 μg of synthetic human GLP-2.

The test subjects received a subcutaneous bolus injection of 400 μg synthetic human GLP-2. The GLP-2 injection induced a reduction of 35% in S-CTX after 3 hours, whereas the level of GLP-2 increased naturally after the injection to a peak after 1 hour indicating that an increase in GLP-2 results in the reduction of bone resorption as measured by the S-CTX immunoassay (FIG. 3).

6.6 Example 6

Effect of GLP-2A on Bone Density and Bone Strength in a 6 Week Study in Aged Ovariectomized Rats The following is a protocol suitable to test whether GLP-2A at 250 μg/kg s.c. twice daily can inhibit ovariectomized induced bone loss in aged rats.

Test Articles and Vehicle

Test articles: GLP-2 analogue (Gly2)GLP-2: His-Gly-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp-OH.

Vehicle: 0.5% gelatin/PBS (degassed) Gelatin A: Cat. No. 325910, batch no. 273622 (Unikem, Copenhagen, Denmark). PBS: Dubecco's Phosphate buffered saline (Bio-Whitaker cat.no.BE17-512F)

Positive control: 17β-estradiol pellet 0.5 mg/60 days release implanted subcutaneous (SE-121 Innovative Research of America)

A dose of 250 μg/kg is administered by subcutaneous injections twice daily (10-12 hours apart). The injection site will vary according to the injection scheme. The dose is calculated as follow: the weight ofthe rat in kg=the dose in ml; e.g. 0.301kg=0.30 ml Experimental System:

The study is performed in 50 female Sprague Dawley rats in 4 groups each of 12 or 13 rats.

Surgery:

The rats are anaesthetized with Hypnorm-Domicum (1 part Hypnorm+1 part Dormicum+2 part sterile dI water. The rats are given 0.15 ml/100 g body weight). Ovariectomy (OVX) or sham operations are performed via a midline incision in the back of the rats. After the OVX or sham operations, 17-β estradiol pellets will be inserted subcutaneous in the relevant animals (estrogen group).

Fluorescent Labeling of Bones:

Bones are labeled by subcutaneous injections of calcein (15 mg/kg body weight) 10 and 3 days prior to sacrifice. Calcein (Sigma C-0875 lot 26H0968) is dissolved in 2% natriumhydrogencarbonat pH 7.4 at 15 mg/ml.

Study design:

Following terminal blood sampling the animals will be killed by cervical dislocation in $O_2/CO_2$ anesthesia and necropsy will be performed. The wet weight and length of the small intestine and the colon will be recorded.

Bones:

Dissect out both tibiae and femurs along with the vertebrae (L3-L6). Clean them of any adhering tissues.

Store the vertebrae (L5 and L6) and right femur at +4° C., wrapped in 0.9% saline (containing 0.1% sodium azide) soaked gauze (for strength test).

Store the left tibia and the femur in 70% ethanol at +4° C. (pQCT analysis and possibly histology).

Snap freeze the right tibia in liquid nitrogen before storing at −80° C. (RNA). Place the vertebrae (L3-L4) in 70% ethanol at +4° C. (histomorphometry)

Tests

Urine and blood samples are used to measure collagen type I (bone) resorption peptides (RatLaps—Nordic Bioscience), osteocalcin (RatMid—Nordic Bioscience), and calcium. Bones are assessed by PQCT, trabecular strength and histomorphologic analysis.

Results

It will be observed that the group treated with GLP-2 analogue and the positive control group are protected against bone density loss following the OVX procedure in comparison to the untreated controls.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

What is claimed is:

1. A therapeutic composition comprising
   a) a first active component which promotes bone formation and promotes bone resorption; and
   b) a second active component which is a GLP-2, or an analogue or derivative or mimic of GLP-2 having the ability to bind and activate a GLP-2 receptor, or is a GLP-2 receptor agonist.

2. A composition as claimed in claim 1, comprising as component (a) a PTH receptor binding ligand.

3. A composition as claimed in claim 2, wherein the PTH receptor binding ligand is a PTH, an active fragment of PTH, PTHrP, an active fragment of PTHrP, or is an analogue or derivative of any one of said ligands having the ability to bind and activate a PTH receptor.

4. A composition as claimed in claim 2, wherein component (a) is a PTH-1 receptor binding ligand.

5. A composition as claimed in claim 2, wherein said component (a) is also a PTH -2 receptor activating ligand.

6. A composition as claimed in claim 2, wherein said component (a) is not an activator for the PTH-2 receptor.

7. A composition as claimed in claim 2, wherein component (a) is a full length PTH or is a C-terminal truncated PTH, optionally modified from a natural sequence by substitution of one or more amino acids.

8. A composition as claimed in claim 7, wherein component (a) is a full length PTH or an N-terminal fragment containing at least the first 31 amino acid residues of PTH, optionally modified from a natural sequence by substitution of one or more amino acids.

9. A composition as claimed in claim 8, wherein component (a) is [Leu(27)]-cyclo(Glu(22)-Lys(26))-hPTH-(1-31)NH(2).

10. A composition as claimed in claim 7, wherein said component (a) is hPTH (1-84), hPTH (1-37), hPTH (1-36), hPTH (1-34), hPTH (1-31), or a cyclic derivative of any of the foregoing.

11. A composition as claimed in claim 2, wherein said component (a) is a PTH (1-9) fragment, optionally containing substitutions of natural or unnatural amino acids whilst maintaining PTH1 receptor signal activation activity and conjugated to an effective PTH1 receptor binding moiety.

12. A composition as claimed in claim 2, wherein said component (a) is full length PTHrP or is a C-terminal truncated PTHrP, optionally modified from a natural sequence by substitution of one or more amino acids.

13. A composition as claimed in claim 12, wherein said component (a) is a PTHrP (1-40), optionally modified from a natural sequence by substitution of one or more amino acids.

14. A composition as claimed in claim 1, wherein said component (b) is GLP-2 (1-34).

15. A composition as claimed in claim 8, wherein said component (b) is GLP-2 (1-34).

16. A composition as claimed in claim 1, wherein said composition is formulated for administration by injection.

* * * * *

SEQUENCE LISTING

```
<160> NUMBER OF SEQ ID NOS: 279

<210> SEQ ID NO 1
<211> LENGTH: 35
<212> TYPE: PRT
<213> ORGANISM: Homo sapiens

<400> SEQUENCE: 1

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Arg Lys
        35

<210> SEQ ID NO 2
<211> LENGTH: 35
<212> TYPE: PRT
<213> ORGANISM: Octodon degus

<400> SEQUENCE: 2

His Ala Asp Gly Ser Phe Ser Asp Glu Met Asn Thr Val Leu Asp His
1               5                   10                  15

Leu Ala Thr Lys Asp Phe Ile Asn Trp Leu Ile Gln Thr Lys Ile Thr
            20                  25                  30

Asp Arg Lys
        35

<210> SEQ ID NO 3
<211> LENGTH: 35
<212> TYPE: PRT
```

<213> ORGANISM: Cavia sp.

<400> SEQUENCE: 3

His Ala Asp Gly Ser Phe Ser Asp Glu Met Asn Thr Ile Leu Asp Asn
1               5                   10                  15

Leu Ala Thr Arg Asp Phe Ile Asn Trp Leu Ile Gln Thr Lys Ile Thr
            20                  25                  30

Asp Arg Lys
        35

<210> SEQ ID NO 4
<211> LENGTH: 35
<212> TYPE: PRT
<213> ORGANISM: Cricetulus sp.

<400> SEQUENCE: 4

His Ala Asp Gly Ser Phe Ser Asp Glu Met Asn Thr Ile Leu Asp Ser
1               5                   10                  15

Leu Ala Thr Arg Asp Phe Ile Asn Trp Leu Ile Gln Thr Lys Ile Thr
            20                  25                  30

Asp Lys Lys
        35

<210> SEQ ID NO 5
<211> LENGTH: 35
<212> TYPE: PRT
<213> ORGANISM: Rattus sp.

<400> SEQUENCE: 5

His Ala Asp Gly Ser Phe Ser Asp Glu Met Asn Thr Ile Leu Asp Asn
1               5                   10                  15

Leu Ala Thr Arg Asp Phe Ile Asn Trp Leu Ile Gln Thr Lys Ile Thr
            20                  25                  30

Asp Lys Lys
        35

<210> SEQ ID NO 6
<211> LENGTH: 35
<212> TYPE: PRT
<213> ORGANISM: Bos sp.

<400> SEQUENCE: 6

His Ala Asp Gly Ser Phe Ser Asp Glu Met Asn Thr Val Leu Asp Ser
1               5                   10                  15

Leu Ala Thr Arg Asp Phe Ile Asn Trp Leu Leu Gln Thr Lys Ile Thr
            20                  25                  30

Asp Arg Lys
        35

<210> SEQ ID NO 7
<211> LENGTH: 37
<212> TYPE: PRT
<213> ORGANISM: Artificial Sequence
<220> FEATURE:
<223> OTHER INFORMATION: Description of Artificial Sequence: Synthetic
      GLP-2 formula sequence
<220> FEATURE:
<221> NAME/KEY: MOD_RES
<222> LOCATION: (1)..(2)
<223> OTHER INFORMATION: This region may encompass Arg, Arg-Arg, or
      is not present
<220> FEATURE:
<221> NAME/KEY: MOD_RES -continued

```
<222> LOCATION: (15)..(15)
<223> OTHER INFORMATION: Neutral, polar, large and nonaromatic amino
      acid residue
<220> FEATURE:
<221> NAME/KEY: MOD_RES
<222> LOCATION: (18)..(18)
<223> OTHER INFORMATION: Neutral and polar amino acid residue
<220> FEATURE:
<221> NAME/KEY: MOD_RES
<222> LOCATION: (21)..(21)
<223> OTHER INFORMATION: Neutral amino acid residue
<220> FEATURE:
<221> NAME/KEY: MOD_RES
<222> LOCATION: (29)..(29)
<223> OTHER INFORMATION: Neutral, polar, large and nonaromatic amino
      acid residue
<220> FEATURE:
<221> NAME/KEY: MOD_RES
<222> LOCATION: (30)..(30)
<223> OTHER INFORMATION: Neutral or basic amino acid residue
<220> FEATURE:
<221> NAME/KEY: MOD_RES
<222> LOCATION: (36)..(37)
<223> OTHER INFORMATION: This region may encompass Arg, Lys, Arg-Lys,
      Lys-Lys, or is not present

<400> SEQUENCE: 7

Xaa Xaa His Ala Asp Gly Ser Phe Ser Asp Glu Met Asn Thr Xaa Leu
1               5                   10                  15

Ala Xaa Leu Ala Xaa Arg Asp Phe Ile Asn Trp Leu Xaa Xaa Thr Lys
            20                  25                  30

Ile Thr Asp Xaa Xaa
            35

<210> SEQ ID NO 8
<211> LENGTH: 33
<212> TYPE: PRT
<213> ORGANISM: Artificial Sequence
<220> FEATURE:
<223> OTHER INFORMATION: Description of Artificial Sequence: Synthetic
      GLP-2 variant sequence

<400> SEQUENCE: 8

His Ala Asp Gly Ser Phe Ser Asp Glu Met Asn Thr Ile Leu Asp Asn
1               5                   10                  15

Leu Ala Thr Arg Asp Phe Ile Asn Trp Leu Ile Gln Thr Lys Ile Thr
            20                  25                  30

Asp

<210> SEQ ID NO 9
<211> LENGTH: 37
<212> TYPE: PRT
<213> ORGANISM: Artificial Sequence
<220> FEATURE:
<223> OTHER INFORMATION: Description of Artificial Sequence: Synthetic
      GLP-2 variant sequence
<220> FEATURE:
<221> NAME/KEY: MOD_RES
<222> LOCATION: (1)..(2)
<223> OTHER INFORMATION: This region may encompass Arg, Arg-Arg, or
      is not present
<220> FEATURE:
<221> NAME/KEY: MOD_RES
<222> LOCATION: (15)..(15)
<223> OTHER INFORMATION: Neutral, polar, large and nonaromatic amino
      acid residue
<220> FEATURE:
<221> NAME/KEY: MOD_RES
<222> LOCATION: (18)..(18)
<223> OTHER INFORMATION: Neutral and polar amino acid residue
<220> FEATURE:
```

```
<221> NAME/KEY: MOD_RES
<222> LOCATION: (21)..(21)
<223> OTHER INFORMATION: Neutral amino acid residue
<220> FEATURE:
<221> NAME/KEY: MOD_RES
<222> LOCATION: (29)..(29)
<223> OTHER INFORMATION: Neutral, polar, large and nonaromatic amino
      acid residue
<220> FEATURE:
<221> NAME/KEY: MOD_RES
<222> LOCATION: (30)..(30)
<223> OTHER INFORMATION: Neutral or basic amino acid residue
<220> FEATURE:
<221> NAME/KEY: MOD_RES
<222> LOCATION: (36)..(37)
<223> OTHER INFORMATION: This region may encompass Arg, Lys, Arg-Lys,
      Lys-Lys, or is not present

<400> SEQUENCE: 9

Xaa Xaa His Ala Asp Gly Ser Phe Ser Asp Glu Met Asn Thr Xaa Leu
 1               5                  10                  15

Asp Xaa Leu Ala Xaa Arg Asp Phe Ile Asn Trp Leu Xaa Xaa Thr Lys
            20                  25                  30

Ile Thr Asp Xaa Xaa
            35

<210> SEQ ID NO 10
<211> LENGTH: 37
<212> TYPE: PRT
<213> ORGANISM: Artificial Sequence
<220> FEATURE:
<223> OTHER INFORMATION: Description of Artificial Sequence: Synthetic
      GLP-2 variant sequence
<220> FEATURE:
<221> NAME/KEY: MOD_RES
<222> LOCATION: (1)..(2)
<223> OTHER INFORMATION: This region may encompass Arg, Arg-Arg, or
      is not present
<220> FEATURE:
<221> NAME/KEY: MOD_RES
<222> LOCATION: (15)..(15)
<223> OTHER INFORMATION: Ile or Val
<220> FEATURE:
<221> NAME/KEY: MOD_RES
<222> LOCATION: (18)..(18)
<223> OTHER INFORMATION: Asn or Ser
<220> FEATURE:
<221> NAME/KEY: MOD_RES
<222> LOCATION: (21)..(21)
<223> OTHER INFORMATION: Ala or Thr
<220> FEATURE:
<221> NAME/KEY: MOD_RES
<222> LOCATION: (29)..(29)
<223> OTHER INFORMATION: Ile or Leu
<220> FEATURE:
<221> NAME/KEY: MOD_RES
<222> LOCATION: (30)..(30)
<223> OTHER INFORMATION: Gln or His
<220> FEATURE:
<221> NAME/KEY: MOD_RES
<222> LOCATION: (36)..(37)
<223> OTHER INFORMATION: This region may encompass Arg, Lys, Arg-Lys,
      Lys-Lys, or is not present

<400> SEQUENCE: 10

Xaa Xaa His Ala Asp Gly Ser Phe Ser Asp Glu Met Asn Thr Xaa Leu
 1               5                  10                  15

Asp Xaa Leu Ala Xaa Arg Asp Phe Ile Asn Trp Leu Xaa Xaa Thr Lys
            20                  25                  30

Ile Thr Asp Xaa Xaa
            35
```

```
<210> SEQ ID NO 11
<211> LENGTH: 37
<212> TYPE: PRT
<213> ORGANISM: Artificial Sequence
<220> FEATURE:
<223> OTHER INFORMATION: Description of Artificial Sequence: Synthetic
      GLP-2 variant sequence
<220> FEATURE:
<221> NAME/KEY: MOD_RES
<222> LOCATION: (1)..(2)
<223> OTHER INFORMATION: This region may encompass one or two basic
      amino acids selected from the group Arg, Lys, and His, or is not
      present
<220> FEATURE:
<221> NAME/KEY: MOD_RES
<222> LOCATION: (3)..(3)
<223> OTHER INFORMATION: His or Tyr
<220> FEATURE:
<221> NAME/KEY: MOD_RES
<222> LOCATION: (4)..(4)
<223> OTHER INFORMATION: Ala or an Ala-replacement amino acid conferring
      on said analog resistance to DPP-IV enzyme
<220> FEATURE:
<221> NAME/KEY: MOD_RES
<222> LOCATION: (5)..(5)
<223> OTHER INFORMATION: Pro, HPro, Asp, or Glu
<220> FEATURE:
<221> NAME/KEY: MOD_RES
<222> LOCATION: (6)..(6)
<223> OTHER INFORMATION: Gly or Ala
<220> FEATURE:
<221> NAME/KEY: MOD_RES
<222> LOCATION: (11)..(15)
<223> OTHER INFORMATION: Glu-Xaa-Asn-Thr-Ile (SEQ ID NO: 267) or
      Tyr-Ser-Lys-Tyr (SEQ ID NO: 268); thus Xaa at position 15 may or
      may not be present depending upon the substitution
<220> FEATURE:
<221> NAME/KEY: MOD_RES
<222> LOCATION: (12)
<223> OTHER INFORMATION: Met or an oxidatively stable Met-replacement
      amino acid, with the proviso that positions (11)..(15) is
      encompassed by SEQ ID NO: 267; see previous feature for
      alternative substitution
<220> FEATURE:
<221> NAME/KEY: MOD_RES
<222> LOCATION: (21)..(21)
<223> OTHER INFORMATION: Ala or Thr
<220> FEATURE:
<221> NAME/KEY: MOD_RES
<222> LOCATION: (22)..(22)
<223> OTHER INFORMATION: Arg, Lys, His, or Ala
<220> FEATURE:
<221> NAME/KEY: MOD_RES
<222> LOCATION: (25)..(25)
<223> OTHER INFORMATION: Ile or Val
<220> FEATURE:
<221> NAME/KEY: MOD_RES
<222> LOCATION: (26)..(26)
<223> OTHER INFORMATION: Asn, Ala or Gln with the proviso that if
      residue 25 is Ile then residue 26 is Asn or Ala and that if
      residue 25 is Val, then residue 26 is Gln
<220> FEATURE:
<221> NAME/KEY: MOD_RES
<222> LOCATION: (33)..(35)
<223> OTHER INFORMATION: may or not be present with the proviso that if
      residue 34 is not present then residue 35 is also not present
<220> FEATURE:
<221> NAME/KEY: MOD_RES
<222> LOCATION: (36)..(37)
<223> OTHER INFORMATION: This region may encompass one or two basic
      amino acids selected from the group Arg, Lys, and His, or is not
      present

<400> SEQUENCE: 11

Xaa Xaa Xaa Xaa Xaa Xaa Ser Phe Ser Asp Xaa Xaa Xaa Xaa Xaa Leu
1               5                   10                  15
```

```
Asp Asn Leu Ala Xaa Xaa Asp Phe Xaa Xaa Trp Leu Ile Gln Thr Lys
            20                  25                  30

Ile Thr Asn Xaa Xaa
        35
```

<210> SEQ ID NO 12
<211> LENGTH: 37
<212> TYPE: PRT
<213> ORGANISM: Artificial Sequence
<220> FEATURE:
<223> OTHER INFORMATION: Description of Artificial Sequence: Synthetic
      GLP-2 variant sequence
<220> FEATURE:
<221> NAME/KEY: MOD_RES
<222> LOCATION: (1)..(2)
<223> OTHER INFORMATION: This region may encompass one or two basic
      amino acids Selected from the group Arg, Lys, and His
<220> FEATURE:
<221> NAME/KEY: MOD_RES
<222> LOCATION: (21)..(21)
<223> OTHER INFORMATION: Ala, Thr, or a neutral amino acid residue
<220> FEATURE:
<221> NAME/KEY: MOD_RES
<222> LOCATION: (36)..(37)
<223> OTHER INFORMATION: This region may encompass one or two basic
      amino acids selected from the group Arg, Lys, and His, or is not
      present
<220> FEATURE:
<223> OTHER INFORMATION: see specification as filed for detailed
      description of substitutions and preferred embodiments

<400> SEQUENCE: 12

```
Xaa Xaa His Ala Asp Gly Ser Phe Ser Asp Glu Met Asn Thr Ile Leu
1               5                   10                  15

Asp Asn Leu Ala Xaa Arg Asp Phe Ile Asn Trp Leu Ile Gln Thr Lys
            20                  25                  30

Ile Thr Asp Xaa Xaa
        35
```

<210> SEQ ID NO 13
<211> LENGTH: 33
<212> TYPE: PRT
<213> ORGANISM: Artificial Sequence
<220> FEATURE:
<223> OTHER INFORMATION: Description of Artificial Sequence: Synthetic
      GLP-2 variant sequence

<400> SEQUENCE: 13

```
His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp
```

<210> SEQ ID NO 14
<211> LENGTH: 33
<212> TYPE: PRT
<213> ORGANISM: Artificial Sequence
<220> FEATURE:
<223> OTHER INFORMATION: Description of Artificial Sequence: Synthetic
      GLP-2 variant sequence

<400> SEQUENCE: 14

```
His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30
```

Asp

<210> SEQ ID NO 15
<211> LENGTH: 84
<212> TYPE: PRT
<213> ORGANISM: Homo sapiens

<400> SEQUENCE: 15

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 16
<211> LENGTH: 177
<212> TYPE: PRT
<213> ORGANISM: Homo sapiens

<400> SEQUENCE: 16

Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
            20                  25                  30

Arg Leu Lys Arg Ala Val Ser Glu His Gln Leu Leu His Asp Lys Gly
        35                  40                  45

Lys Ser Ile Gln Asp Leu Arg Arg Phe Phe Leu His His Leu Ile
    50                  55                  60

Ala Glu Ile His Thr Ala Glu Ile Arg Ala Thr Ser Glu Val Ser Pro
65                  70                  75                  80

Asn Ser Lys Pro Ser Pro Asn Thr Lys Asn His Pro Val Arg Phe Gly
                85                  90                  95

Ser Asp Asp Glu Gly Arg Tyr Leu Thr Gln Glu Thr Asn Lys Val Glu
            100                 105                 110

Thr Tyr Lys Glu Gln Pro Leu Lys Thr Pro Gly Lys Lys Lys Lys Gly
        115                 120                 125

Lys Pro Gly Lys Arg Lys Glu Gln Glu Lys Lys Arg Arg Thr Arg
    130                 135                 140

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg Arg
                165                 170                 175

His

<210> SEQ ID NO 17
<211> LENGTH: 37
<212> TYPE: PRT
<213> ORGANISM: Artificial Sequence
<220> FEATURE:
<223> OTHER INFORMATION: Description of Artificial Sequence: Synthetic
      GLP-2 formula sequence -continued

```
<220> FEATURE:
<221> NAME/KEY: MOD_RES
<222> LOCATION: (1)..(2)
<223> OTHER INFORMATION: This region may encompass one or two basic
      amino acids selected from the group Arg, Lys, and His, or is not
      present
<220> FEATURE:
<221> NAME/KEY: MOD_RES
<222> LOCATION: (3)
<223> OTHER INFORMATION: His, Tyr, or not present
<220> FEATURE:
<221> NAME/KEY: MOD_RES
<222> LOCATION: (4)
<223> OTHER INFORMATION: Ala, Leu, Cys, Glu, Arg, Trp, Tyr, DhPro,
      D-Pro, D-Ala, Gly Val, Lys, Ile, Trp, PO3-Tyr, Cys an Ala-
      replacement amino acid; see specification as filed for preferred
      embodiments
<220> FEATURE:
<221> NAME/KEY: MOD_RES
<222> LOCATION: (5)
<223> OTHER INFORMATION: Pro, H-Pro, Asp, Glu or not present
<220> FEATURE:
<221> NAME/KEY: MOD_RES
<222> LOCATION: (6)
<223> OTHER INFORMATION: Gly, Ala or not present
<220> FEATURE:
<221> NAME/KEY: MOD_RES
<222> LOCATION: (7)
<223> OTHER INFORMATION: Any amino acid
<220> FEATURE:
<221> NAME/KEY: MOD_RES
<222> LOCATION: (9)
<223> OTHER INFORMATION: Any amino acid
<220> FEATURE:
<221> NAME/KEY: MOD_RES
<222> LOCATION: (11)
<223> OTHER INFORMATION: Glu or Tyr
<220> FEATURE:
<221> NAME/KEY: MOD_RES
<222> LOCATION: (12)
<223> OTHER INFORMATION: Met or an oxidisable stable Met analog, Val,
      Ile, Asn, Glu, Gln, Tyr, Phe, Leu, Nle, Ala, Gly or Ser; see
      specification as filed for detailed description of
      preferred embodiments
<220> FEATURE:
<221> NAME/KEY: MOD_RES
<222> LOCATION: (13)
<223> OTHER INFORMATION: Asn or Lys
<220> FEATURE:
<221> NAME/KEY: MOD_RES
<222> LOCATION: (14)
<223> OTHER INFORMATION: Thr or Tyr
<220> FEATURE:
<221> NAME/KEY: MOD_RES
<222> LOCATION: (15)
<223> OTHER INFORMATION: Ile, Val or a neutral, polar, large and
      nonaromatic amino acid
<220> FEATURE:
<221> NAME/KEY: MOD_RES
<222> LOCATION: (17)
<223> OTHER INFORMATION: Any amino acid
<220> FEATURE:
<221> NAME/KEY: MOD_RES
<222> LOCATION: (18)
<223> OTHER INFORMATION: Asn, Ser or a neutral and polar amino acid
<220> FEATURE:
<221> NAME/KEY: MOD_RES
<222> LOCATION: (21)
<223> OTHER INFORMATION: Ala, Thr or a neutral amino acid
<220> FEATURE:
<221> NAME/KEY: MOD_RES
<222> LOCATION: (22)
<223> OTHER INFORMATION: Arg, Lys, His or Ala
<220> FEATURE:
<221> NAME/KEY: MOD_RES
<222> LOCATION: (24)
<223> OTHER INFORMATION: Any amino acid
<220> FEATURE:
<221> NAME/KEY: MOD_RES
```

```
<222> LOCATION: (25)
<223> OTHER INFORMATION: Ile or Val
<220> FEATURE:
<221> NAME/KEY: MOD_RES
<222> LOCATION: (26)
<223> OTHER INFORMATION: Asn, Gln or Ala
<220> FEATURE:
<221> NAME/KEY: MOD_RES
<222> LOCATION: (29)
<223> OTHER INFORMATION: Ile, Leu or a neutral, polar, large and
      nonaromatic amino acid
<220> FEATURE:
<221> NAME/KEY: MOD_RES
<222> LOCATION: (30)
<223> OTHER INFORMATION: Gln, His or a neutral or basic amino acid
<220> FEATURE:
<221> NAME/KEY: MOD_RES
<222> LOCATION: (31)
<223> OTHER INFORMATION: Any amino acid
<220> FEATURE:
<221> NAME/KEY: MOD_RES
<222> LOCATION: (33)
<223> OTHER INFORMATION: Ile or Arg
<220> FEATURE:
<221> NAME/KEY: MOD_RES
<222> LOCATION: (34)
<223> OTHER INFORMATION: Any amino acid
<220> FEATURE:
<221> NAME/KEY: MOD_RES
<222> LOCATION: (35)
<223> OTHER INFORMATION: Any amino acid
<220> FEATURE:
<221> NAME/KEY: MOD_RES
<222> LOCATION: (36)..(37)
<223> OTHER INFORMATION: This region may encompass one or two basic
      amino acids selected from the group Arg, Lys, His or is not
      present
<220> FEATURE:
<223> OTHER INFORMATION: See specification as filed for detailed
      description of substitutions and preferred embodiments

<400> SEQUENCE: 17

Xaa Xaa Xaa Xaa Xaa Xaa Xaa Phe Xaa Asp Xaa Xaa Xaa Xaa Xaa Leu
1               5                   10                  15

Xaa Xaa Leu Ala Xaa Xaa Asp Xaa Xaa Xaa Trp Leu Xaa Xaa Xaa Lys
            20                  25                  30

Xaa Xaa Xaa Xaa Xaa
        35

<210> SEQ ID NO 18
<211> LENGTH: 34
<212> TYPE: PRT
<213> ORGANISM: Homo sapiens

<400> SEQUENCE: 18

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 19
<211> LENGTH: 37
<212> TYPE: PRT
<213> ORGANISM: Homo sapiens

<400> SEQUENCE: 19

Ser Val Ser Glu Ile Gln Leu Met His Asn Leu Gly Lys His Leu Asn
1               5                   10                  15
```

```
Ser Met Glu Arg Val Glu Trp Leu Arg Lys Lys Leu Gln Asp Val His
            20                  25                  30

Asn Phe Val Ala Leu
        35

<210> SEQ ID NO 20
<211> LENGTH: 36
<212> TYPE: PRT
<213> ORGANISM: Homo sapiens

<400> SEQUENCE: 20

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala
        35

<210> SEQ ID NO 21
<211> LENGTH: 31
<212> TYPE: PRT
<213> ORGANISM: Homo sapiens

<400> SEQUENCE: 21

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val
            20                  25                  30

<210> SEQ ID NO 22
<211> LENGTH: 9
<212> TYPE: PRT
<213> ORGANISM: Homo sapiens

<400> SEQUENCE: 22

Ser Val Ser Glu Ile Gln Leu Met His
1               5

<210> SEQ ID NO 23
<211> LENGTH: 34
<212> TYPE: PRT
<213> ORGANISM: Homo sapiens

<400> SEQUENCE: 23

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Arg

<210> SEQ ID NO 24
<211> LENGTH: 34
<212> TYPE: PRT
<213> ORGANISM: Homo sapiens

<400> SEQUENCE: 24

Ser Val Ser Glu Ile Gln Leu Leu His Asn Leu Gly Lys His Leu Asn
1               5                   10                  15

Ser Gln Glu Arg Val Glu Trp Leu Arg Lys Lys Leu Gln Asp Val His
            20                  25                  30

Thr Ala
```

<210> SEQ ID NO 25
<211> LENGTH: 34
<212> TYPE: PRT
<213> ORGANISM: Homo sapiens

<400> SEQUENCE: 25

Ser Val Ser Glu Ile Gln Leu Leu His Asn Leu Gly Lys His Leu Ala
1               5                   10                  15

Ser Gln Ala Arg Val Glu Trp Leu Arg Lys Lys Leu Gln Asp Val His
            20                  25                  30

Thr Ala

<210> SEQ ID NO 26
<211> LENGTH: 34
<212> TYPE: PRT
<213> ORGANISM: Homo sapiens

<400> SEQUENCE: 26

Ser Val Ser Glu Ile Gln Leu Leu His Asn Leu Gly Lys His Leu Ala
1               5                   10                  15

Ser Gln Glu Arg Val Glu Trp Leu Arg Lys Lys Leu Gln Asp Val His
            20                  25                  30

Thr Ala

<210> SEQ ID NO 27
<211> LENGTH: 36
<212> TYPE: PRT
<213> ORGANISM: Homo sapiens

<400> SEQUENCE: 27

Ser Val Ser Glu Ile Gln Leu Leu His Asp Lys Gly Lys His Leu Asn
1               5                   10                  15

Ser Gln Glu Arg Val Glu Trp Leu Arg Lys Lys Leu Gln Asp Val His
            20                  25                  30

Asn Phe Val Ala
        35

<210> SEQ ID NO 28
<211> LENGTH: 34
<212> TYPE: PRT
<213> ORGANISM: Homo sapiens

<400> SEQUENCE: 28

Ser Val Ser Glu Ile Gln Leu Leu His Asp Lys Gly Lys His Leu Asn
1               5                   10                  15

Ser Gln Glu Arg Val Glu Trp Leu Arg Lys Lys Leu Gln Asp Val His
            20                  25                  30

Thr Ala

<210> SEQ ID NO 29
<211> LENGTH: 36
<212> TYPE: PRT
<213> ORGANISM: Homo sapiens

<400> SEQUENCE: 29

Ser Val Ser Glu Ile Gln Leu Leu His Asp Lys Gly Lys His Leu Ala
1               5                   10                  15

Ser Gln Ala Arg Val Glu Trp Leu Arg Lys Lys Leu Gln Asp Val His
            20                  25                  30

Asn Phe Val Ala
        35

<210> SEQ ID NO 30
<211> LENGTH: 34
<212> TYPE: PRT
<213> ORGANISM: Homo sapiens

<400> SEQUENCE: 30

Ser Val Ser Glu Ile Gln Leu Leu His Asp Lys Gly Lys His Leu Ala
1               5                   10                  15

Ser Gln Glu Arg Val Glu Trp Leu Arg Lys Lys Leu Gln Asp Val His
            20                  25                  30

Thr Ala

<210> SEQ ID NO 31
<211> LENGTH: 36
<212> TYPE: PRT
<213> ORGANISM: Homo sapiens

<400> SEQUENCE: 31

Ser Val Ser Glu Ile Gln Leu Leu His Asp Lys Gly Lys His Leu Ala
1               5                   10                  15

Ser Gln Glu Arg Val Glu Trp Leu Arg Lys Lys Leu Gln Asp Val His
            20                  25                  30

Asn Phe Val Ala
        35

<210> SEQ ID NO 32
<211> LENGTH: 36
<212> TYPE: PRT
<213> ORGANISM: Homo sapiens

<400> SEQUENCE: 32

Ser Val Ser Glu Ile Gln Leu Leu His Asn Leu Gly Lys His Leu Ala
1               5                   10                  15

Ser Gln Ala Arg Val Glu Trp Leu Arg Lys Lys Leu Gln Asp Val His
            20                  25                  30

Asn Phe Val Ala
        35

<210> SEQ ID NO 33
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha

<400> SEQUENCE: 33

Ser Val Ser Glu Ile Gln Xaa Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 34
<211> LENGTH: 34
<212> TYPE: PRT
<213> ORGANISM: Homo sapiens

```
<220> FEATURE:
<221> NAME/KEY: MOD_RES
<222> LOCATION: (11)..(11)
<223> OTHER INFORMATION: Cha

<400> SEQUENCE: 34

Ser Val Ser Glu Ile Gln Leu Met His Asn Xaa Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 35
<211> LENGTH: 34
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Cha

<400> SEQUENCE: 35

Ser Val Ser Glu Ile Gln Leu Met His Asn Leu Gly Lys His Xaa Asn
1               5                   10                  15

Ser Met Glu Arg Val Glu Trp Leu Arg Lys Lys Leu Gln Asp Val His
            20                  25                  30

Asn Phe

<210> SEQ ID NO 36
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha

<400> SEQUENCE: 36

Ser Val Ser Glu Ile Gln Xaa Met His Asn Xaa Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 37
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (18)..(18)
```

<223> OTHER INFORMATION: Nle

<400> SEQUENCE: 37

Ser Val Ser Glu Ile Gln Xaa Xaa His Asn Xaa Gly Lys His Leu Asn
1               5                   10                  15

Ser Xaa Glu Arg Val Glu Trp Leu Arg Lys Lys Leu Gln Asp Val His
            20                  25                  30

Asn Tyr

<210> SEQ ID NO 38
<211> LENGTH: 34
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: Cha

<400> SEQUENCE: 38

Ser Val Ser Glu Ile Gln Leu Met His Asn Leu Gly Lys His Leu Asn
1               5                   10                  15

Ser Met Glu Arg Val Glu Xaa Leu Arg Lys Lys Leu Gln Asp Val His
            20                  25                  30

Asn Phe

<210> SEQ ID NO 39
<211> LENGTH: 34
<212> TYPE: PRT
<213> ORGANISM: Homo sapiens
<220> FEATURE:
<221> NAME/KEY: MOD_RES
<222> LOCATION: (24)..(24)
<223> OTHER INFORMATION: Cha

<400> SEQUENCE: 39

Ser Val Ser Glu Ile Gln Leu Met His Asn Leu Gly Lys His Leu Asn
1               5                   10                  15

Ser Met Glu Arg Val Glu Trp Xaa Arg Lys Lys Leu Gln Asp Val His
            20                  25                  30

Asn Phe

<210> SEQ ID NO 40
<211> LENGTH: 34
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (18)..(18)
<223> OTHER INFORMATION: Nle
<220> FEATURE:
<221> NAME/KEY: MOD_RES
<222> LOCATION: (27)..(27)
<223> OTHER INFORMATION: Cha

<400> SEQUENCE: 40

Ser Val Ser Glu Ile Gln Leu Xaa His Asn Leu Gly Lys His Leu Asn
1               5                   10                  15

Ser Xaa Glu Arg Val Glu Trp Leu Arg Lys Xaa Leu Gln Asp Val His
            20                  25                  30

Asn Phe

```
<210> SEQ ID NO 41
<211> LENGTH: 34
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: Cha

<400> SEQUENCE: 41

Ser Val Ser Glu Ile Gln Leu Met His Asn Leu Gly Lys His Leu Asn
1               5                   10                  15

Ser Met Glu Arg Val Glu Trp Leu Arg Lys Lys Xaa Gln Asp Val His
            20                  25                  30

Asn Phe

<210> SEQ ID NO 42
<211> LENGTH: 34
<212> TYPE: PRT
<213> ORGANISM: Homo sapiens
<220> FEATURE:
<221> NAME/KEY: MOD_RES
<222> LOCATION: (31)..(31)
<223> OTHER INFORMATION: Cha

<400> SEQUENCE: 42

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Xaa His
            20                  25                  30

Asn Phe

<210> SEQ ID NO 43
<211> LENGTH: 34
<212> TYPE: PRT
<213> ORGANISM: Homo sapiens
<220> FEATURE:
<221> NAME/KEY: MOD_RES
<222> LOCATION: (27)..(27)
<223> OTHER INFORMATION: Cha

<400> SEQUENCE: 43

Ser Val Ser Glu Ile Gln Leu Met His Asn Leu Gly Lys His Leu Asn
1               5                   10                  15

Ser Met Glu Arg Val Glu Trp Leu Arg Lys Xaa Leu Gln Asp Val His
            20                  25                  30

Asn Phe

<210> SEQ ID NO 44
<211> LENGTH: 34
<212> TYPE: PRT
<213> ORGANISM: Homo sapiens
<220> FEATURE:
<221> NAME/KEY: MOD_RES
<222> LOCATION: (27)..(27)
<223> OTHER INFORMATION: Cha
<220> FEATURE:
<221> NAME/KEY: MOD_RES
<222> LOCATION: (29)..(29)
<223> OTHER INFORMATION: Cha

<400> SEQUENCE: 44

Ser Val Ser Glu Ile Gln Leu Met His Asn Leu Gly Lys His Leu Asn
1               5                   10                  15
```

Ser Met Glu Arg Val Glu Trp Leu Arg Lys Xaa Leu Xaa Asp Val His
            20                  25                  30

Asn Phe

<210> SEQ ID NO 45
<211> LENGTH: 34
<212> TYPE: PRT
<213> ORGANISM: Bos sp.
<220> FEATURE:
<221> NAME/KEY: MOD_RES
<222> LOCATION: (28)..(28)
<223> OTHER INFORMATION: Cha

<400> SEQUENCE: 45

Ala Val Ser Glu Ile Gln Phe Met His Asn Leu Gly Lys His Leu Ser
1               5                   10                  15

Ser Met Glu Arg Val Glu Trp Leu Arg Lys Lys Xaa Gln Asp Val His
            20                  25                  30

Asn Phe

<210> SEQ ID NO 46
<211> LENGTH: 34
<212> TYPE: PRT
<213> ORGANISM: Rattus sp.
<220> FEATURE:
<221> NAME/KEY: MOD_RES
<222> LOCATION: (28)..(28)
<223> OTHER INFORMATION: Cha

<400> SEQUENCE: 46

Ala Val Ser Glu Ile Gln Leu Met His Asn Leu Gly Lys His Leu Ala
1               5                   10                  15

Ser Val Glu Arg Met Gln Trp Leu Arg Lys Lys Xaa Gln Asp Val His
            20                  25                  30

Asn Phe

<210> SEQ ID NO 47
<211> LENGTH: 34
<212> TYPE: PRT
<213> ORGANISM: Homo sapiens
<220> FEATURE:
<221> NAME/KEY: MOD_RES
<222> LOCATION: (24)..(24)
<223> OTHER INFORMATION: Cha
<220> FEATURE:
<221> NAME/KEY: MOD_RES
<222> LOCATION: (28)..(28)
<223> OTHER INFORMATION: Cha
<220> FEATURE:
<221> NAME/KEY: MOD_RES
<222> LOCATION: (31)..(31)
<223> OTHER INFORMATION: Cha

<400> SEQUENCE: 47

Ser Val Ser Glu Ile Gln Leu Met His Asn Leu Gly Lys His Leu Asn
1               5                   10                  15

Ser Met Glu Arg Val Glu Trp Xaa Arg Lys Lys Xaa Gln Asp Xaa His
            20                  25                  30

Asn Phe

<210> SEQ ID NO 48
<211> LENGTH: 34
<212> TYPE: PRT
<213> ORGANISM: Homo sapiens

```
<220> FEATURE:
<221> NAME/KEY: MOD_RES
<222> LOCATION: (16)..(16)
<223> OTHER INFORMATION: Aib

<400> SEQUENCE: 48

Ser Val Ser Glu Ile Gln Leu Met His Asn Leu Gly Lys His Leu Xaa
1               5                   10                  15

Ser Met Glu Arg Val Glu Trp Leu Arg Lys Lys Leu Gln Asp Val His
            20                  25                  30

Asn Phe

<210> SEQ ID NO 49
<211> LENGTH: 34
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: Aib

<400> SEQUENCE: 49

Ser Val Ser Glu Ile Gln Leu Met His Asn Leu Gly Lys His Leu Asn
1               5                   10                  15

Ser Met Xaa Arg Val Glu Trp Leu Arg Lys Lys Leu Gln Asp Val His
            20                  25                  30

Asn Phe

<210> SEQ ID NO 50
<211> LENGTH: 34
<212> TYPE: PRT
<213> ORGANISM: Homo sapiens
<220> FEATURE:
<221> NAME/KEY: MOD_RES
<222> LOCATION: (34)..(34)
<223> OTHER INFORMATION: Aib

<400> SEQUENCE: 50

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Xaa

<210> SEQ ID NO 51
<211> LENGTH: 34
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (19)..(19)
<223> OTHER INFORMATION: Aib

<400> SEQUENCE: 51

Ser Val Ser Glu Ile Gln Leu Met His Asn Leu Gly Lys His Leu Xaa
1               5                   10                  15

Ser Met Xaa Arg Val Glu Trp Leu Arg Lys Lys Leu Gln Asp Val His
            20                  25                  30

Asn Phe
```

<210> SEQ ID NO 52
<211> LENGTH: 34
<212> TYPE: PRT
<213> ORGANISM: Bos sp.
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (19)..(19)
<223> OTHER INFORMATION: Aib
<220> FEATURE:
<221> NAME/KEY: MOD_RES
<222> LOCATION: (34)..(34)
<223> OTHER INFORMATION: Aib

<400> SEQUENCE: 52

Ala Val Ser Glu Ile Gln Phe Met His Asn Leu Gly Lys His Leu Xaa
1               5                   10                  15

Ser Met Xaa Arg Val Glu Trp Leu Arg Lys Lys Leu Gln Asp Val His
            20                  25                  30

Asn Xaa

<210> SEQ ID NO 53
<211> LENGTH: 34
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (34)..(34)
<223> OTHER INFORMATION: Aib

<400> SEQUENCE: 53

Ser Val Ser Glu Ile Gln Leu Met His Asn Leu Gly Lys His Leu Xaa
1               5                   10                  15

Ser Met Glu Arg Val Glu Trp Leu Arg Lys Lys Leu Gln Asp Val His
            20                  25                  30

Asn Xaa

<210> SEQ ID NO 54
<211> LENGTH: 34
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: Aib
<220> FEATURE:
<221> NAME/KEY: MOD_RES
<222> LOCATION: (34)..(34)
<223> OTHER INFORMATION: Aib

<400> SEQUENCE: 54

Ser Val Ser Glu Ile Gln Leu Met His Asn Leu Gly Lys His Leu Asn
1               5                   10                  15

Ser Met Xaa Arg Val Glu Trp Leu Arg Lys Lys Leu Gln Asp Val His
            20                  25                  30

Asn Xaa

<210> SEQ ID NO 55
<211> LENGTH: 34

```
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (18)..(18)
<223> OTHER INFORMATION: Nle
<220> FEATURE:
<221> NAME/KEY: MOD_RES
<222> LOCATION: (19)..(19)
<223> OTHER INFORMATION: Aib

<400> SEQUENCE: 55

Ser Val Ser Glu Ile Gln Xaa Xaa His Asn Xaa Gly Lys His Leu Xaa
1               5                   10                  15
Ser Xaa Xaa Arg Val Glu Trp Leu Arg Lys Lys Leu Gln Asp Val His
            20                  25                  30
Asn Tyr

<210> SEQ ID NO 56
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (18)..(18)
<223> OTHER INFORMATION: Nle
<220> FEATURE:
<221> NAME/KEY: MOD_RES
<222> LOCATION: (19)..(19)
<223> OTHER INFORMATION: Aib
<220> FEATURE:
<221> NAME/KEY: MOD_RES
<222> LOCATION: (31)..(31)
<223> OTHER INFORMATION: Nle

<400> SEQUENCE: 56

Ser Val Ser Glu Ile Gln Xaa Xaa His Asn Xaa Gly Lys His Leu Xaa
1               5                   10                  15
Ser Xaa Xaa Arg Val Glu Trp Leu Arg Lys Lys Leu Gln Asp Xaa His
            20                  25                  30
```

-continued

Asn Tyr

<210> SEQ ID NO 57
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (16)..(16)
<223> OTHER INFORMATION: Aib

<400> SEQUENCE: 57

Ser Val Ser Glu Ile Gln Xaa Met His Asn Leu Gly Lys His Leu Xaa
1               5                   10                  15

Ser Met Glu Arg Val Glu Trp Leu Arg Lys Lys Leu Gln Asp Val His
            20                  25                  30

Asn Phe

<210> SEQ ID NO 58
<211> LENGTH: 34
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (16)..(16)
<223> OTHER INFORMATION: Aib

<400> SEQUENCE: 58

Ser Val Ser Glu Ile Gln Leu Met His Asn Xaa Gly Lys His Leu Xaa
1               5                   10                  15

Ser Met Glu Arg Val Glu Trp Leu Arg Lys Lys Leu Gln Asp Val His
            20                  25                  30

Asn Phe

<210> SEQ ID NO 59
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (34)..(34)
<223> OTHER INFORMATION: Aib

<400> SEQUENCE: 59

Ser Val Ser Glu Ile Gln Xaa Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Xaa

<210> SEQ ID NO 60
<211> LENGTH: 34
<212> TYPE: PRT
<213> ORGANISM: Homo sapiens

```
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (34)..(34)
<223> OTHER INFORMATION: Aib

<400> SEQUENCE: 60

Ser Val Ser Glu Ile Gln Leu Met His Asn Xaa Gly Lys His Leu Asn
1               5                   10                  15
Ser Met Glu Arg Val Glu Trp Leu Arg Lys Lys Leu Gln Asp Val His
            20                  25                  30
Asn Xaa

<210> SEQ ID NO 61
<211> LENGTH: 34
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (27)..(27)
<223> OTHER INFORMATION: Cha

<400> SEQUENCE: 61

Ser Val Ser Glu Ile Gln Leu Met His Asn Leu Gly Lys His Leu Xaa
1               5                   10                  15
Ser Met Glu Arg Val Glu Trp Leu Arg Lys Xaa Leu Gln Asp Val His
            20                  25                  30
Asn Phe

<210> SEQ ID NO 62
<211> LENGTH: 34
<212> TYPE: PRT
<213> ORGANISM: Homo sapiens
<220> FEATURE:
<221> NAME/KEY: MOD_RES
<222> LOCATION: (27)..(27)
<223> OTHER INFORMATION: Cha
<220> FEATURE:
<221> NAME/KEY: MOD_RES
<222> LOCATION: (34)..(34)
<223> OTHER INFORMATION: Aib

<400> SEQUENCE: 62

Ser Val Ser Glu Ile Gln Leu Met His Asn Leu Gly Lys His Leu Asn
1               5                   10                  15
Ser Met Glu Arg Val Glu Trp Leu Arg Lys Xaa Leu Gln Asp Val His
            20                  25                  30
Asn Xaa

<210> SEQ ID NO 63
<211> LENGTH: 34
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (28)..(28)
```

<223> OTHER INFORMATION: Cha

<400> SEQUENCE: 63

Ser Val Ser Glu Ile Gln Leu Met His Asn Leu Gly Lys His Leu Xaa
1               5                   10                  15

Ser Met Glu Arg Val Glu Trp Leu Arg Lys Lys Xaa Gln Asp Val His
            20                  25                  30

Asn Phe

<210> SEQ ID NO 64
<211> LENGTH: 34
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: Cha
<220> FEATURE:
<221> NAME/KEY: MOD_RES
<222> LOCATION: (34)..(34)
<223> OTHER INFORMATION: Aib

<400> SEQUENCE: 64

Ser Val Ser Glu Ile Gln Leu Met His Asn Leu Gly Lys His Leu Asn
1               5                   10                  15

Ser Met Glu Arg Val Glu Trp Leu Arg Lys Lys Xaa Gln Asp Val His
            20                  25                  30

Asn Xaa

<210> SEQ ID NO 65
<211> LENGTH: 34
<212> TYPE: PRT
<213> ORGANISM: Homo sapiens
<220> FEATURE:
<221> NAME/KEY: MOD_RES
<222> LOCATION: (31)..(31)
<223> OTHER INFORMATION: Nle

<400> SEQUENCE: 65

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Xaa His
            20                  25                  30

Asn Phe

<210> SEQ ID NO 66
<211> LENGTH: 34
<212> TYPE: PRT
<213> ORGANISM: Homo sapiens
<220> FEATURE:
<221> NAME/KEY: MOD_RES
<222> LOCATION: (27)..(27)
<223> OTHER INFORMATION: hArg

<400> SEQUENCE: 66

Ser Val Ser Glu Ile Gln Leu Met His Asn Leu Gly Lys His Leu Asn
1               5                   10                  15

Ser Met Glu Arg Val Glu Trp Leu Arg Lys Arg Leu Gln Asp Val His
            20                  25                  30

Asn Phe

<210> SEQ ID NO 67
<211> LENGTH: 34

```
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Dap
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (18)..(18)
<223> OTHER INFORMATION: Nle

<400> SEQUENCE: 67

Xaa Val Ser Glu Ile Gln Leu Xaa His Asn Leu Gly Lys His Leu Asn
1               5                   10                  15

Ser Xaa Glu Arg Val Glu Trp Leu Arg Lys Lys Leu Gln Asp Val His
            20                  25                  30

Asn Tyr

<210> SEQ ID NO 68
<211> LENGTH: 34
<212> TYPE: PRT
<213> ORGANISM: Bos sp.
<220> FEATURE:
<221> NAME/KEY: MOD_RES
<222> LOCATION: (31)..(31)
<223> OTHER INFORMATION: Nle

<400> SEQUENCE: 68

Ala Val Ser Glu Ile Gln Phe Met His Asn Leu Gly Lys His Leu Ser
1               5                   10                  15

Ser Met Glu Arg Val Glu Trp Leu Arg Lys Lys Leu Gln Asp Xaa His
            20                  25                  30

Asn Phe

<210> SEQ ID NO 69
<211> LENGTH: 34
<212> TYPE: PRT
<213> ORGANISM: Rattus sp.
<220> FEATURE:
<221> NAME/KEY: MOD_RES
<222> LOCATION: (31)..(31)
<223> OTHER INFORMATION: Nle

<400> SEQUENCE: 69

Ala Val Ser Glu Ile Gln Leu Met His Asn Leu Gly Lys His Leu Ala
1               5                   10                  15

Ser Val Glu Arg Met Gln Trp Leu Arg Lys Lys Leu Gln Asp Xaa His
            20                  25                  30

Asn Phe

<210> SEQ ID NO 70
<211> LENGTH: 34
<212> TYPE: PRT
<213> ORGANISM: Bos sp.
<220> FEATURE:
<221> NAME/KEY: MOD_RES
<222> LOCATION: (27)..(27)
<223> OTHER INFORMATION: hArg

<400> SEQUENCE: 70

Ala Val Ser Glu Ile Gln Phe Met His Asn Leu Gly Lys His Leu Ser
1               5                   10                  15
```

Ser Met Glu Arg Val Glu Trp Leu Arg Lys Arg Leu Gln Asp Val His
            20                  25                  30

Asn Phe

<210> SEQ ID NO 71
<211> LENGTH: 34
<212> TYPE: PRT
<213> ORGANISM: Rattus sp.
<220> FEATURE:
<221> NAME/KEY: MOD_RES
<222> LOCATION: (27)..(27)
<223> OTHER INFORMATION: hArg

<400> SEQUENCE: 71

Ala Val Ser Glu Ile Gln Leu Met His Asn Leu Gly Lys His Leu Ala
1               5                   10                  15

Ser Val Glu Arg Met Gln Trp Leu Arg Lys Arg Leu Gln Asp Val His
            20                  25                  30

Asn Phe

<210> SEQ ID NO 72
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (19)..(19)
<223> OTHER INFORMATION: Aib

<400> SEQUENCE: 72

Ser Val Ser Glu Ile Gln Xaa Met His Asn Xaa Gly Lys His Leu Asn
1               5                   10                  15

Ser Met Xaa Arg Val Glu Trp Leu Arg Lys Lys Leu Gln Lys Val His
            20                  25                  30

Asn Phe

<210> SEQ ID NO 73
<211> LENGTH: 34
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Aib

<400> SEQUENCE: 73

Ser Val Ser Glu Ile Gln Leu Met His Asn Leu Xaa Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 74
<211> LENGTH: 34
<212> TYPE: PRT
<213> ORGANISM: Homo sapiens

```
<220> FEATURE:
<221> NAME/KEY: MOD_RES
<222> LOCATION: (24)..(24)
<223> OTHER INFORMATION: Cha
<220> FEATURE:
<221> NAME/KEY: MOD_RES
<222> LOCATION: (28)..(28)
<223> OTHER INFORMATION: Cha
<220> FEATURE:
<221> NAME/KEY: MOD_RES
<222> LOCATION: (31)..(31)
<223> OTHER INFORMATION: Cha

<400> SEQUENCE: 74

Ser Val Ser Glu Ile Gln Leu Met His Asn Leu Gly Lys His Leu Asn
1               5                   10                  15

Ser Met Glu Arg Val Glu Trp Xaa Arg Lys Lys Xaa Gln Lys Xaa His
            20                  25                  30

Asn Phe

<210> SEQ ID NO 75
<211> LENGTH: 34
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: Cha
<220> FEATURE:
<221> NAME/KEY: MOD_RES
<222> LOCATION: (31)..(31)
<223> OTHER INFORMATION: Cha

<400> SEQUENCE: 75

Ser Val Ser Glu Ile Gln Leu Met His Asn Leu Gly Lys His Leu Asn
1               5                   10                  15

Ser Met Glu Arg Val Glu Trp Leu Arg Lys Lys Xaa Gln Asp Xaa His
            20                  25                  30

Asn Phe

<210> SEQ ID NO 76
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (18)..(18)
<223> OTHER INFORMATION: Nle
<220> FEATURE:
<221> NAME/KEY: MOD_RES
<222> LOCATION: (34)..(34)
<223> OTHER INFORMATION: Aib

<400> SEQUENCE: 76

Ser Val Ser Glu Ile Gln Xaa Xaa His Asn Xaa Gly Lys His Leu Asn
1               5                   10                  15

Ser Xaa Glu Arg Val Glu Trp Leu Arg Lys Lys Leu Gln Asp Val His
```

20                  25                  30

Asn Xaa

<210> SEQ ID NO 77
<211> LENGTH: 34
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Aib

<400> SEQUENCE: 77

Ser Val Xaa Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                    20                  25                  30

Asn Phe

<210> SEQ ID NO 78
<211> LENGTH: 34
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Cha

<400> SEQUENCE: 78

Ser Val Ser Glu Ile Gln Leu Xaa His Asn Leu Gly Lys His Leu Asn
1               5                   10                  15

Ser Met Glu Arg Val Glu Trp Leu Arg Lys Lys Leu Gln Asp Val His
                    20                  25                  30

Asn Phe

<210> SEQ ID NO 79
<211> LENGTH: 34
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Cha

<400> SEQUENCE: 79

Ser Val Ser Glu Ile Gln Leu Met His Asn Leu Gly Lys His Xaa Asn
1               5                   10                  15

Ser Met Glu Arg Val Glu Trp Leu Arg Lys Lys Leu Gln Asp Val His
                    20                  25                  30

Asn Phe

<210> SEQ ID NO 80
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (19)..(19)
<223> OTHER INFORMATION: Aib

<400> SEQUENCE: 80

Ser Val Ser Glu Ile Gln Xaa Met His Asn Xaa Gly Lys His Leu Asn
1               5                   10                  15

Ser Met Xaa Arg Val Glu Trp Leu Arg Lys Lys Leu Gln Asp Val His
            20                  25                  30

Asn Phe

<210> SEQ ID NO 81
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (16)..(16)
<223> OTHER INFORMATION: Aib

<400> SEQUENCE: 81

Ser Val Ser Glu Ile Gln Xaa Met His Asn Xaa Gly Lys His Leu Xaa
1               5                   10                  15

Ser Met Glu Arg Val Glu Trp Leu Arg Lys Lys Leu Gln Asp Val His
            20                  25                  30

Asn Phe

<210> SEQ ID NO 82
<211> LENGTH: 34
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Aib

<400> SEQUENCE: 82

Ser Val Ser Glu Ile Gln Leu Met His Asn Leu Gly Lys His Leu Asn
1               5                   10                  15

Xaa Met Glu Arg Val Glu Trp Leu Arg Lys Lys Leu Gln Asp Val His
            20                  25                  30

Asn Phe

<210> SEQ ID NO 83
<211> LENGTH: 34
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Cha

<400> SEQUENCE: 83

Ser Val Ser Glu Xaa Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

-continued

Asn Phe

<210> SEQ ID NO 84
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (15)..(15)
<223> OTHER INFORMATION: Cha

<400> SEQUENCE: 84

Ser Val Ser Glu Ile Gln Xaa Met His Asn Xaa Gly Lys His Xaa Asn
1               5                   10                  15

Ser Met Glu Arg Val Glu Trp Leu Arg Lys Lys Leu Gln Asp Val His
            20                  25                  30

Asn Phe

<210> SEQ ID NO 85
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (18)..(18)
<223> OTHER INFORMATION: Nle
<220> FEATURE:
<221> NAME/KEY: MOD_RES
<222> LOCATION: (19)..(19)
<223> OTHER INFORMATION: Aib

<400> SEQUENCE: 85

Ser Val Ser Glu Ile Gln Xaa Xaa His Asn Xaa Gly Lys His Leu Asn
1               5                   10                  15

Ser Xaa Xaa Arg Val Glu Trp Leu Arg Lys Lys Leu Gln Asp Val His
            20                  25                  30

Asn Tyr

<210> SEQ ID NO 86
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (8)..(8)
<223> OTHER INFORMATION: Nle

```
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (18)..(18)
<223> OTHER INFORMATION: Nle
<220> FEATURE:
<221> NAME/KEY: MOD_RES
<222> LOCATION: (19)..(19)
<223> OTHER INFORMATION: Aib

<400> SEQUENCE: 86

Ser Val Ser Glu Ile Gln Xaa Xaa His Asn Xaa Gly Lys His Leu Asn
1               5                   10                  15

Ser Xaa Xaa Arg Val Glu Trp Leu Arg Lys Lys Leu Gln Lys Val His
            20                  25                  30

Asn Tyr

<210> SEQ ID NO 87
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (15)..(15)
<223> OTHER INFORMATION: Cha

<400> SEQUENCE: 87

Ser Val Ser Glu Ile Gln Xaa Met His Asn Xaa Gly Lys His Xaa Asn
1               5                   10                  15

Ser Met Glu Arg Val Glu Trp Leu Arg Lys Lys Leu Gln Asp Val His
            20                  25                  30

Asn Phe

<210> SEQ ID NO 88
<211> LENGTH: 34
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Aib

<400> SEQUENCE: 88

Ser Val Ser Glu Ile Gln Leu Met His Asn Leu Gly Lys His Leu Asn
1               5                   10                  15

Xaa Met Glu Arg Val Glu Trp Leu Arg Lys Lys Leu Gln Asp Val His
            20                  25                  30

Asn Phe

<210> SEQ ID NO 89
<211> LENGTH: 34
<212> TYPE: PRT
<213> ORGANISM: Homo sapiens
<220> FEATURE:
<221> NAME/KEY: MOD_RES
<222> LOCATION: (7)..(7)
```

```
<223> OTHER INFORMATION: Cha
<220> FEATURE:
<221> NAME/KEY: MOD_RES
<222> LOCATION: (11)..(11)
<223> OTHER INFORMATION: Cha

<400> SEQUENCE: 89

Ser Val Ser Glu Ile Gln Xaa Met His Asn Xaa Gly Lys His Leu Asn
1               5                   10                  15

Ser Met Glu Arg Val Glu Trp Leu Arg Lys Leu Leu Gln Asp Val His
            20                  25                  30

Asn Phe

<210> SEQ ID NO 90
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (15)..(15)
<223> OTHER INFORMATION: Cha

<400> SEQUENCE: 90

Ser Val Ser Glu Ile Gln Xaa Met His Asn Xaa Gly Lys His Xaa Asn
1               5                   10                  15

Ser Met Glu Arg Val Glu Trp Leu Arg Lys Leu Leu Gln Asp Val His
            20                  25                  30

Asn Phe

<210> SEQ ID NO 91
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (27)..(27)
<223> OTHER INFORMATION: Cha

<400> SEQUENCE: 91

Ser Val Ser Glu Ile Gln Xaa Met His Asn Xaa Gly Lys His Leu Asn
1               5                   10                  15

Ser Met Glu Arg Val Glu Trp Leu Arg Lys Xaa Leu Gln Asp Val His
            20                  25                  30

Asn Phe

<210> SEQ ID NO 92
<211> LENGTH: 34
<212> TYPE: PRT
<213> ORGANISM: Homo sapiens
<220> FEATURE:
<221> NAME/KEY: MOD_RES
```

```
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (15)..(15)
<223> OTHER INFORMATION: Cha
<220> FEATURE:
<221> NAME/KEY: MOD_RES
<222> LOCATION: (27)..(27)
<223> OTHER INFORMATION: Cha

<400> SEQUENCE: 92

Ser Val Ser Glu Ile Gln Xaa Met His Asn Xaa Gly Lys His Xaa Asn
1               5                  10                  15

Ser Met Glu Arg Val Glu Trp Leu Arg Lys Xaa Leu Gln Asp Val His
            20                  25                  30

Asn Phe

<210> SEQ ID NO 93
<211> LENGTH: 34
<212> TYPE: PRT
<213> ORGANISM: Homo sapiens

<400> SEQUENCE: 93

Ser Val Ser Glu Ile Gln Leu Met His Asn Leu Gly Lys His Trp Asn
1               5                  10                  15

Ser Met Glu Arg Val Glu Trp Leu Arg Lys Lys Leu Gln Asp Val His
            20                  25                  30

Asn Phe

<210> SEQ ID NO 94
<211> LENGTH: 34
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Nal

<400> SEQUENCE: 94

Ser Val Ser Glu Ile Gln Leu Met His Asn Leu Gly Lys His Xaa Asn
1               5                  10                  15

Ser Met Glu Arg Val Glu Trp Leu Arg Lys Lys Leu Gln Asp Val His
            20                  25                  30

Asn Phe

<210> SEQ ID NO 95
<211> LENGTH: 34
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: Cha

<400> SEQUENCE: 95

Ser Val Ser Glu Ile Gln Leu Met His Asn Leu Gly Lys His Trp Asn
1               5                  10                  15

Ser Met Glu Arg Val Glu Xaa Leu Arg Lys Lys Leu Gln Asp Val His
            20                  25                  30
```

```
<210> SEQ ID NO 96
<211> LENGTH: 34
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Cha
<220> FEATURE:
<221> NAME/KEY: MOD_RES
<222> LOCATION: (23)..(23)
<223> OTHER INFORMATION: Cha

<400> SEQUENCE: 96

Ser Val Ser Glu Ile Gln Leu Met His Asn Leu Gly Lys His Xaa Asn
1               5                   10                  15

Ser Met Glu Arg Val Glu Xaa Leu Arg Lys Lys Leu Gln Asp Val His
                20                  25                  30

Asn Phe

<210> SEQ ID NO 97
<211> LENGTH: 34
<212> TYPE: PRT
<213> ORGANISM: Homo sapiens

<400> SEQUENCE: 97

Ser Val Ser Glu Ile Gln Phe Met His Asn Phe Gly Lys His Leu Asn
1               5                   10                  15

Ser Met Glu Arg Val Glu Trp Leu Arg Lys Lys Leu Gln Asp Val His
                20                  25                  30

Asn Phe

<210> SEQ ID NO 98
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Nal
<220> FEATURE:
<221> NAME/KEY: MOD_RES
<222> LOCATION: (11)..(11)
<223> OTHER INFORMATION: Nal

<400> SEQUENCE: 98

Ser Val Ser Glu Ile Gln Xaa Met His Asn Xaa Gly Lys His Leu Asn
1               5                   10                  15

Ser Met Glu Arg Val Glu Trp Leu Arg Lys Lys Leu Gln Asp Val His
                20                  25                  30

Asn Phe

<210> SEQ ID NO 99
<211> LENGTH: 34
<212> TYPE: PRT
<213> ORGANISM: Homo sapiens

<400> SEQUENCE: 99

Ser Val Ser Glu Ile Gln Trp Met His Asn Trp Gly Lys His Leu Asn
1               5                   10                  15

Ser Met Glu Arg Val Glu Trp Leu Arg Lys Lys Leu Gln Asp Val His
                20                  25                  30
```

Asn Phe

<210> SEQ ID NO 100
<211> LENGTH: 34
<212> TYPE: PRT
<213> ORGANISM: Homo sapiens

<400> SEQUENCE: 100

Ser Val Ser Glu Ile Gln Phe Met His Asn Phe Gly Lys His Phe Asn
1               5                   10                  15

Ser Met Glu Arg Val Glu Trp Leu Arg Lys Lys Leu Gln Asp Val His
            20                  25                  30

Asn Phe

<210> SEQ ID NO 101
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Nal
<220> FEATURE:
<221> NAME/KEY: MOD_RES
<222> LOCATION: (11)..(11)
<223> OTHER INFORMATION: Nal
<220> FEATURE:
<221> NAME/KEY: MOD_RES
<222> LOCATION: (15)..(15)
<223> OTHER INFORMATION: Nal

<400> SEQUENCE: 101

Ser Val Ser Glu Ile Gln Xaa Met His Asn Xaa Gly Lys His Xaa Asn
1               5                   10                  15

Ser Met Glu Arg Val Glu Trp Leu Arg Lys Lys Leu Gln Asp Val His
            20                  25                  30

Asn Phe

<210> SEQ ID NO 102
<211> LENGTH: 34
<212> TYPE: PRT
<213> ORGANISM: Homo sapiens

<400> SEQUENCE: 102

Ser Val Ser Glu Ile Gln Trp Met His Asn Trp Gly Lys His Trp Asn
1               5                   10                  15

Ser Met Glu Arg Val Glu Trp Leu Arg Lys Lys Leu Gln Asp Val His
            20                  25                  30

Asn Phe

<210> SEQ ID NO 103
<211> LENGTH: 34
<212> TYPE: PRT
<213> ORGANISM: Homo sapiens

<400> SEQUENCE: 103

Ser Val Ser Glu Ile Gln Tyr Met His Asn Tyr Gly Lys His Tyr Asn
1               5                   10                  15

Ser Met Glu Arg Val Glu Trp Leu Arg Lys Lys Leu Gln Asp Val His
            20                  25                  30

Asn Phe

<210> SEQ ID NO 104
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha

<400> SEQUENCE: 104

Met Gln Arg Arg Leu Val Xaa Gln Trp Ser Val Ala Val Phe Leu Leu
1               5                   10                  15

Ser Tyr Ala Val Pro Ser Cys Gly Arg Ser Val Glu Gly Leu Ser Arg
            20                  25                  30

Arg Leu

<210> SEQ ID NO 105
<211> LENGTH: 34
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Cha

<400> SEQUENCE: 105

Met Gln Arg Arg Leu Val Gln Gln Trp Ser Xaa Ala Val Phe Leu Leu
1               5                   10                  15

Ser Tyr Ala Val Pro Ser Cys Gly Arg Ser Val Glu Gly Leu Ser Arg
            20                  25                  30

Arg Leu

<210> SEQ ID NO 106
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha

<400> SEQUENCE: 106

Met Gln Arg Arg Leu Val Xaa Gln Trp Ser Xaa Ala Val Phe Leu Leu
1               5                   10                  15

Ser Tyr Ala Val Pro Ser Cys Gly Arg Ser Val Glu Gly Leu Ser Arg
            20                  25                  30

Arg Leu

<210> SEQ ID NO 107
<211> LENGTH: 34
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Aib

<400> SEQUENCE: 107

Met Gln Arg Arg Leu Val Gln Gln Trp Ser Val Ala Val Phe Leu Xaa
1               5                   10                  15

-continued

Ser Tyr Ala Val Pro Ser Cys Gly Arg Ser Val Glu Gly Leu Ser Arg
            20                  25                  30

Arg Tyr

<210> SEQ ID NO 108
<211> LENGTH: 34
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: Aib

<400> SEQUENCE: 108

Met Gln Arg Arg Leu Val Gln Gln Trp Ser Val Ala Val Phe Leu Leu
1               5                   10                  15

Ser Tyr Xaa Val Pro Ser Cys Gly Arg Ser Val Glu Gly Leu Ser Arg
            20                  25                  30

Arg Leu

<210> SEQ ID NO 109
<211> LENGTH: 34
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (19)..(19)
<223> OTHER INFORMATION: Aib

<400> SEQUENCE: 109

Met Gln Arg Arg Leu Val Gln Gln Trp Ser Val Ala Val Phe Leu Xaa
1               5                   10                  15

Ser Tyr Xaa Val Pro Ser Cys Gly Arg Ser Val Glu Gly Leu Ser Arg
            20                  25                  30

Arg Leu

<210> SEQ ID NO 110
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (16)..(16)
<223> OTHER INFORMATION: Aib

<400> SEQUENCE: 110

Met Gln Arg Arg Leu Val Xaa Gln Trp Ser Xaa Ala Val Phe Leu Xaa
1               5                   10                  15

Ser Tyr Ala Val Pro Ser Cys Gly Arg Ser Val Glu Gly Leu Ser Arg
            20                  25                  30

Arg Leu

<210> SEQ ID NO 111

```
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (19)..(19)
<223> OTHER INFORMATION: Aib

<400> SEQUENCE: 111

Met Gln Arg Arg Leu Val Xaa Gln Trp Ser Xaa Ala Val Phe Leu Leu
1               5                   10                  15

Ser Tyr Xaa Val Pro Ser Cys Gly Arg Ser Val Glu Gly Leu Ser Arg
            20                  25                  30

Arg Leu

<210> SEQ ID NO 112
<211> LENGTH: 34
<212> TYPE: PRT
<213> ORGANISM: Homo sapiens
<220> FEATURE:
<221> NAME/KEY: MOD_RES
<222> LOCATION: (22)..(22)
<223> OTHER INFORMATION: Cha

<400> SEQUENCE: 112

Met Gln Arg Arg Leu Val Gln Gln Trp Ser Val Ala Val Phe Leu Leu
1               5                   10                  15

Ser Tyr Ala Val Pro Xaa Leu Gly Glu Lys Val Leu Glu Lys Leu Arg
            20                  25                  30

Arg Leu

<210> SEQ ID NO 113
<211> LENGTH: 34
<212> TYPE: PRT
<213> ORGANISM: Homo sapiens

<400> SEQUENCE: 113

Met Gln Arg Arg Leu Val Gln Gln Trp Ser Val Ala Val Phe Leu Leu
1               5                   10                  15

Ser Tyr Ala Val Pro Glu Leu Gly Glu Lys Lys Leu Glu Lys Leu Arg
            20                  25                  30

Arg Leu

<210> SEQ ID NO 114
<211> LENGTH: 34
<212> TYPE: PRT
<213> ORGANISM: Homo sapiens
<220> FEATURE:
<221> NAME/KEY: MOD_RES
<222> LOCATION: (22)..(23)
<223> OTHER INFORMATION: Cha

<400> SEQUENCE: 114

Met Gln Arg Arg Leu Val Gln Gln Trp Ser Val Ala Val Phe Leu Leu
1               5                   10                  15

Ser Tyr Ala Val Pro Xaa Xaa Gly Glu Lys Val Leu Glu Lys Leu Arg
            20                  25                  30
```

Arg Leu

<210> SEQ ID NO 115
<211> LENGTH: 34
<212> TYPE: PRT
<213> ORGANISM: Homo sapiens
<220> FEATURE:
<221> NAME/KEY: MOD_RES
<222> LOCATION: (29)..(29)
<223> OTHER INFORMATION: Aib

<400> SEQUENCE: 115

Met Gln Arg Arg Leu Val Gln Gln Trp Ser Val Ala Val Phe Leu Leu
1               5                   10                  15

Ser Tyr Ala Val Pro Glu Leu Gly Glu Lys Val Leu Xaa Lys Leu Arg
            20                  25                  30

Arg Leu

<210> SEQ ID NO 116
<211> LENGTH: 34
<212> TYPE: PRT
<213> ORGANISM: Homo sapiens

<400> SEQUENCE: 116

Met Gln Arg Arg Leu Val Gln Gln Trp Ser Val Ala Val Phe Leu Leu
1               5                   10                  15

Ser Tyr Ala Val Pro Glu Lys Gly Glu Lys Val Leu Glu Lys Leu Arg
            20                  25                  30

Arg Leu

<210> SEQ ID NO 117
<211> LENGTH: 34
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: Cha

<400> SEQUENCE: 117

Met Gln Arg Arg Leu Val Gln Gln Trp Ser Val Ala Val Phe Leu Leu
1               5                   10                  15

Ser Tyr Ala Val Pro Glu Leu Gly Glu Lys Val Leu Glu Xaa Leu Arg
            20                  25                  30

Arg Leu

<210> SEQ ID NO 118
<211> LENGTH: 34
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: Aib

<400> SEQUENCE: 118

Met Gln Arg Arg Leu Val Gln Gln Trp Ser Val Ala Val Phe Leu Leu
1               5                   10                  15

Ser Tyr Ala Val Pro Glu Leu Gly Glu Lys Val Leu Glu Xaa Leu Arg
            20                  25                  30

Arg Leu

<210> SEQ ID NO 119
<211> LENGTH: 34
<212> TYPE: PRT
<213> ORGANISM: Homo sapiens

<400> SEQUENCE: 119

Met Gln Arg Arg Leu Val Gln Gln Trp Ser Val Ala Val Phe Leu Leu
1               5                   10                  15

Ser Tyr Ala Val Pro Glu Leu Gly Glu Lys Val Lys Glu Lys Leu Arg
            20                  25                  30

Arg Leu

<210> SEQ ID NO 120
<211> LENGTH: 34
<212> TYPE: PRT
<213> ORGANISM: Homo sapiens
<220> FEATURE:
<221> NAME/KEY: MOD_RES
<222> LOCATION: (22)..(24)
<223> OTHER INFORMATION: Cha
<220> FEATURE:
<221> NAME/KEY: MOD_RES
<222> LOCATION: (27)..(28)
<223> OTHER INFORMATION: Cha
<220> FEATURE:
<221> NAME/KEY: MOD_RES
<222> LOCATION: (31)..(31)
<223> OTHER INFORMATION: Cha

<400> SEQUENCE: 120

Met Gln Arg Arg Leu Val Gln Gln Trp Ser Val Ala Val Phe Leu Leu
1               5                   10                  15

Ser Tyr Ala Val Pro Xaa Xaa Xaa Glu Lys Xaa Xaa Glu Lys Xaa Arg
            20                  25                  30

Arg Leu

<210> SEQ ID NO 121
<211> LENGTH: 34
<212> TYPE: PRT
<213> ORGANISM: Homo sapiens
<220> FEATURE:
<221> NAME/KEY: MOD_RES
<222> LOCATION: (23)..(24)
<223> OTHER INFORMATION: Cha
<220> FEATURE:
<221> NAME/KEY: MOD_RES
<222> LOCATION: (28)..(28)
<223> OTHER INFORMATION: Cha
<220> FEATURE:
<221> NAME/KEY: MOD_RES
<222> LOCATION: (31)..(31)
<223> OTHER INFORMATION: Cha

<400> SEQUENCE: 121

Met Gln Arg Arg Leu Val Gln Gln Trp Ser Val Ala Val Phe Leu Leu
1               5                   10                  15

Ser Tyr Ala Val Pro Glu Xaa Xaa Glu Lys Lys Xaa Glu Lys Xaa Arg
            20                  25                  30

Arg Leu

<210> SEQ ID NO 122
<211> LENGTH: 34
<212> TYPE: PRT
<213> ORGANISM: Homo sapiens
<220> FEATURE:
<221> NAME/KEY: MOD_RES

```
<222> LOCATION: (23)..(24)
<223> OTHER INFORMATION: Cha
<220> FEATURE:
<221> NAME/KEY: MOD_RES
<222> LOCATION: (27)..(27)
<223> OTHER INFORMATION: Cha
<220> FEATURE:
<221> NAME/KEY: MOD_RES
<222> LOCATION: (31)..(31)
<223> OTHER INFORMATION: Cha

<400> SEQUENCE: 122

Met Gln Arg Arg Leu Val Gln Gln Trp Ser Val Ala Val Phe Leu Leu
1               5                   10                  15

Ser Tyr Ala Val Pro Glu Xaa Xaa Glu Lys Xaa Lys Glu Lys Xaa Arg
            20                  25                  30

Arg Leu

<210> SEQ ID NO 123
<211> LENGTH: 34
<212> TYPE: PRT
<213> ORGANISM: Homo sapiens
<220> FEATURE:
<221> NAME/KEY: MOD_RES
<222> LOCATION: (24)..(24)
<223> OTHER INFORMATION: Cha
<220> FEATURE:
<221> NAME/KEY: MOD_RES
<222> LOCATION: (27)..(28)
<223> OTHER INFORMATION: Cha
<220> FEATURE:
<221> NAME/KEY: MOD_RES
<222> LOCATION: (31)..(31)
<223> OTHER INFORMATION: Cha

<400> SEQUENCE: 123

Met Gln Arg Arg Leu Val Gln Gln Trp Ser Val Ala Val Phe Leu Leu
1               5                   10                  15

Ser Tyr Ala Val Pro Glu Lys Xaa Glu Lys Xaa Xaa Glu Lys Xaa Arg
            20                  25                  30

Arg Leu

<210> SEQ ID NO 124
<211> LENGTH: 34
<212> TYPE: PRT
<213> ORGANISM: Homo sapiens
<220> FEATURE:
<221> NAME/KEY: MOD_RES
<222> LOCATION: (22)..(22)
<223> OTHER INFORMATION: Cha

<400> SEQUENCE: 124

Met Gln Arg Arg Leu Val Gln Gln Trp Ser Val Ala Val Phe Leu Leu
1               5                   10                  15

Ser Tyr Ala Val Pro Xaa Leu Gly Glu Lys Lys Leu Glu Lys Leu Arg
            20                  25                  30

Arg Leu

<210> SEQ ID NO 125
<211> LENGTH: 34
<212> TYPE: PRT
<213> ORGANISM: Homo sapiens
<220> FEATURE:
<221> NAME/KEY: MOD_RES
<222> LOCATION: (22)..(22)
<223> OTHER INFORMATION: Cha
```

```
<400> SEQUENCE: 125

Met Gln Arg Arg Leu Val Gln Gln Trp Ser Val Ala Val Phe Leu Leu
1               5                   10                  15

Ser Tyr Ala Val Pro Xaa Leu Gly Glu Lys Val Lys Glu Lys Leu Arg
            20                  25                  30

Arg Leu

<210> SEQ ID NO 126
<211> LENGTH: 34
<212> TYPE: PRT
<213> ORGANISM: Homo sapiens
<220> FEATURE:
<221> NAME/KEY: MOD_RES
<222> LOCATION: (22)..(22)
<223> OTHER INFORMATION: Cha

<400> SEQUENCE: 126

Met Gln Arg Arg Leu Val Gln Gln Trp Ser Val Ala Val Phe Leu Leu
1               5                   10                  15

Ser Tyr Ala Val Pro Xaa Lys Gly Glu Lys Val Leu Glu Lys Leu Arg
            20                  25                  30

Arg Leu

<210> SEQ ID NO 127
<211> LENGTH: 34
<212> TYPE: PRT
<213> ORGANISM: Homo sapiens
<220> FEATURE:
<221> NAME/KEY: MOD_RES
<222> LOCATION: (22)..(22)
<223> OTHER INFORMATION: Cha
<220> FEATURE:
<221> NAME/KEY: MOD_RES
<222> LOCATION: (29)..(29)
<223> OTHER INFORMATION: Aib

<400> SEQUENCE: 127

Met Gln Arg Arg Leu Val Gln Gln Trp Ser Val Ala Val Phe Leu Leu
1               5                   10                  15

Ser Tyr Ala Val Pro Xaa Leu Gly Glu Lys Val Leu Xaa Lys Leu Arg
            20                  25                  30

Arg Leu

<210> SEQ ID NO 128
<211> LENGTH: 34
<212> TYPE: PRT
<213> ORGANISM: Homo sapiens
<220> FEATURE:
<221> NAME/KEY: MOD_RES
<222> LOCATION: (22)..(22)
<223> OTHER INFORMATION: Cha
<220> FEATURE:
<221> NAME/KEY: MOD_RES
<222> LOCATION: (30)..(30)
<223> OTHER INFORMATION: Aib

<400> SEQUENCE: 128

Met Gln Arg Arg Leu Val Gln Gln Trp Ser Val Ala Val Phe Leu Leu
1               5                   10                  15

Ser Tyr Ala Val Pro Xaa Leu Gly Glu Lys Val Leu Glu Xaa Leu Arg
            20                  25                  30

Arg Leu
```

```
<210> SEQ ID NO 129
<211> LENGTH: 34
<212> TYPE: PRT
<213> ORGANISM: Homo sapiens
<220> FEATURE:
<221> NAME/KEY: MOD_RES
<222> LOCATION: (29)..(29)
<223> OTHER INFORMATION: Aib

<400> SEQUENCE: 129

Met Gln Arg Arg Leu Val Gln Gln Trp Ser Val Ala Val Phe Leu Leu
1               5                   10                  15

Ser Tyr Ala Val Pro Glu Leu Gly Glu Lys Lys Leu Xaa Lys Leu Arg
            20                  25                  30

Arg Leu

<210> SEQ ID NO 130
<211> LENGTH: 34
<212> TYPE: PRT
<213> ORGANISM: Homo sapiens
<220> FEATURE:
<221> NAME/KEY: MOD_RES
<222> LOCATION: (29)..(29)
<223> OTHER INFORMATION: Aib

<400> SEQUENCE: 130

Met Gln Arg Arg Leu Val Gln Gln Trp Ser Val Ala Val Phe Leu Leu
1               5                   10                  15

Ser Tyr Ala Val Pro Glu Lys Gly Glu Lys Val Leu Xaa Lys Leu Arg
            20                  25                  30

Arg Leu

<210> SEQ ID NO 131
<211> LENGTH: 34
<212> TYPE: PRT
<213> ORGANISM: Homo sapiens
<220> FEATURE:
<221> NAME/KEY: MOD_RES
<222> LOCATION: (29)..(29)
<223> OTHER INFORMATION: Aib

<400> SEQUENCE: 131

Met Gln Arg Arg Leu Val Gln Gln Trp Ser Val Ala Val Phe Leu Leu
1               5                   10                  15

Ser Tyr Ala Val Pro Glu Leu Gly Glu Lys Val Lys Xaa Lys Leu Arg
            20                  25                  30

Arg Leu

<210> SEQ ID NO 132
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha

<400> SEQUENCE: 132

Met Gln Arg Arg Leu Val Xaa Gln Trp Ser Xaa Ala Val Phe Leu Leu
1               5                   10                  15

Ser Tyr Ala Val Pro Glu Leu Gly Glu Lys Val Leu Glu Lys Leu Arg
```

```
              20                  25                  30

Arg Leu

<210> SEQ ID NO 133
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (22)..(22)
<223> OTHER INFORMATION: Cha

<400> SEQUENCE: 133

Met Gln Arg Arg Leu Val Xaa Gln Trp Ser Xaa Ala Val Phe Leu Leu
1               5                   10                  15

Ser Tyr Ala Val Pro Xaa Leu Gly Glu Lys Val Leu Glu Lys Leu Arg
            20                  25                  30

Arg Leu

<210> SEQ ID NO 134
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha

<400> SEQUENCE: 134

Met Gln Arg Arg Leu Val Xaa Gln Trp Ser Xaa Ala Val Phe Leu Leu
1               5                   10                  15

Ser Tyr Ala Val Pro Glu Leu Gly Glu Lys Lys Leu Glu Lys Leu Arg
            20                  25                  30

Arg Leu

<210> SEQ ID NO 135
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (22)..(23)
<223> OTHER INFORMATION: Cha

<400> SEQUENCE: 135

Met Gln Arg Arg Leu Val Xaa Gln Trp Ser Xaa Ala Val Phe Leu Leu
1               5                   10                  15
```

Ser Tyr Ala Val Pro Xaa Xaa Gly Glu Lys Val Leu Glu Lys Leu Arg
            20              25                  30

Arg Leu

<210> SEQ ID NO 136
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha

<400> SEQUENCE: 136

Met Gln Arg Arg Leu Val Xaa Gln Trp Ser Xaa Ala Val Phe Leu Leu
1               5                   10                  15

Ser Tyr Ala Val Pro Glu Lys Gly Glu Lys Val Leu Glu Lys Leu Arg
            20              25                  30

Arg Leu

<210> SEQ ID NO 137
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha

<400> SEQUENCE: 137

Met Gln Arg Arg Leu Val Xaa Gln Trp Ser Xaa Ala Val Phe Leu Leu
1               5                   10                  15

Ser Tyr Ala Val Pro Glu Leu Gly Glu Lys Val Lys Glu Lys Leu Arg
            20              25                  30

Arg Leu

<210> SEQ ID NO 138
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (29)..(29)
<223> OTHER INFORMATION: Aib

<400> SEQUENCE: 138

Met Gln Arg Arg Leu Val Xaa Gln Trp Ser Xaa Ala Val Phe Leu Leu
1               5                   10                  15

Ser Tyr Ala Val Pro Glu Leu Gly Glu Lys Val Leu Xaa Lys Leu Arg
            20              25                  30

Arg Leu

<210> SEQ ID NO 139
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (30)..(30)
<223> OTHER INFORMATION: Aib

<400> SEQUENCE: 139

Met Gln Arg Arg Leu Val Xaa Gln Trp Ser Xaa Ala Val Phe Leu Leu
1               5                   10                  15

Ser Tyr Ala Val Pro Glu Leu Gly Glu Lys Val Leu Glu Xaa Leu Arg
            20                  25                  30

Arg Leu

<210> SEQ ID NO 140
<211> LENGTH: 34
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Cha

<400> SEQUENCE: 140

Met Gln Arg Arg Leu Val Gln Gln Trp Ser Val Ala Val Phe Xaa Leu
1               5                   10                  15

Ser Tyr Ala Val Pro Glu Leu Gly Glu Lys Val Leu Glu Lys Leu Arg
            20                  25                  30

Arg Leu

<210> SEQ ID NO 141
<211> LENGTH: 34
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Cha
<220> FEATURE:
<221> NAME/KEY: MOD_RES
<222> LOCATION: (22)..(22)
<223> OTHER INFORMATION: Cha

<400> SEQUENCE: 141

Met Gln Arg Arg Leu Val Gln Gln Trp Ser Val Ala Val Phe Xaa Leu
1               5                   10                  15

Ser Tyr Ala Val Pro Xaa Leu Gly Glu Lys Val Leu Glu Lys Leu Arg
            20                  25                  30

Arg Leu

<210> SEQ ID NO 142
<211> LENGTH: 34
<212> TYPE: PRT
<213> ORGANISM: Homo sapiens

```
<220> FEATURE:
<221> NAME/KEY: MOD_RES
<222> LOCATION: (15)..(15)
<223> OTHER INFORMATION: Cha

<400> SEQUENCE: 142

Met Gln Arg Arg Leu Val Gln Gln Trp Ser Val Ala Val Phe Xaa Leu
1               5                   10                  15

Ser Tyr Ala Val Pro Glu Leu Gly Glu Lys Lys Leu Glu Lys Leu Arg
            20                  25                  30

Arg Leu

<210> SEQ ID NO 143
<211> LENGTH: 34
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Cha
<220> FEATURE:
<221> NAME/KEY: MOD_RES
<222> LOCATION: (22)..(23)
<223> OTHER INFORMATION: Cha

<400> SEQUENCE: 143

Met Gln Arg Arg Leu Val Gln Gln Trp Ser Val Ala Val Phe Xaa Leu
1               5                   10                  15

Ser Tyr Ala Val Pro Xaa Xaa Gly Glu Lys Val Leu Glu Lys Leu Arg
            20                  25                  30

Arg Leu

<210> SEQ ID NO 144
<211> LENGTH: 34
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Cha
<220> FEATURE:
<221> NAME/KEY: MOD_RES
<222> LOCATION: (29)..(29)
<223> OTHER INFORMATION: Aib

<400> SEQUENCE: 144

Met Gln Arg Arg Leu Val Gln Gln Trp Ser Val Ala Val Phe Xaa Leu
1               5                   10                  15

Ser Tyr Ala Val Pro Glu Leu Gly Glu Lys Val Leu Xaa Lys Leu Arg
            20                  25                  30

Arg Leu

<210> SEQ ID NO 145
<211> LENGTH: 34
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Cha

<400> SEQUENCE: 145

Met Gln Arg Arg Leu Val Gln Gln Trp Ser Val Ala Val Phe Xaa Leu
1               5                   10                  15

Ser Tyr Ala Val Pro Glu Lys Gly Glu Lys Val Leu Glu Lys Leu Arg
```

```
            20                  25                  30

Arg Leu

<210> SEQ ID NO 146
<211> LENGTH: 34
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Cha
<220> FEATURE:
<221> NAME/KEY: MOD_RES
<222> LOCATION: (30)..(30)
<223> OTHER INFORMATION: Aib

<400> SEQUENCE: 146

Met Gln Arg Arg Leu Val Gln Gln Trp Ser Val Ala Val Phe Xaa Leu
1               5                   10                  15

Ser Tyr Ala Val Pro Glu Leu Gly Glu Lys Val Leu Glu Xaa Leu Arg
            20                  25                  30

Arg Leu

<210> SEQ ID NO 147
<211> LENGTH: 34
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Cha

<400> SEQUENCE: 147

Met Gln Arg Arg Leu Val Gln Gln Trp Ser Val Ala Val Phe Xaa Leu
1               5                   10                  15

Ser Tyr Ala Val Pro Glu Leu Gly Glu Lys Val Lys Glu Lys Leu Arg
            20                  25                  30

Arg Leu

<210> SEQ ID NO 148
<211> LENGTH: 34
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: Cha
<220> FEATURE:
<221> NAME/KEY: MOD_RES
<222> LOCATION: (30)..(30)
<223> OTHER INFORMATION: Cha

<400> SEQUENCE: 148

Met Gln Arg Arg Leu Val Gln Gln Trp Ser Val Ala Val Phe Xaa Leu
1               5                   10                  15

Ser Tyr Ala Val Pro Glu Leu Gly Glu Lys Val Leu Glu Xaa Leu Arg
            20                  25                  30

Arg Leu

<210> SEQ ID NO 149
<211> LENGTH: 34
<212> TYPE: PRT
<213> ORGANISM: Homo sapiens
<220> FEATURE:
<221> NAME/KEY: MOD_RES
```

```
<222> LOCATION: (7)..(8)
<223> OTHER INFORMATION: Cha
<220> FEATURE:
<221> NAME/KEY: MOD_RES
<222> LOCATION: (22)..(22)
<223> OTHER INFORMATION: Cha

<400> SEQUENCE: 149
```

Met Gln Arg Arg Leu Val Xaa Xaa Trp Ser Val Ala Val Phe Leu Leu
1               5                   10                  15

Ser Tyr Ala Val Pro Xaa Leu Gly Glu Lys Val Leu Glu Lys Leu Arg
            20                  25                  30

Arg Leu

```
<210> SEQ ID NO 150
<211> LENGTH: 34
<212> TYPE: PRT
<213> ORGANISM: Homo sapiens
<220> FEATURE:
<221> NAME/KEY: MOD_RES
<222> LOCATION: (7)..(8)
<223> OTHER INFORMATION: Cha

<400> SEQUENCE: 150
```

Met Gln Arg Arg Leu Val Xaa Xaa Trp Ser Val Ala Val Phe Leu Leu
1               5                   10                  15

Ser Tyr Ala Val Pro Glu Glu Gly Glu Lys Lys Glu Leu Lys Glu Arg
            20                  25                  30

Arg Leu

```
<210> SEQ ID NO 151
<211> LENGTH: 34
<212> TYPE: PRT
<213> ORGANISM: Homo sapiens
<220> FEATURE:
<221> NAME/KEY: MOD_RES
<222> LOCATION: (7)..(8)
<223> OTHER INFORMATION: Cha
<220> FEATURE:
<221> NAME/KEY: MOD_RES
<222> LOCATION: (22)..(23)
<223> OTHER INFORMATION: Cha

<400> SEQUENCE: 151
```

Met Gln Arg Arg Leu Val Xaa Xaa Trp Ser Val Ala Val Phe Leu Leu
1               5                   10                  15

Ser Tyr Ala Val Pro Xaa Xaa Gly Glu Lys Val Leu Glu Lys Leu Arg
            20                  25                  30

Arg Leu

```
<210> SEQ ID NO 152
<211> LENGTH: 34
<212> TYPE: PRT
<213> ORGANISM: Homo sapiens
<220> FEATURE:
<221> NAME/KEY: MOD_RES
<222> LOCATION: (7)..(8)
<223> OTHER INFORMATION: Cha

<400> SEQUENCE: 152
```

Met Gln Arg Arg Leu Val Xaa Xaa Trp Ser Val Ala Val Phe Leu Leu
1               5                   10                  15

Ser Tyr Ala Val Pro Glu Leu Gly Glu Lys Val Leu Glu Lys Leu Arg
            20                  25                  30

-continued

Arg Leu

<210> SEQ ID NO 153
<211> LENGTH: 34
<212> TYPE: PRT
<213> ORGANISM: Homo sapiens
<220> FEATURE:
<221> NAME/KEY: MOD_RES
<222> LOCATION: (7)..(8)
<223> OTHER INFORMATION: Cha
<220> FEATURE:
<221> NAME/KEY: MOD_RES
<222> LOCATION: (29)..(29)
<223> OTHER INFORMATION: Aib

<400> SEQUENCE: 153

Met Gln Arg Arg Leu Val Xaa Xaa Trp Ser Val Ala Val Phe Leu Leu
1               5                   10                  15

Ser Tyr Ala Val Pro Glu Leu Gly Glu Lys Val Leu Xaa Lys Leu Arg
            20                  25                  30

Arg Leu

<210> SEQ ID NO 154
<211> LENGTH: 34
<212> TYPE: PRT
<213> ORGANISM: Homo sapiens
<220> FEATURE:
<221> NAME/KEY: MOD_RES
<222> LOCATION: (7)..(8)
<223> OTHER INFORMATION: Cha

<400> SEQUENCE: 154

Met Gln Arg Arg Leu Val Xaa Xaa Trp Ser Val Ala Val Phe Leu Leu
1               5                   10                  15

Ser Tyr Ala Val Pro Glu Lys Gly Glu Lys Val Leu Glu Lys Leu Arg
            20                  25                  30

Arg Leu

<210> SEQ ID NO 155
<211> LENGTH: 34
<212> TYPE: PRT
<213> ORGANISM: Homo sapiens
<220> FEATURE:
<221> NAME/KEY: MOD_RES
<222> LOCATION: (7)..(8)
<223> OTHER INFORMATION: Cha
<220> FEATURE:
<221> NAME/KEY: MOD_RES
<222> LOCATION: (30)..(30)
<223> OTHER INFORMATION: Aib

<400> SEQUENCE: 155

Met Gln Arg Arg Leu Val Xaa Xaa Trp Ser Val Ala Val Phe Leu Leu
1               5                   10                  15

Ser Tyr Ala Val Pro Glu Leu Gly Glu Lys Val Leu Glu Xaa Leu Arg
            20                  25                  30

Arg Leu

<210> SEQ ID NO 156
<211> LENGTH: 34
<212> TYPE: PRT
<213> ORGANISM: Homo sapiens
<220> FEATURE:
<221> NAME/KEY: MOD_RES
<222> LOCATION: (7)..(8)
<223> OTHER INFORMATION: Cha

```
<400> SEQUENCE: 156

Met Gln Arg Arg Leu Val Xaa Xaa Trp Ser Val Ala Val Phe Leu Leu
1               5                   10                  15

Ser Tyr Ala Val Pro Glu Leu Gly Glu Lys Val Lys Glu Lys Leu Arg
            20                  25                  30

Arg Leu

<210> SEQ ID NO 157
<211> LENGTH: 34
<212> TYPE: PRT
<213> ORGANISM: Homo sapiens
<220> FEATURE:
<221> NAME/KEY: MOD_RES
<222> LOCATION: (7)..(8)
<223> OTHER INFORMATION: Cha
<220> FEATURE:
<221> NAME/KEY: MOD_RES
<222> LOCATION: (30)..(30)
<223> OTHER INFORMATION: Cha

<400> SEQUENCE: 157

Met Gln Arg Arg Leu Val Xaa Xaa Trp Ser Val Ala Val Phe Leu Leu
1               5                   10                  15

Ser Tyr Ala Val Pro Glu Leu Gly Glu Lys Val Leu Glu Xaa Leu Arg
            20                  25                  30

Arg Leu

<210> SEQ ID NO 158
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (22)..(22)
<223> OTHER INFORMATION: Cha

<400> SEQUENCE: 158

Ser Gln Arg Arg Ile Val Xaa Met Trp Asn Xaa Ala Val His Leu Leu
1               5                   10                  15

Ser Tyr Ala Val Pro Xaa Leu Gly Glu Lys Val Leu Glu Lys Leu Arg
            20                  25                  30

Arg Leu

<210> SEQ ID NO 159
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha

<400> SEQUENCE: 159
```

```
Ser Gln Arg Arg Ile Val Xaa Met Trp Asn Xaa Ala Val His Leu Leu
1               5                   10                  15

Ser Tyr Ala Val Pro Glu Leu Gly Glu Lys Lys Leu Glu Lys Leu Arg
            20                  25                  30

Arg Leu
```

<210> SEQ ID NO 160
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha

<400> SEQUENCE: 160

```
Ser Gln Arg Arg Ile Val Xaa Met Trp Asn Xaa Ala Val His Leu Leu
1               5                   10                  15

Ser Tyr Ala Val Pro Glu Leu Gly Glu Lys Val Lys Glu Lys Leu Arg
            20                  25                  30

Arg Leu
```

<210> SEQ ID NO 161
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha

<400> SEQUENCE: 161

```
Ser Gln Arg Arg Ile Val Xaa Met Trp Asn Xaa Ala Val His Leu Leu
1               5                   10                  15

Ser Tyr Ala Val Pro Glu Lys Gly Glu Lys Val Leu Glu Lys Leu Arg
            20                  25                  30

Arg Leu
```

<210> SEQ ID NO 162
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (29)..(29)
<223> OTHER INFORMATION: Aib

<400> SEQUENCE: 162

```
Ser Gln Arg Arg Ile Val Xaa Met Trp Asn Xaa Ala Val His Leu Leu
1               5                   10                  15
```

-continued

Ser Tyr Ala Val Pro Glu Leu Gly Glu Lys Val Leu Xaa Lys Leu Arg
            20                  25                  30

Arg Leu

<210> SEQ ID NO 163
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (30)..(30)
<223> OTHER INFORMATION: Aib

<400> SEQUENCE: 163

Ser Gln Arg Arg Ile Val Xaa Met Trp Asn Xaa Ala Val His Leu Leu
1               5                   10                  15

Ser Tyr Ala Val Pro Glu Leu Gly Glu Lys Val Leu Glu Xaa Leu Arg
            20                  25                  30

Arg Leu

<210> SEQ ID NO 164
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (22)..(23)
<223> OTHER INFORMATION: Cha

<400> SEQUENCE: 164

Ser Gln Arg Arg Ile Val Xaa Met Trp Asn Xaa Ala Val His Leu Leu
1               5                   10                  15

Ser Tyr Ala Val Pro Xaa Xaa Gly Glu Lys Val Leu Glu Lys Leu Arg
            20                  25                  30

Arg Leu

<210> SEQ ID NO 165
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha
<220> FEATURE:
<221> NAME/KEY: MOD_RES
<222> LOCATION: (15)..(15)
<223> OTHER INFORMATION: Cha -continued

```
<400> SEQUENCE: 165

Ser Gln Arg Arg Ile Val Xaa Met Trp Asn Xaa Ala Val His Xaa Leu
1               5                   10                  15

Ser Tyr Ala Val Pro Ser Cys Gly Arg Ser Val Glu Gly Leu Ser Arg
            20                  25                  30

Arg Leu

<210> SEQ ID NO 166
<211> LENGTH: 34
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: Aib

<400> SEQUENCE: 166

Ser Gln Arg Arg Ile Val Gln Met Trp Asn Leu Ala Val His Leu Xaa
1               5                   10                  15

Ser Tyr Ala Val Pro Ser Cys Gly Arg Ser Val Glu Gly Leu Ser Arg
            20                  25                  30

Arg Leu

<210> SEQ ID NO 167
<211> LENGTH: 34
<212> TYPE: PRT
<213> ORGANISM: Homo sapiens
<220> FEATURE:
<221> NAME/KEY: MOD_RES
<222> LOCATION: (22)..(23)
<223> OTHER INFORMATION: Cha

<400> SEQUENCE: 167

Ser Gln Arg Arg Ile Val Gln Met Trp Asn Leu Ala Val His Leu Leu
1               5                   10                  15

Ser Tyr Ala Val Pro Xaa Xaa Gly Glu Lys Val Leu Glu Lys Leu Arg
            20                  25                  30

Arg Leu

<210> SEQ ID NO 168
<211> LENGTH: 34
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Cha
<220> FEATURE:
<221> NAME/KEY: MOD_RES
<222> LOCATION: (11)..(11)
<223> OTHER INFORMATION: Cha

<400> SEQUENCE: 168

Ser Gln Arg Arg Ile Val Xaa Met Trp Asn Xaa Ala Val His Leu Leu
1               5                   10                  15

Ser Tyr Ala Val Pro Glu Leu Gly Glu Lys Val Leu Glu Lys Leu Arg
            20                  25                  30

Arg Leu

<210> SEQ ID NO 169
<211> LENGTH: 34
<212> TYPE: PRT
<213> ORGANISM: Homo sapiens
```

```
<220> FEATURE:
<221> NAME/KEY: MOD_RES
<222> LOCATION: (15)..(15)
<223> OTHER INFORMATION: Cha

<400> SEQUENCE: 169

Ser Gln Arg Arg Ile Val Gln Met Trp Asn Val Ala Val His Xaa Leu
1               5                   10                  15

Ser Tyr Ala Val Pro Glu Leu Gly Glu Lys Val Leu Glu Lys Leu Arg
            20                  25                  30

Arg Leu

<210> SEQ ID NO 170
<211> LENGTH: 34
<212> TYPE: PRT
<213> ORGANISM: Homo sapiens
<220> FEATURE:
<221> NAME/KEY: MOD_RES
<222> LOCATION: (7)..(8)
<223> OTHER INFORMATION: Cha

<400> SEQUENCE: 170

Ser Gln Arg Arg Ile Val Xaa Xaa Trp Asn Val Ala Val His Leu Leu
1               5                   10                  15

Ser Tyr Ala Val Pro Glu Leu Gly Glu Lys Val Leu Glu Lys Leu Arg
            20                  25                  30

Arg Leu

<210> SEQ ID NO 171
<211> LENGTH: 34
<212> TYPE: PRT
<213> ORGANISM: Homo sapiens

<400> SEQUENCE: 171

Met Gln Arg Arg Leu Val Gln Gln Trp Ser Val Ala Val Phe Leu Leu
1               5                   10                  15

Ser Tyr Ala Val Pro Glu Leu Lys Glu Lys Val Leu Glu Lys Leu Arg
            20                  25                  30

Arg Leu

<210> SEQ ID NO 172
<211> LENGTH: 34
<212> TYPE: PRT
<213> ORGANISM: Homo sapiens
<220> FEATURE:
<221> NAME/KEY: MOD_RES
<222> LOCATION: (22)..(22)
<223> OTHER INFORMATION: Aib

<400> SEQUENCE: 172

Met Gln Arg Arg Leu Val Gln Gln Trp Ser Val Ala Val Phe Leu Leu
1               5                   10                  15

Ser Tyr Ala Val Pro Xaa Leu Gly Glu Lys Val Leu Glu Lys Leu Arg
            20                  25                  30

Arg Leu

<210> SEQ ID NO 173
<211> LENGTH: 34
<212> TYPE: PRT
<213> ORGANISM: Homo sapiens
<220> FEATURE:
<221> NAME/KEY: MOD_RES
<222> LOCATION: (25)..(25)
```

<223> OTHER INFORMATION: Aib

<400> SEQUENCE: 173

Met Gln Arg Arg Leu Val Gln Gln Trp Ser Val Ala Val Phe Leu Leu
1               5                   10                  15

Ser Tyr Ala Val Pro Glu Leu Gly Xaa Lys Val Leu Glu Lys Leu Arg
            20                  25                  30

Arg Leu

<210> SEQ ID NO 174
<211> LENGTH: 34
<212> TYPE: PRT
<213> ORGANISM: Homo sapiens
<220> FEATURE:
<221> NAME/KEY: MOD_RES
<222> LOCATION: (26)..(26)
<223> OTHER INFORMATION: Aib

<400> SEQUENCE: 174

Met Gln Arg Arg Leu Val Gln Gln Trp Ser Val Ala Val Phe Leu Leu
1               5                   10                  15

Ser Tyr Ala Val Pro Glu Leu Gly Glu Xaa Val Leu Glu Lys Leu Arg
            20                  25                  30

Arg Leu

<210> SEQ ID NO 175
<211> LENGTH: 34
<212> TYPE: PRT
<213> ORGANISM: Homo sapiens

<400> SEQUENCE: 175

Met Gln Arg Arg Leu Val Gln Gln Trp Ser Val Ala Val Phe Leu Leu
1               5                   10                  15

Ser Tyr Ala Val Pro Glu Leu Gly Glu Lys Val Leu Glu Lys Lys Arg
            20                  25                  30

Arg Leu

<210> SEQ ID NO 176
<211> LENGTH: 34
<212> TYPE: PRT
<213> ORGANISM: Homo sapiens
<220> FEATURE:
<221> NAME/KEY: MOD_RES
<222> LOCATION: (22)..(22)
<223> OTHER INFORMATION: Cha

<400> SEQUENCE: 176

Ser Gln Arg Arg Ile Val Gln Met Trp Asn Leu Ala Val His Leu Leu
1               5                   10                  15

Ser Tyr Ala Val Pro Xaa Leu Gly Glu Lys Val Leu Glu Lys Leu Arg
            20                  25                  30

Arg Leu

<210> SEQ ID NO 177
<211> LENGTH: 34
<212> TYPE: PRT
<213> ORGANISM: Homo sapiens

<400> SEQUENCE: 177

Ser Gln Arg Arg Ile Val Gln Met Trp Asn Leu Ala Val His Leu Leu
1               5                   10                  15

-continued

Ser Tyr Ala Val Pro Glu Lys Gly Glu Lys Val Leu Glu Lys Leu Arg
            20                  25                  30

Arg Leu

<210> SEQ ID NO 178
<211> LENGTH: 34
<212> TYPE: PRT
<213> ORGANISM: Homo sapiens

<400> SEQUENCE: 178

Ser Gln Arg Arg Ile Val Gln Met Trp Asn Leu Ala Val His Leu Leu
1               5                   10                  15

Ser Tyr Ala Val Pro Glu Leu Gly Glu Lys Lys Leu Glu Lys Leu Arg
            20                  25                  30

Arg Leu

<210> SEQ ID NO 179
<211> LENGTH: 34
<212> TYPE: PRT
<213> ORGANISM: Homo sapiens

<400> SEQUENCE: 179

Ser Gln Arg Arg Ile Val Gln Met Trp Asn Leu Ala Val His Leu Leu
1               5                   10                  15

Ser Tyr Ala Val Pro Glu Leu Gly Glu Lys Val Lys Glu Lys Leu Arg
            20                  25                  30

Arg Leu

<210> SEQ ID NO 180
<211> LENGTH: 34
<212> TYPE: PRT
<213> ORGANISM: Homo sapiens
<220> FEATURE:
<221> NAME/KEY: MOD_RES
<222> LOCATION: (29)..(29)
<223> OTHER INFORMATION: Aib

<400> SEQUENCE: 180

Ser Gln Arg Arg Ile Val Gln Met Trp Asn Leu Ala Val His Leu Leu
1               5                   10                  15

Ser Tyr Ala Val Pro Glu Leu Gly Glu Lys Val Leu Xaa Lys Leu Arg
            20                  25                  30

Arg Leu

<210> SEQ ID NO 181
<211> LENGTH: 34
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: Aib

<400> SEQUENCE: 181

Ser Gln Arg Arg Ile Val Gln Met Trp Asn Leu Ala Val His Leu Leu
1               5                   10                  15

Ser Tyr Ala Val Pro Glu Leu Gly Glu Lys Val Leu Glu Xaa Leu Arg
            20                  25                  30

Arg Leu

<210> SEQ ID NO 182

```
<211> LENGTH: 34
<212> TYPE: PRT
<213> ORGANISM: Homo sapiens

<400> SEQUENCE: 182

Ser Gln Arg Arg Ile Val Gln Met Trp Ser Val Ala Val Phe Leu Leu
1               5                   10                  15

Ser Tyr Ala Val Pro Ser Cys Gly Arg Ser Val Glu Gly Leu Ser Arg
            20                  25                  30

Arg Leu

<210> SEQ ID NO 183
<211> LENGTH: 34
<212> TYPE: PRT
<213> ORGANISM: Homo sapiens
<220> FEATURE:
<223> OTHER INFORMATION: Disulphide or amide bond between residues 13
      and 17

<400> SEQUENCE: 183

Ser Val Ser Glu Ile Gln Leu Met His Asn Leu Gly Lys His Leu Asn
1               5                   10                  15

Asp Met Glu Arg Val Glu Trp Leu Arg Lys Lys Leu Gln Asp Val His
            20                  25                  30

Asn Phe

<210> SEQ ID NO 184
<211> LENGTH: 34
<212> TYPE: PRT
<213> ORGANISM: Bos sp.
<220> FEATURE:
<223> OTHER INFORMATION: Disulphide or amide bond between residues 13
      and 17

<400> SEQUENCE: 184

Ala Val Ser Glu Ile Gln Phe Met His Asn Leu Gly Lys His Leu Ser
1               5                   10                  15

Asp Met Glu Arg Val Glu Trp Leu Arg Lys Lys Leu Gln Asp Val His
            20                  25                  30

Asn Phe

<210> SEQ ID NO 185
<211> LENGTH: 34
<212> TYPE: PRT
<213> ORGANISM: Rattus sp.
<220> FEATURE:
<223> OTHER INFORMATION: Disulphide or amide bond between residues 13
      and 17

<400> SEQUENCE: 185

Ala Val Ser Glu Ile Gln Leu Met His Asn Leu Gly Lys His Leu Ala
1               5                   10                  15

Asp Val Glu Arg Met Gln Trp Leu Arg Lys Lys Leu Gln Asp Val His
            20                  25                  30

Asn Phe

<210> SEQ ID NO 186
<211> LENGTH: 34
<212> TYPE: PRT
<213> ORGANISM: Homo sapiens
<220> FEATURE:
<221> NAME/KEY: MOD_RES
<222> LOCATION: (8)..(8)
```

```
<223> OTHER INFORMATION: Nle
<220> FEATURE:
<221> NAME/KEY: MOD_RES
<222> LOCATION: (18)..(18)
<223> OTHER INFORMATION: Nle
<220> FEATURE:
<223> OTHER INFORMATION: Disulphide or amide bond between residues 13
      and 17

<400> SEQUENCE: 186

Ser Val Ser Glu Ile Gln Leu Xaa His Asn Leu Gly Lys His Leu Asn
1               5                   10                  15

Asp Xaa Glu Arg Val Glu Trp Leu Arg Lys Lys Leu Gln Asp Val His
            20                  25                  30

Asn Tyr

<210> SEQ ID NO 187
<211> LENGTH: 34
<212> TYPE: PRT
<213> ORGANISM: Rattus sp.
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (18)..(18)
<223> OTHER INFORMATION: Nle
<220> FEATURE:
<223> OTHER INFORMATION: Disulphide or amide bond between residues 13
      and 17

<400> SEQUENCE: 187

Ala Val Ser Glu Ile Gln Leu Xaa His Asn Leu Gly Lys His Leu Ala
1               5                   10                  15

Asp Xaa Glu Arg Met Gln Trp Leu Arg Lys Lys Leu Gln Asp Val His
            20                  25                  30

Asn Tyr

<210> SEQ ID NO 188
<211> LENGTH: 34
<212> TYPE: PRT
<213> ORGANISM: Bos sp.
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (18)..(18)
<223> OTHER INFORMATION: Nle
<220> FEATURE:
<223> OTHER INFORMATION: Disulphide or amide bond between residues 13
      and 17

<400> SEQUENCE: 188

Ala Val Ser Glu Ile Gln Phe Xaa His Asn Leu Gly Lys His Leu Ser
1               5                   10                  15

Asp Xaa Glu Arg Val Glu Trp Leu Arg Lys Lys Leu Gln Asp Val His
            20                  25                  30

Asn Tyr

<210> SEQ ID NO 189
<211> LENGTH: 34
<212> TYPE: PRT
<213> ORGANISM: Homo sapiens
<220> FEATURE:
```

<223> OTHER INFORMATION: Disulphide or amide bond between residues 26
      and 30

<400> SEQUENCE: 189

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 190
<211> LENGTH: 34
<212> TYPE: PRT
<213> ORGANISM: Bos sp.
<220> FEATURE:
<223> OTHER INFORMATION: Disulphide or amide bond between residues 26
      and 30

<400> SEQUENCE: 190

Ala Val Ser Glu Ile Gln Phe Met His Asn Leu Gly Lys His Leu Ser
1               5                   10                  15

Ser Met Glu Arg Val Glu Trp Leu Arg Lys Lys Leu Gln Asp Val His
            20                  25                  30

Asn Phe

<210> SEQ ID NO 191
<211> LENGTH: 34
<212> TYPE: PRT
<213> ORGANISM: Rattus sp.
<220> FEATURE:
<223> OTHER INFORMATION: Disulphide or amide bond between residues 26
      and 30

<400> SEQUENCE: 191

Ala Val Ser Glu Ile Gln Leu Met His Asn Leu Gly Lys His Leu Ala
1               5                   10                  15

Ser Val Glu Arg Met Gln Trp Leu Arg Lys Lys Leu Gln Asp Val His
            20                  25                  30

Asn Phe

<210> SEQ ID NO 192
<211> LENGTH: 34
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (18)..(18)
<223> OTHER INFORMATION: Nle
<220> FEATURE:
<223> OTHER INFORMATION: Disulphide or amide bond between residues 26
      and 30

<400> SEQUENCE: 192

Ser Val Ser Glu Ile Gln Leu Xaa His Asn Leu Gly Lys His Leu Asn
1               5                   10                  15

Ser Xaa Glu Arg Val Glu Trp Leu Arg Lys Lys Leu Gln Asp Val His
            20                  25                  30

Asn Tyr

```
<210> SEQ ID NO 193
<211> LENGTH: 34
<212> TYPE: PRT
<213> ORGANISM: Bos sp.
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (18)..(18)
<223> OTHER INFORMATION: Nle
<220> FEATURE:
<223> OTHER INFORMATION: Disulphide or amide bond between residues 26
      and 30

<400> SEQUENCE: 193

Ala Val Ser Glu Ile Gln Phe Xaa His Asn Leu Gly Lys His Leu Ser
 1               5                  10                  15

Ser Xaa Glu Arg Val Glu Trp Leu Arg Lys Lys Leu Gln Asp Val His
            20                  25                  30

Asn Tyr

<210> SEQ ID NO 194
<211> LENGTH: 34
<212> TYPE: PRT
<213> ORGANISM: Rattus sp.
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (18)..(18)
<223> OTHER INFORMATION: Nle
<220> FEATURE:
<223> OTHER INFORMATION: Disulphide or amide bond between residues 26
      and 30

<400> SEQUENCE: 194

Ala Val Ser Glu Ile Gln Leu Xaa His Asn Leu Gly Lys His Leu Ala
 1               5                  10                  15

Ser Xaa Glu Arg Met Gln Trp Leu Arg Lys Lys Leu Gln Asp Val His
            20                  25                  30

Asn Tyr

<210> SEQ ID NO 195
<211> LENGTH: 34
<212> TYPE: PRT
<213> ORGANISM: Homo sapiens
<220> FEATURE:
<223> OTHER INFORMATION: Disulphide or amide bond between residues 13
      and 17
<220> FEATURE:
<223> OTHER INFORMATION: Disulphide or amide bond between residues 26
      and 30

<400> SEQUENCE: 195

Ser Val Ser Glu Ile Gln Leu Met His Asn Leu Gly Lys His Leu Asn
 1               5                  10                  15

Asp Met Glu Arg Val Glu Trp Leu Arg Lys Lys Leu Gln Asp Val His
            20                  25                  30

Asn Phe

<210> SEQ ID NO 196
<211> LENGTH: 34
<212> TYPE: PRT
```

```
<213> ORGANISM: Bos sp.
<220> FEATURE:
<223> OTHER INFORMATION: Disulphide or amide bond between residues 13
      and 17
<220> FEATURE:
<223> OTHER INFORMATION: Disulphide or amide bond between residues 26
      and 30

<400> SEQUENCE: 196

Ala Val Ser Glu Ile Gln Phe Met His Asn Leu Gly Lys His Leu Ser
1               5                   10                  15

Asp Met Glu Arg Val Glu Trp Leu Arg Lys Lys Leu Gln Asp Val His
            20                  25                  30

Asn Phe

<210> SEQ ID NO 197
<211> LENGTH: 34
<212> TYPE: PRT
<213> ORGANISM: Rattus sp.
<220> FEATURE:
<223> OTHER INFORMATION: Disulphide or amide bond between residues 13
      and 17
<220> FEATURE:
<223> OTHER INFORMATION: Disulphide or amide bond between residues 26
      and 30

<400> SEQUENCE: 197

Ala Val Ser Glu Ile Gln Leu Met His Asn Leu Gly Lys His Leu Ala
1               5                   10                  15

Asp Val Glu Arg Met Gln Trp Leu Arg Lys Lys Leu Gln Asp Val His
            20                  25                  30

Asn Phe

<210> SEQ ID NO 198
<211> LENGTH: 34
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (18)..(18)
<223> OTHER INFORMATION: Nle
<220> FEATURE:
<223> OTHER INFORMATION: Disulphide or amide bond between residues 13
      and 17
<220> FEATURE:
<223> OTHER INFORMATION: Disulphide or amide bond between residues 26
      and 30

<400> SEQUENCE: 198

Ser Val Ser Glu Ile Gln Leu Xaa His Asn Leu Gly Lys His Leu Asn
1               5                   10                  15

Asp Met Glu Arg Val Glu Trp Leu Arg Lys Lys Leu Gln Asp Val His
            20                  25                  30

Asn Tyr

<210> SEQ ID NO 199
<211> LENGTH: 34
<212> TYPE: PRT
<213> ORGANISM: Rattus sp.
<220> FEATURE:
<221> NAME/KEY: MOD_RES
<222> LOCATION: (8)..(8)
<223> OTHER INFORMATION: Nle
```

```
<220> FEATURE:
<221> NAME/KEY: MOD_RES
<222> LOCATION: (18)..(18)
<223> OTHER INFORMATION: Nle
<220> FEATURE:
<223> OTHER INFORMATION: Disulphide or amide bond between residues 13
      and 17
<220> FEATURE:
<223> OTHER INFORMATION: Disulphide or amide bond between residues 26
      and 30

<400> SEQUENCE: 199

Ala Val Ser Glu Ile Gln Leu Xaa His Asn Leu Gly Lys His Leu Ala
1               5                   10                  15

Asp Xaa Glu Arg Met Gln Trp Leu Arg Lys Lys Leu Gln Asp Val His
            20                  25                  30

Asn Tyr

<210> SEQ ID NO 200
<211> LENGTH: 34
<212> TYPE: PRT
<213> ORGANISM: Bos sp.
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (18)..(18)
<223> OTHER INFORMATION: Nle
<220> FEATURE:
<223> OTHER INFORMATION: Disulphide or amide bond between residues 13
      and 17
<220> FEATURE:
<223> OTHER INFORMATION: Disulphide or amide bond between residues 26
      and 30

<400> SEQUENCE: 200

Ala Val Ser Glu Ile Gln Phe Xaa His Asn Leu Gly Lys His Leu Ser
1               5                   10                  15

Asp Xaa Glu Arg Val Glu Trp Leu Arg Lys Lys Leu Gln Asp Val His
            20                  25                  30

Asn Tyr

<210> SEQ ID NO 201
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 201

Ala Val Ser Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 202
<211> LENGTH: 31
<212> TYPE: PRT
<213> ORGANISM: Homo sapiens
<220> FEATURE:
<221> NAME/KEY: MOD_RES
```

```
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 202

Ala Ala Ser Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 203
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 203

Ala Val Ala Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 204
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 204

Ala Val Ser Ala Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 205
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 205

Ala Val Ser Glu Ala Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 206
```

```
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 206

Ala Val Ser Glu Ile Ala Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 207
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 207

Ala Val Ser Glu Ile Gln Ala Xaa His Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 208
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 208

Ala Val Ser Glu Ile Gln Leu Xaa Ala Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 209
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 209

Ala Val Ser Glu Ile Gln Leu Xaa His Ala Leu Gly Lys His Leu Asn
1               5                   10                  15
```

Ser Lys Glu Arg Val Asp Trp Leu Arg Lys Leu Leu Gln Asp Val
            20                  25                  30

<210> SEQ ID NO 210
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 210

Ala Val Ser Glu Ile Gln Leu Xaa His Asn Ala Gly Lys His Leu Asn
1               5                   10                  15

Ser Lys Glu Arg Val Asp Trp Leu Arg Lys Leu Leu Gln Asp Val
            20                  25                  30

<210> SEQ ID NO 211
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 211

Ala Val Ser Glu Ile Gln Leu Xaa His Asn Leu Ala Lys His Leu Asn
1               5                   10                  15

Ser Lys Glu Arg Val Asp Trp Leu Arg Lys Leu Leu Gln Asp Val
            20                  25                  30

<210> SEQ ID NO 212
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 212

Ala Val Ser Glu Ile Gln Leu Xaa His Asn Leu Ala Lys His Leu Asn
1               5                   10                  15

Ser Lys Glu Arg Val Asp Trp Leu Arg Lys Leu Leu Gln Asp Val
            20                  25                  30

<210> SEQ ID NO 213
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

```
<400> SEQUENCE: 213

Ala Val Ser Glu Ile Gln Leu Xaa His Asn Leu Gly Lys Ala Leu Asn
1               5                   10                  15

Ser Lys Glu Arg Val Asp Trp Leu Arg Lys Leu Leu Gln Asp Val
            20                  25                  30

<210> SEQ ID NO 214
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 214

Ala Val Ser Glu Ile Gln Leu Xaa His Asn Leu Gly Lys His Ala Asn
1               5                   10                  15

Ser Lys Glu Arg Val Asp Trp Leu Arg Lys Leu Leu Gln Asp Val
            20                  25                  30

<210> SEQ ID NO 215
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 215

Ala Val Ser Glu Ile Gln Leu Xaa His Asn Leu Gly Lys His Leu Ala
1               5                   10                  15

Ser Lys Glu Arg Val Asp Trp Leu Arg Lys Leu Leu Gln Asp Val
            20                  25                  30

<210> SEQ ID NO 216
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 216

Ala Val Ser Glu Ile Gln Leu Xaa His Asn Leu Gly Lys His Leu Asn
1               5                   10                  15

Ala Lys Glu Arg Val Asp Trp Leu Arg Lys Leu Leu Gln Asp Val
            20                  25                  30

<210> SEQ ID NO 217
<211> LENGTH: 31
<212> TYPE: PRT
<213> ORGANISM: Homo sapiens
<220> FEATURE:
<221> NAME/KEY: MOD_RES
<222> LOCATION: (8)..(8)
```

```
<223> OTHER INFORMATION: Nle
<220> FEATURE:
<223> OTHER INFORMATION: Disulphide or amide bond between residues 18
      and 22

<400> SEQUENCE: 217

Gly Val Ser Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 218
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 218

Ala Gly Ser Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 219
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 219

Ala Val Gly Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 220
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 220

Ala Val Ser Gly Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 221
<211> LENGTH: 31
```

```
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 221

Ala Val Ser Glu Gly Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 222
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 222

Ala Val Ser Glu Ile Gly Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 223
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 223

Ala Val Ser Glu Ile Gln Gly Xaa His Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 224
<211> LENGTH: 31
<212> TYPE: PRT
<213> ORGANISM: Homo sapiens
<220> FEATURE:
<223> OTHER INFORMATION: Disulphide or amide bond between residues 18
      and 22

<400> SEQUENCE: 224

Ala Val Ser Glu Ile Gln Leu Gly His Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 225
```

```
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 225

Ala Val Ser Glu Ile Gln Leu Xaa Gly Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 226
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 226

Ala Val Ser Glu Ile Gln Leu Xaa His Gly Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 227
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 227

Ala Val Ser Glu Ile Gln Leu Xaa His Asn Gly Gly Lys His Leu Asn
1               5                   10                  15

Ser Lys Glu Arg Val Asp Trp Leu Arg Lys Leu Leu Gln Asp Val
            20                  25                  30

<210> SEQ ID NO 228
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 228

Ala Val Ser Glu Ile Gln Leu Xaa His Asn Leu Gly Gly His Leu Asn
1               5                   10                  15
```

```
Ser Lys Glu Arg Val Asp Trp Leu Arg Lys Leu Leu Gln Asp Val
            20                  25                  30

<210> SEQ ID NO 229
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 229

Ala Val Ser Glu Ile Gln Leu Xaa His Asn Leu Gly Lys Gly Leu Asn
1               5                   10                  15

Ser Lys Glu Arg Val Asp Trp Leu Arg Lys Leu Leu Gln Asp Val
            20                  25                  30

<210> SEQ ID NO 230
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 230

Ala Val Ser Glu Ile Gln Leu Xaa His Asn Leu Gly Lys His Gly Asn
1               5                   10                  15

Ser Lys Glu Arg Val Asp Trp Leu Arg Lys Leu Leu Gln Asp Val
            20                  25                  30

<210> SEQ ID NO 231
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 231

Ala Val Ser Glu Ile Gln Leu Xaa His Asn Leu Gly Lys His Leu Gly
1               5                   10                  15

Ser Lys Glu Arg Val Asp Trp Leu Arg Lys Leu Leu Gln Asp Val
            20                  25                  30

<210> SEQ ID NO 232
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22
```

```
<400> SEQUENCE: 232

Ala Val Ser Glu Ile Gln Leu Xaa His Asn Leu Gly Lys His Leu Asn
1               5                   10                  15

Gly Lys Glu Arg Val Asp Trp Leu Arg Lys Leu Leu Gln Asp Val
            20                  25                  30

<210> SEQ ID NO 233
<211> LENGTH: 31
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: D-Pro
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 233

Pro Val Ser Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 234
<211> LENGTH: 31
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: D-Pro
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 234

Ala Val Pro Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 235
<211> LENGTH: 31
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: D-Pro
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 235

Ala Val Ser Glu Ile Pro Leu Xaa His Asn Leu Gly Lys His Leu Asn
1               5                   10                  15
```

Ser Lys Glu Arg Val Asp Trp Leu Arg Lys Leu Leu Gln Asp Val
            20                  25                  30

<210> SEQ ID NO 236
<211> LENGTH: 31
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: D-Pro
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 236

Ala Val Ser Glu Ile Gln Pro Xaa His Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 237
<211> LENGTH: 31
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: D-Pro
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 237

Ala Val Ser Glu Ile Gln Leu Xaa Pro Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 238
<211> LENGTH: 31
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: D-Pro
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 238

Ala Val Ser Glu Ile Gln Leu Xaa His Pro Leu Gly Lys His Leu Asn
1               5                   10                  15

Ser Lys Glu Arg Val Asp Trp Leu Arg Lys Leu Leu Gln Asp Val
            20                  25                  30

```
<210> SEQ ID NO 239
<211> LENGTH: 31
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: D-Pro
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 239

Ala Val Ser Glu Ile Gln Leu Xaa His Asn Leu Gly Lys Pro Leu Asn
1               5                   10                  15

Ser Lys Glu Arg Val Asp Trp Leu Arg Lys Leu Leu Gln Asp Val
            20                  25                  30

<210> SEQ ID NO 240
<211> LENGTH: 31
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: D-Pro
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 240

Ala Val Ser Glu Ile Gln Leu Xaa His Asn Leu Gly Lys His Pro Asn
1               5                   10                  15

Ser Lys Glu Arg Val Asp Trp Leu Arg Lys Leu Leu Gln Asp Val
            20                  25                  30

<210> SEQ ID NO 241
<211> LENGTH: 31
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: D-Pro
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 241

Ala Val Ser Glu Ile Gln Leu Xaa His Asn Leu Gly Lys His Leu Pro
1               5                   10                  15

Ser Lys Glu Arg Val Asp Trp Leu Arg Lys Leu Leu Gln Asp Val
            20                  25                  30

<210> SEQ ID NO 242
<211> LENGTH: 31
<212> TYPE: PRT
```

```
<213> ORGANISM: Homo sapiens
<220> FEATURE:
<221> NAME/KEY: MOD_RES
<222> LOCATION: (17)..(17)
<223> OTHER INFORMATION: D-Pro
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 242

Ala Val Ser Glu Ile Gln Leu Xaa His Asn Leu Gly Lys His Leu Asn
1               5                   10                  15

Pro Lys Glu Arg Val Asp Trp Leu Arg Lys Leu Leu Gln Asp Val
            20                  25                  30

<210> SEQ ID NO 243
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 243

Ala Val Ser Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 244
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 244

Ala Val Ser Glu Ile Gln Leu Xaa His Asn Leu Gly Lys His Leu Asn
1               5                   10                  15

Ser Asp Glu Arg Val Lys Trp Leu Arg Lys Leu Leu Gln Asp Val
            20                  25                  30

<210> SEQ ID NO 245
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (18)..(18)
<223> OTHER INFORMATION: Ornithine
<220> FEATURE:
<223> OTHER INFORMATION: Disulphide or amide bond between residues 18
      and 22
```

-continued

<400> SEQUENCE: 245

Ala Val Ser Glu Ile Gln Leu Xaa His Asn Leu Gly Lys His Leu Asn
1               5                   10                  15

Ser Xaa Glu Arg Val Asp Trp Leu Arg Lys Leu Leu Gln Asp Val
            20                  25                  30

<210> SEQ ID NO 246
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (22)..(22)
<223> OTHER INFORMATION: Ornithine
<220> FEATURE:
<223> OTHER INFORMATION: Disulphide or amide bond between residues 18
      and 22

<400> SEQUENCE: 246

Ala Val Ser Glu Ile Gln Leu Xaa His Asn Leu Gly Lys His Leu Asn
1               5                   10                  15

Ser Asp Glu Arg Val Xaa Trp Leu Arg Lys Leu Leu Gln Asp Val
            20                  25                  30

<210> SEQ ID NO 247
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 247

Ala Val Ser Glu Ile Gln Leu Xaa His Asn Leu Gly Lys His Leu Asn
1               5                   10                  15

Ser Lys Glu Arg Val Glu Trp Leu Arg Lys Leu Leu Gln Asp Val
            20                  25                  30

<210> SEQ ID NO 248
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (18)..(18)
<223> OTHER INFORMATION: Ornithine
<220> FEATURE:
<223> OTHER INFORMATION: Disulphide or amide bond between residues 18
      and 22

<400> SEQUENCE: 248

Ala Val Ser Glu Ile Gln Leu Xaa His Asn Leu Gly Lys His Leu Asn
1               5                   10                  15

Ser Xaa Glu Arg Val Glu Trp Leu Arg Lys Leu Leu Gln Asp Val
            20                  25                  30

<210> SEQ ID NO 249
<211> LENGTH: 30
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 249

Ala Val Ser Glu Ile Gln Leu Xaa His Asn Leu Gly Lys His Leu Asn
1               5                   10                  15

Ser Lys Glu Arg Val Asp Trp Leu Arg Lys Leu Leu Gln Asp
            20                  25                  30

<210> SEQ ID NO 250
<211> LENGTH: 29
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 250

Ala Val Ser Glu Ile Gln Leu Xaa His Asn Leu Gly Lys His Leu Asn
1               5                   10                  15

Ser Lys Glu Arg Val Asp Trp Leu Arg Lys Leu Leu Gln
            20                  25

<210> SEQ ID NO 251
<211> LENGTH: 28
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 251

Ala Val Ser Glu Ile Gln Leu Xaa His Asn Leu Gly Lys His Leu Asn
1               5                   10                  15

Ser Lys Glu Arg Val Asp Trp Leu Arg Lys Leu Leu
            20                  25

<210> SEQ ID NO 252
<211> LENGTH: 27
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22

<400> SEQUENCE: 252

```
Ala Val Ser Glu Ile Gln Leu Xaa His Asn Leu Gly Lys His Leu Asn
1               5                   10                  15

Ser Lys Glu Arg Val Asp Trp Leu Arg Lys Leu
            20                  25
```

<210> SEQ ID NO 253
<211> LENGTH: 29
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Nle
<220> FEATURE:
<223> OTHER INFORMATION: Disulphide or amide bond between residues 16 and 20

<400> SEQUENCE: 253

```
Ser Glu Ile Gln Leu Xaa His Asn Leu Gly Lys His Leu Asn Ser Lys
1               5                   10                  15

Glu Arg Val Asp Trp Leu Arg Lys Leu Leu Gln Asp Val
            20                  25
```

<210> SEQ ID NO 254
<211> LENGTH: 30
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Nle
<220> FEATURE:
<223> OTHER INFORMATION: Disulphide or amide bond between residues 17 and 21

<400> SEQUENCE: 254

```
Val Ser Glu Ile Gln Leu Xaa His Asn Leu Gly Lys His Leu Asn Ser
1               5                   10                  15

Lys Glu Arg Val Asp Trp Leu Arg Lys Leu Leu Gln Asp Val
            20                  25                  30
```

<210> SEQ ID NO 255
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (18)..(18)
<223> OTHER INFORMATION: Nle
<220> FEATURE:
<223> OTHER INFORMATION: Disulphide or amide bond between residues 10 and 14

<400> SEQUENCE: 255

```
Ala Val Ser Glu Ile Gln Leu Xaa His Lys Leu Gly Lys Asp Leu Asn
1               5                   10                  15

Ser Xaa Glu Arg Val Glu Trp Leu Arg Lys Leu Leu Gln Asp Val
            20                  25                  30
```

<210> SEQ ID NO 256
<211> LENGTH: 31
<212> TYPE: PRT
<213> ORGANISM: Homo sapiens
<220> FEATURE:

```
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 14
      and 18

<400> SEQUENCE: 256

Ala Val Ser Glu Ile Gln Leu Xaa His Asn Leu Gly Lys Lys Leu Asn
1               5                   10                  15

Ser Asp Glu Arg Val Glu Trp Leu Arg Lys Leu Leu Gln Asp Val
                20                  25                  30

<210> SEQ ID NO 257
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (18)..(18)
<223> OTHER INFORMATION: Nle
<220> FEATURE:
<223> OTHER INFORMATION: Disulphide or amide bond between residues 17
      and 21

<400> SEQUENCE: 257

Ala Val Ser Glu Ile Gln Leu Xaa His Asn Leu Gly Lys His Leu Asn
1               5                   10                  15

Lys Xaa Glu Arg Asp Glu Trp Leu Arg Lys Leu Leu Gln Asp Val
                20                  25                  30

<210> SEQ ID NO 258
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (18)..(18)
<223> OTHER INFORMATION: Nle
<220> FEATURE:
<223> OTHER INFORMATION: Disulphide or amide bond between residues 21
      and 25

<400> SEQUENCE: 258

Ala Val Ser Glu Ile Gln Leu Xaa His Asn Leu Gly Lys His Leu Asn
1               5                   10                  15

Ser Xaa Glu Arg Lys Glu Trp Leu Asp Lys Leu Leu Gln Asp Val
                20                  25                  30

<210> SEQ ID NO 259
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (18)..(18)
<223> OTHER INFORMATION: Nle
<220> FEATURE:
```

-continued

```
<223> OTHER INFORMATION: Disulphide or amide bond between residues 25
      and 29

<400> SEQUENCE: 259

Ala Val Ser Glu Ile Gln Leu Xaa His Asn Leu Gly Lys His Leu Asn
1               5                   10                  15

Ser Xaa Glu Arg Val Glu Trp Leu Lys Lys Leu Leu Asp Asp Val
            20                  25                  30

<210> SEQ ID NO 260
<211> LENGTH: 34
<212> TYPE: PRT
<213> ORGANISM: Homo sapiens
<220> FEATURE:
<223> OTHER INFORMATION: Disulphide or amide bond between residues 18
      and 22

<400> SEQUENCE: 260

Ser Val Ser Glu Ile Gln Leu Met His Asn Leu Gly Lys His Leu Asn
1               5                   10                  15

Ser Lys Glu Arg Val Asp Trp Leu Arg Lys Lys Leu Gln Asp Val His
            20                  25                  30

Asn Phe

<210> SEQ ID NO 261
<211> LENGTH: 34
<212> TYPE: PRT
<213> ORGANISM: Homo sapiens
<220> FEATURE:
<223> OTHER INFORMATION: Disulphide or amide bond between residues 18
      and 22

<400> SEQUENCE: 261

Ser Val Ser Glu Ile Gln Leu Met His Asn Leu Gly Lys His Leu Asn
1               5                   10                  15

Ser Lys Glu Arg Val Asp Leu Leu Glu Lys Lys Leu Glu Lys Leu His
            20                  25                  30

Asn Phe

<210> SEQ ID NO 262
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 13
      and 17
<220> FEATURE:
<223> OTHER INFORMATION: Disulphide or amide bond between residues 18
      and 22

<400> SEQUENCE: 262

Ala Val Ser Glu Ile Gln Leu Xaa His Asn Leu Gly Lys His Leu Asn
1               5                   10                  15

Asp Lys Glu Arg Val Asp Trp Leu Arg Lys Leu Leu Gln Asp Val
            20                  25                  30

<210> SEQ ID NO 263
<211> LENGTH: 31
<212> TYPE: PRT
<213> ORGANISM: Homo sapiens
<220> FEATURE:
```

```
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 18
      and 22
<220> FEATURE:
<223> OTHER INFORMATION: Disulphide or amide bond between residues 26
      and 30

<400> SEQUENCE: 263

Ala Val Ser Glu Ile Gln Leu Xaa His Asn Leu Gly Lys His Leu Asn
1               5                   10                  15

Ser Lys Glu Arg Val Asp Trp Leu Arg Lys Leu Leu Gln Asp Val
            20                  25                  30

<210> SEQ ID NO 264
<211> LENGTH: 31
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle
<220> FEATURE:
<223> OTHER INFORMATION: Disulphide or amide bond between residues 13
      and 17
<220> FEATURE:
<223> OTHER INFORMATION: Disulphide or amide bond between residues 18
      and 22
<220> FEATURE:
<223> OTHER INFORMATION: Disulphide or amide bond between residues 26
      and 30

<400> SEQUENCE: 264

Ala Val Ser Glu Ile Gln Leu Xaa His Asn Leu Gly Lys His Leu Asn
1               5                   10                  15

Asp Lys Glu Arg Val Asp Trp Leu Arg Lys Leu Leu Gln Asp Val
            20                  25                  30

<210> SEQ ID NO 265
<211> LENGTH: 40
<212> TYPE: PRT
<213> ORGANISM: Homo sapiens

<400> SEQUENCE: 265

Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
            20                  25                  30

Arg Leu Lys Arg Ala Val Ser Glu
        35                  40

<210> SEQ ID NO 266
<211> LENGTH: 33
<212> TYPE: PRT
<213> ORGANISM: Homo sapiens

<400> SEQUENCE: 266

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp
```

```
<210> SEQ ID NO 267
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Met or an oxidatively stable Met-replacement
      Amino acid

<400> SEQUENCE: 267

Glu Met Asn Thr Ile
1               5

<210> SEQ ID NO 268
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Tyr Ser Lys Tyr
1

<210> SEQ ID NO 269
<211> LENGTH: 31
<212> TYPE: PRT
<213> ORGANISM: Homo sapiens

<400> SEQUENCE: 269

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val
            20                  25                  30

<210> SEQ ID NO 270
<211> LENGTH: 31
<212> TYPE: PRT
<213> ORGANISM: Homo sapiens
<220> FEATURE:
<223> OTHER INFORMATION: Disulphide or amide bond between residues 22
      and 26

<400> SEQUENCE: 270

Ser Val Ser Glu Ile Gln Leu Met His Asn Leu Gly Lys His Leu Asn
1               5                   10                  15

Ser Met Glu Arg Val Glu Trp Leu Arg Lys Leu Leu Gln Asp Val
            20                  25                  30

<210> SEQ ID NO 271
<211> LENGTH: 34
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Gly, D-Ser, D-Ala, or Tyr

<400> SEQUENCE: 271

Xaa Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
```

```
                    20                  25                  30

Asn Phe

<210> SEQ ID NO 272
<211> LENGTH: 34
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Ala, D-Val, Lys, Arg, or Cit
<220> FEATURE:
<221> NAME/KEY: MOD_RES
<222> LOCATION: (8)..(8)
<223> OTHER INFORMATION: Met or Nle
<220> FEATURE:
<221> NAME/KEY: MOD_RES
<222> LOCATION: (18)..(18)
<223> OTHER INFORMATION: Met or Nle
<220> FEATURE:
<221> NAME/KEY: MOD_RES
<222> LOCATION: (34)..(34)
<223> OTHER INFORMATION: Tyr or D-Tyr
<220> FEATURE:
<223> OTHER INFORMATION: See specification as filed for detailed
      description of substitutions and preferred embodiments

<400> SEQUENCE: 272

Ser Xaa Ser Glu Ile Gln Leu Xaa His Asn Leu Gly Lys His Leu Asn
1               5                   10                  15

Ser Xaa Glu Arg Val Glu Trp Leu Arg Lys Lys Leu Gln Asp Val His
                20                  25                  30

Asn Xaa

<210> SEQ ID NO 273
<211> LENGTH: 34
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Variable natural or unnatural amino acid
<220> FEATURE:
<221> NAME/KEY: MOD_RES
<222> LOCATION: (6)..(6)
<223> OTHER INFORMATION: Variable natural or unnatural amino acid
<220> FEATURE:
<221> NAME/KEY: MOD_RES
<222> LOCATION: (9)..(9)
<223> OTHER INFORMATION: Variable natural or unnatural amino acid

<400> SEQUENCE: 273

Ser Val Xaa Glu Ile Xaa Leu Met Xaa Asn Leu Gly Lys His Leu Asn
1               5                   10                  15

Ser Met Glu Arg Val Glu Trp Leu Arg Lys Lys Leu Gln Asp Val His
                20                  25                  30

Asn Phe

<210> SEQ ID NO 274
<211> LENGTH: 34
<212> TYPE: PRT
<213> ORGANISM: Homo sapiens
<220> FEATURE:
<221> NAME/KEY: MOD_RES
<222> LOCATION: (23)..(23)
<223> OTHER INFORMATION: Ala, Arg, Asn, Asp, Cys, Gln, Glu, Gly, His,
      Ile, Lys, Met, Pro, Ser, or Thr

<400> SEQUENCE: 274
```

```
Ser Val Ser Glu Ile Gln Leu Met His Asn Leu Gly Lys His Leu Asn
1               5                   10                  15

Ser Met Glu Arg Val Glu Xaa Leu Arg Lys Lys Leu Gln Asp Val His
            20                  25                  30

Asn Phe

<210> SEQ ID NO 275
<211> LENGTH: 34
<212> TYPE: PRT
<213> ORGANISM: Homo sapiens
<220> FEATURE:
<221> NAME/KEY: MOD_RES
<222> LOCATION: (25)..(25)
<223> OTHER INFORMATION: Ala, Arg, Asn, Asp, Cys, Gln, Glu, Gly, His,
      Ile, Leu, Met, Phe, Pro, Ser, Thr, Trp, Tyr, or Val
<220> FEATURE:
<221> NAME/KEY: MOD_RES
<222> LOCATION: (26)..(27)
<223> OTHER INFORMATION: Ala, Asn, Asp, Cys, Gln, Glu, Gly, His, Ile,
      Lys, Leu, Met, Phe, Pro, Ser, Thr, Trp, Tyr, or Val
<220> FEATURE:
<223> OTHER INFORMATION: See specification as filed for detailed
      description of substitutions and preferred embodiments

<400> SEQUENCE: 275

Ser Val Ser Glu Ile Gln Leu Met His Asn Leu Gly Lys His Leu Asn
1               5                   10                  15

Ser Met Glu Arg Val Glu Trp Leu Xaa Xaa Xaa Leu Gln Asp Val His
            20                  25                  30

Asn Phe

<210> SEQ ID NO 276
<211> LENGTH: 34
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Nle or Met(O)
<220> FEATURE:
<221> NAME/KEY: MOD_RES
<222> LOCATION: (12)..(12)
<223> OTHER INFORMATION: Gly, L-Pro, D-Pro, L-Ala, D-Ala, Aib, or NMeGly
<220> FEATURE:
<221> NAME/KEY: MOD_RES
<222> LOCATION: (18)..(18)
<223> OTHER INFORMATION: Nle or Met(O)
<220> FEATURE:
<221> NAME/KEY: MOD_RES
<222> LOCATION: (23)..(23)
<223> OTHER INFORMATION: Trp, Phe, Leu, Nle, Val, Tyr, alpha-Nal, or
      Beta-Nal
<220> FEATURE:
<221> NAME/KEY: MOD_RES
<222> LOCATION: (34)..(34)
<223> OTHER INFORMATION: Phe or Tyr
<220> FEATURE:
<223> OTHER INFORMATION: See specification as filed for detailed
      description of substitutions and preferred embodiments

<400> SEQUENCE: 276

Ser Val Ser Glu Ile Gln Leu Xaa His Asn Leu Xaa Lys His Leu Asn
1               5                   10                  15

Ser Xaa Glu Arg Val Glu Xaa Leu Arg Lys Lys Leu Gln Asp Val His
            20                  25                  30

Asn Xaa
```

```
<210> SEQ ID NO 277
<211> LENGTH: 34
<212> TYPE: PRT
<213> ORGANISM: Homo sapiens

<400> SEQUENCE: 277

Ser Val Ser Glu Ile Gln Leu Met His Asn Leu Gly Lys His Leu Asn
1               5                   10                  15

Ser Met Glu Arg Val Glu Trp Leu Arg Lys Lys Gln Leu Val His
            20                  25                  30

Asn Phe

<210> SEQ ID NO 278
<211> LENGTH: 34
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Ser or Aib
<220> FEATURE:
<221> NAME/KEY: MOD_RES
<222> LOCATION: (8)..(8)
<223> OTHER INFORMATION: Met, Leu, Ile, Val, Phe, or Trp
<220> FEATURE:
<221> NAME/KEY: MOD_RES
<222> LOCATION: (11)..(11)
<223> OTHER INFORMATION: Leu, Ser, Lys, Phe, Beta-Nal, Trp, or Tyr
<220> FEATURE:
<221> NAME/KEY: MOD_RES
<222> LOCATION: (12)..(12)
<223> OTHER INFORMATION: Gly, D-Leu, D-Ile, D-Nle, D-Val, D-Ser,
      D-Ser(Butyl) D-Abu, D-Thr, D-Nva, D-Met, D-beta-Nal, D-Trp,
      D-Lys, D-Tyr, D-Phe, or D-Asn
<220> FEATURE:
<221> NAME/KEY: MOD_RES
<222> LOCATION: (13)..(13)
<223> OTHER INFORMATION: Lys or Leu
<220> FEATURE:
<221> NAME/KEY: MOD_RES
<222> LOCATION: (18)..(18)
<223> OTHER INFORMATION: Met, Leu, Ile, Val, Phe, or Trp
<220> FEATURE:
<221> NAME/KEY: MOD_RES
<222> LOCATION: (19)..(19)
<223> OTHER INFORMATION: Glu, Arg, Lys, Asn or His
<220> FEATURE:
<221> NAME/KEY: MOD_RES
<222> LOCATION: (21)..(21)
<223> OTHER INFORMATION: Val, Arg, Lys, Asn or His
<220> FEATURE:
<221> NAME/KEY: MOD_RES
<222> LOCATION: (23)..(23)
<223> OTHER INFORMATION: Trp or 2-(1,3-dithiolane-2-yl)Trp
<220> FEATURE:
<221> NAME/KEY: MOD_RES
<222> LOCATION: (25)..(25)
<223> OTHER INFORMATION: Arg or His
<220> FEATURE:
<221> NAME/KEY: MOD_RES
<222> LOCATION: (26)..(26)
<223> OTHER INFORMATION: Lys or His
<220> FEATURE:
<221> NAME/KEY: MOD_RES
<222> LOCATION: (27)..(27)
<223> OTHER INFORMATION: Lys, Gln, or Leu
<220> FEATURE:
<223> OTHER INFORMATION: See specification as filed for detailed
      description of substitutions and preferred embodiments

<400> SEQUENCE: 278

Xaa Val Ser Glu Ile Gln Leu Xaa His Asn Xaa Xaa Xaa His Leu Asn
1               5                   10                  15
```

```
-continued

Ser Xaa Xaa Arg Xaa Glu Xaa Leu Xaa Xaa Xaa Leu Gln Asp Val His
            20          25              30

Asn Phe

<210> SEQ ID NO 279
<211> LENGTH: 34
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Met, Ala, Ser, Val, Leu, Ile, or Trp
<220> FEATURE:
<221> NAME/KEY: MOD_RES
<222> LOCATION: (18)..(18)
<223> OTHER INFORMATION: Met, Ala, Ser, Val, Leu, Ile, or Trp
<220> FEATURE:
<221> NAME/KEY: MOD_RES
<222> LOCATION: (34)..(34)
<223> OTHER INFORMATION: Phe or Tyr
<220> FEATURE:
<223> OTHER INFORMATION: See specification as filed for detailed
      description of substitutions and preferred embodiments

<400> SEQUENCE: 279

Ser Val Ser Glu Ile Gln Leu Xaa His Asn Leu Gly Lys His Leu Asn
1               5                   10                  15

Ser Xaa Glu Arg Val Glu Trp Leu Arg Lys Lys Leu Gln Asp Val His
            20                  25              30

Asn Xaa
```